(12) United States Patent
Romano et al.

(10) Patent No.: US 8,939,950 B2
(45) Date of Patent: **\*Jan. 27, 2015**

(54) SUPPLY CHAIN METHOD AND APPARATUS FOR SEALING AND UNSEALING A VACUUM DRAW PATH

(75) Inventors: Jack Woodward Romano, Kirkland, WA (US); Adam L Smith, Seattle, WA (US)

(73) Assignee: Medindica-Pak, Inc, Kirkland, WA (US)

( \* ) Notice: Subject to any disclaimer, the term of this patent is extended or adjusted under 35 U.S.C. 154(b) by 1057 days.

This patent is subject to a terminal disclaimer.

(21) Appl. No.: 12/927,049

(22) Filed: Nov. 5, 2010

(65) Prior Publication Data

US 2011/0118681 A1    May 19, 2011

Related U.S. Application Data

(63) Continuation of application No. 11/787,036, filed on Apr. 13, 2007, now Pat. No. 7,845,729.

(60) Provisional application No. 60/792,568, filed on Apr. 17, 2006.

(51) Int. Cl.
| | |
|---|---|
| *A61M 1/00* | (2006.01) |
| *G06Q 10/08* | (2012.01) |
| *G06Q 10/00* | (2012.01) |
| *G06Q 20/20* | (2012.01) |
| *G06Q 30/02* | (2012.01) |
| *G06Q 50/22* | (2012.01) |

(52) U.S. Cl.
CPC ......... *A61M 1/0001* (2013.01); *G06Q 10/0832* (2013.01); *G06Q 10/0833* (2013.01); *G06Q 10/08355* (2013.01); *G06Q 10/087* (2013.01); *G06Q 10/0875* (2013.01); *G06Q 10/30* (2013.01); *G06Q 20/203* (2013.01); *G06Q 30/0223* (2013.01); *G06Q 50/22* (2013.01)
USPC ........................................................ 604/317

(58) Field of Classification Search
USPC .............. 604/317–319; 211/22, 74, 85, 85.13
See application file for complete search history.

(56) References Cited

U.S. PATENT DOCUMENTS

| | | | | |
|---|---|---|---|---|
| 1,912,505 | A * | 6/1933 | Turner et al. | 220/552 |
| 2,628,493 | A * | 2/1953 | Sandefur | 73/305 |
| 2,903,127 | A * | 9/1959 | Dorman | 206/338 |
| 3,167,202 | A * | 1/1965 | Tolciss | 215/307 |
| 3,689,051 | A * | 9/1972 | Miller | 266/275 |
| 3,782,414 | A * | 1/1974 | Holbrook | 137/575 |
| 3,812,997 | A * | 5/1974 | McNally | 220/529 |
| 4,514,815 | A * | 4/1985 | Anderson | 700/215 |
| 4,678,149 | A * | 7/1987 | Chase | 248/150 |
| 5,038,283 | A * | 8/1991 | Caveney | 705/28 |
| 5,188,622 | A * | 2/1993 | Muller et al. | 604/319 |
| 5,310,068 | A * | 5/1994 | Saghri | 215/386 |
| 5,752,234 | A * | 5/1998 | Withers | 705/2 |
| 5,899,349 | A * | 5/1999 | Moore | 215/277 |

(Continued)

FOREIGN PATENT DOCUMENTS

GB          2 166 108 A  *  4/1986  ............. B65D 25/28

*Primary Examiner* — Philip R Wiest

(57) ABSTRACT

This application teaches a disposal chain and a supply chain system for sealing and unsealing a vacuum draw path embodying a thrust handle capable of imparting assembly and disassembly thrust forces said system conferring the potential of reducing the amount solid waste mass contributed to the waste stream.

24 Claims, 35 Drawing Sheets

(56) References Cited

U.S. PATENT DOCUMENTS

| | | | |
|---|---|---|---|
| 6,318,417 B1* | 11/2001 | Davis et al. | 141/1 |
| 6,684,922 B1* | 2/2004 | Alston et al. | 141/375 |
| 6,789,690 B2* | 9/2004 | Nieh et al. | 220/231 |
| 6,942,123 B2 | 9/2005 | Wertenberger | |
| 7,040,584 B2* | 5/2006 | Welland et al. | 248/146 |
| 7,185,681 B2* | 3/2007 | Romano | 141/9 |
| 7,329,250 B2* | 2/2008 | Romano et al. | 604/540 |
| 7,854,729 B2* | 12/2010 | Romano et al. | 604/317 |
| 7,931,629 B2* | 4/2011 | Romano | 604/317 |
| 8,118,795 B2* | 2/2012 | Romano et al. | 604/318 |
| 8,137,329 B2* | 3/2012 | Romano et al. | 604/319 |
| 8,353,885 B2* | 1/2013 | Romano et al. | 604/319 |
| 2004/0149348 A1 | 8/2004 | Wertenberger | |
| 2009/0057347 A1 | 3/2009 | Leys | |

* cited by examiner

SUPPLY CHAIN METHOD AND APPARATUS FOR SEALING AND UNSEALING A VACUUM DRAW PATH

CROSS REFERENCE TO RELATED APPLICATION

Under 35 USC 120, this patent application is a continuation of U.S. patent application Ser. No. 11/787,036 filed on Apr. 13, 2007, now U.S. Pat. No. 7,854,729 which claims priority under 35 USC 119 from U.S. Provisional Patent Application No. 60/792,568 which was filed on Apr. 17, 2006.

FIELD OF THE INVENTION

This invention relates to the field of reducing the waste stream burden in the medical field, but not limited to that.

BACKGROUND OF THE INVENTION

In particular, this application relates to systems used in the collection and disposal of certain medical wastes. The collection of fluent waste material is a common procedure in the medical field. Most methods of surgical waste collection are carried out using vacuum suction. Some methods use gravity, while some use impelling devices which produce suction vacuum. Examples of such impelling devices may comprise a meniscus shaver, a lipo-suction system, an arthroscopic fluid pump, a tissue ablator, an endoscopic irrigation and aspiration wand and the like. Surgical fluid waste is collected in containers commonly referred to as canister and/or canister liners. These waste collection devices are generally disposable; some are re-cycled, re-processed, or rewashed. Some collection devices are re-used. Some are partially reused while some are intermittently re-used. Some are disposable or partially disposable. Some are used in conjunction with servicing units while some are used with additive agents for treating the waste material. Some are used multiple times on multiple patients without the preferable cleaning in between treatment of different patients. In certain instances reused devices are cleaned, reprocessed, sterilized, re-sterilized and or recycled and or prepared for reuse. There are disadvantages to the use of disposable collection canisters and canister liners. One problem is that disposable collection canisters and disposable collection liners contribute contaminated infectious plastic waste to the medical waste stream which is undesirable for the environment. Reuse of disposable collection devices by recleaning or reprocessing or recycling and or sterilizing, has the disadvantages of adding costly labor and requiring additional labor costs for sorting, containing transporting and handling of contaminated medical waste containers, and then the added costs of product re-entry into the internal/external product re-sterilization internal/external distribution system. There is a significant need to reduce medical waste. The need to reduce medical waste is a serious common goal of the United States and Internal Agencies. The Environmental Protection Agency (EPA) and the American Hospital Association has entered into a landmark Memorandum of Understanding (MOU) formally establishing the goals to reduce medical waste 50% by the year 2010. Hospitals for Healthy Environment (www.H2E-Online.org) is the name of the aforementioned alliance for waste reduction, supported by formidable organizations and companies such as the American Nurses Association, Healthcare Without Harm, the EPA, plus Group Purchasing Organization, leading health care organization, federal, state and local government agencies and health care associations and the like.

DESCRIPTION OF THE PRIOR ART

It is important in the health care field to have good quality sturdy and reliable products. This is true especially in the field of collection of contaminated biological waste material. Containers for these purposes must be easy to use, and be designed with good human factors and ergonomics for the operators of such devices. One key important ergonomic feature is that the systems for collection of biological waste must be easy to use, and the amount of effort and strength required to assemble such systems should be easy and require little effort by the operators. The instant embodiments of the instant case provide for such ease of use. In addition other useful features which represent good quality standards for collection containers and systems and methods involve stability so that when containers are placed on a horizontal surface they are stable. The container should be puncture, leak and impact resistant and be stable and secure when dropped. It should be manufactured out of materials which function for the intended purposes, and if made form a polymer, have a durometer should not crack or break if dropped. Labels and brackets should be made durable. The system should be autoclavable so that if desired by the customer it may be reused. The systems should be available in various sizes to accommodate a variety of patient populations as well as be effective to operate in a number of different treatment situations and locations. The system should not have any parts that are sharp, that might compromise the operator's personal protection, and not tear gloves, or other personal protective equipment such as gowns, gloves, masks, etc. Designs of systems of this sort should promote safe clinical care and perform according to those safe clinical standards. The design should promote resistance to opening after final sealing for disposal, as well as promote easy assemble and easy opening (in this case easy sealing and unsealing) with good ergonomic and human factor attributes. All closure seals should function tightly and maintain the leak proof seal during use, handling and transport. The design should accommodate easy carrying and handling so that transport of the systems may be done safely without contaminating the surrounding environment. Grips and handles should be designed for ease of access and use. Parts should be designed for ease of decontamination, and be rugged to withstand multiple autoclaving if desired. Opening must be free of obstruction, entanglement and sub-assembly parts must be able to attach and dis-attach without requiring undue hand work or significant effort.

In addition various scenarios that occur during health are supply chain efficiency and supply management require unique features to products that encounter such scenarios. Some scenarios occur in the operating room. For example, in collection systems the y should be designed to be easy to use during room turnover. They should be easy to use during intra-operative system changing. They should be easy to use after terminal sterilization and room setup. And they should be easy to use when preparing an operating room at the beginning of the operating day. Such collection systems should be easy to check/test to make sure they are operating correctly. Especially in a vacuum suction collection system, testing suction and checking seal must be easy and without undue fiddling or parts manipulation. This is especially significant whereas many time the individual who may be preparing the collection system for use, may do so prior to and at time different than actual use, which means the operator setting up the system for use is not the same operator using the system to collect waste. Ease of checking/testing, especially of the seals becomes important if, for example the prior individual does not properly assemble or prepare the system for subsequent use and the operator must then insure the system is in intended working condition at a later time. It is also desirable, when dealing with contaminated biological waste that minimum handling of unsealed containers holding biological waste material is kept to a minimum, and that containers are sealed prior to handling and transport. It is also important that a minimum of handling be required during the various scenarios mentioned above and that hand and hand coordination may be achieved to carry out the aforementioned clinical safety features. It is understood that the aforesaid features for the aforesaid scenarios do not only apply to the operating room. Other settings as further defined by the instant application are all applicable. Another example is that safe sealing of containers containing biological waste must be achievable with one handed technique as provided by the instant system. The feature of creating a stand 3, that has different dimension from a system centerline so that as cap 15 may be placed on a container 14 having waste material therein is a good clinically safe procedure. This sealed bottle is them removed with one hand, and replaced with an empty container while the other hand is occupied holding lid 4. The container stand/container relationship provides for anti rotation of the stand while cap 15 is securely threaded down to seal the container holding the biological waste material. These practical features bring good ergonomic and human factors to the instant system while providing a good clinically safe system into the health care setting.

Certain disadvantages of the prior art in these regards will become better understood with the explanations of the following references. U.S. Pat. No. 5,792,126 to Tribastone, et. Al., discloses a collection canister system comprising canister interior of preferably 5000, 10000, and 15000 cubic centimeters and taught to be effective for all procedures. A container of this size has disadvantages because it is too big for many collection applications. For example, suction collection for anesthesia where it is convenient to have a small collection canister attached to an anesthesia machine is preferable, especially in that most anesthesia suction volumes constitute just a few cubic centimeters of sputum or pharyngeal throat saliva most of the time. Larger equipment is also inconvenient in smaller rooms where suction collection equipment is found such as in the emergency room, the intensive care unit, the coronary care unit, patient hospital rooms, the neo-natal infant care units, physician offices, physician owned surgery suites, physician office surgery and procedure rooms, outpatient surgery centers, ambulatory surgery center, ambulances and other rooms beside operating rooms which require smaller apparatus for smaller more confined spaces. There are also concerns with cross contamination in any system where contaminated waste material remains in a room during the presence of subsequent multiple patients. Another disadvantage of the larger 5000, 10000, 15000 cc containers is weight and mobility. Such weight in the extremely large heavy volumes are sometimes difficulty ergonomics imposing risk of injury to personnel such as back pain, and other injuries whereby by seams in floors and door jams which are not smooth may induce tipping over and spillage of large volumes of medical waste. Another disadvantage of such large heavy containers is its size. Such large container are ore difficult to keep clean and cumbersome to handle, and because of the awkward size and could cause ergonomic strain as related to the U.S. Pat. No. 5,792,126 reference. U.S. Pat. No. 5,960,837 to Cude et. Al., discloses a suction canister and id combination whereby only a destructive force will only separate the parts which renders the Cude invention to be an only disposable product which is costly whereby each time a canister is used another is purchase to replace it. A purchase is made and is costly to the customer and each plastic disposable product enters the disposal chain waste stream and another piece of garbage enters the land fills or incinerators which are disadvantages. This is expensive, and requires ongoing inventory space, inventory handling which are at a premium. Another disadvantage is a lack of choice for the customer to re-process, re-sterilize or re-use which options are beneficial but not available with the U.S. Pat. No. 5,960,837 reference. U.S. Pat. No. 5,901,717 to Dunn et. Al., discloses a canister and flushing system. This system comprises a complex system for handling a collection canister. This disadvantages of this system are expensive equipment is required and it is complex equipment. These expenses and maintenance plus require periodic inspection by biomedical engineering which increases labor costs associated with its presence. In addition the equipment must be kept clean which is additional requirement for daily operations. Other disadvantages a reusable canister which requires costly labor for internal processing, reprocessing, resterilization and reusing. In most institutions, volume of such collection systems is quite high imposing internal/external processing costs. The system discloses the disposable flush kit which maintains higher disposable costs along with the higher costs associated with internal distribution, inventory handling and higher disposable waste removal costs. U.S. Pat. No. 4,419,093 to Deaton discloses a reusable canister having a disposable lid and liner. This system id delivered in pieces and requires subassembly by the customer prior to operation. This requires additional labor which is costly and involves the inventory tracking a plurality of pieces to a system in sets and often times lids and liner can become separated and when out of numeral matching balance one cannot be use with out the other, whereas resulting in a incomplete set and a unusable subassembly. This disadvantage complicates the ongoing internal/external distribution and tracking of pieces which adds costly labor, inventory management and excess handling. The U.S. Pat. No. 4,419,093 reference also discloses contribution of garbage to the waste stream which is a serious environmental concern. Other disadvantages of disposable collection container include the difficulty in which to assemble a lid to a container body. Many disposable canister systems have a container body which is stackable. This stack ability allow the container bodies to be nested on each other with one container resting substantially within the other with the exception of about one to two inches of body length. This stack ability feature is desirable whereas the volume of containers handling in the disposable application is very high. For example a busy institution may process anywhere between 10,000 and 50,000 disposable canisters per year. The stack ability feature makes these canisters easier to transport in volume. One problem with the assembly of such stackable canister and it s associated lid, is that the snap on feature of lid must be very tight in order to be fluid leak proof in the event of tip over. In order for these canister lid interfaces to be leak proof they must fit very tightly making for a very difficult assembly. The force required to assemble the canister and lids of this nature is greater that a force which would normally be deemed easy to use. In fact they are very difficult to use. Good ergonomic systems include assembly and dies-assembly features that do not require undue finger, hand and/or upper body strength. May of the prior art collectin systems have snap together features that, due to their seal design. Require more force to assemble, than most operators can provide. This is because of the force required to snap together the seals that =are not meant to come apart, and that must be tight enough to stay sealed during transport, handling and tipping over. The applicant believes that if a system cannot be assemble with much less force and upper body strength of the average operator, then there are human factors and ergonomics design issues that are solved by the instant case. The applicant believes that the snap fit force utilized to keep a lid and canister housing together during transport and tippage is not the same force that provides for good human factor/ergonomic and good clinical handling. Applicant contents that when snap fit forces are greater that the average upper body strength of the average operator, then clinical safety is in jeopardy and personal protective equipment such as protective gloves are at risk for tearing or hole.

DESCRIPTION OF THE INVENTION

The instant embodiments provides methods and apparatus for utilizing fluid enclosing product transfer delivery container which do not embody the self inherent physical construct capacity to maintain shape under extreme negative vacuum pressures up to negative minus 1 atmospheres. Examples of cost effectively fabricated fluid enclosing containers made for delivery of fluids which may not embody inherent implosion resistant structural strength and rigidity needed for suction vacuum collection may include plastic delivery containers such as plastic pour bottles and intravenous containers. The present invention discloses cost effective practical solutions for reducing waste, reducing labor, reducing inventory, reducing the receiving, reducing the internal distribution, and reducing the inventory handling costs and the space required to carry inventory all involved with the collection waste materials. These achievements are carried out by the instant embodiments whereby successful suction vacuum collection may be realized using in a flexible manner cost effectively fabricated fluid enclosing distribution, commercialization, and transfer delivery containers. This patent application discloses collection systems that teach use of fluid enclosing product supply containers for collection, removal and disposal of waste material and into the disposal chain. In particular, delivery containers for general distribution, transfer, administration of pour bottle solutions and intravenous solution, parenteral and enteral solution container and the like are converted into the waste collection and disposal chain. This application also teaches use of a common fluid enclosing container for both the supply and the disposal chain. The instant application also teaches use of containers found in inventory for supply and delivery of fluids and then transforming them for the collection removal, and disposal utility found in the deposal chain. This application teaches the use of a common fluid enclosing container for the product transfer and the integrates the container into systems for the collection and the removal of waste material. The instant application teaches waste reduction methods by integrating delivery containers fabrication and the collecting and disposing of waste materials. Two potential container fabrication applicable to the applicable to the instant case comprise blow fill seal manufacturing, blow molding or continuous blow molding which produce an open top container. Another type of container fabrication process applicable to the instant application is a blow fill seal fabrication process commonly knows and a close top manufacturing process whereby a container is formed, filled with fluid and hermetically closed within one machine. The instant application teaches the waste reduction methods by using manufacturing methods as mentioned such as blow molding, blow fill sealing, laminating sheets such as in intravenous solution container making methods to form enclosures. The purpose is to transform these containers which are derived from a fluid delivery mode from product transfer and administration and the converting the container to collection removal and disposal of waste materials.

The embodiments of these instant case provides container utility options for the transfer and administration of products, consumption of products and for the waste collection removal and disposal options. The embodiments of this instant case discloses the utilization of fluid filled product transfer containers such as pour bottles and/or intravenous solution containers (IV bags) (and/or other product/fluid containing enclosures used for intravenous therapeutics and the administration of anesthetic agents as well as other medicaments) for the receiving, collecting, containment and disposal of waste. Using fluid enclosing product distribution transfer/administration containers also for the handling of waste results in optimal reduction of waste, reduction of inventory, reduction in labor, reduction of internal/external inventory distribution/processing/re-processing/re-using/re-cycling, reduction of inventory handling and waste disposal costs (brought by the (unnecessary) the need for separate supply and disposal containers in certain circumstances), all are reduced by eliminating the supply chain costs with the fabrication of the said separate supply and disposal/collection containers. The question arises why pay for disposable container when a fluid delivery container can be derived from the supply side of the supply and disposal side and then converted into a collection and removal/disposal container. Such container are supplied clean/sterile and are made to meet certain sterility assurance levels (SAL). The instant embodiments confer options allowing consumer choices for the reduction of waste. Plastic transfer containers such as blow molded containers, continuous containers, blow fill seal containers, intravenous solution containers, containers made of laminated sheets of polymers and of foils, are commonly used for the distribution transfer and administration of fluid products and other product such as sterile water, sterile saline solution intravenous solutions for IV therapeutics, IV solutions for administration of anesthetic agents and other water for injection (WFI) based fluid formularies as used in the medical field. Also included are cleaning solvents, prep solutions, alcohol solution and the like. These solutions are used for intravenous therapeutics, parenteral administration, and administration of anesthesia, wound irrigation, irrigation for arthroscopic, endoscopic, laparoscopic procedures, irrigation for urology procedures and many other types of applications. The instant application names additional fluid materials delivered in polypropylene, and high density/low density polyethylene polyvinyl chloride containers which are all generally high volume supplies and or engage the supply chain on a just in time basis or on a vendor managed inventory managed basis or a customer managed basis for delivery and consumption. Intravenous solution containers are also used for the distribution/commercialization of these container products. It is understood the disclosed teaching of the instant case are not limited to sterile liquid distribution/supply containers or the transfer of fluid filled product containers. Other product transfer containers may be suitable integrated with innovation of the instant case, to function with the delivery and waste disposal capacity. Other container such as prep solution containers, alcohol containers, solvent containers, cleaning solution containers and the like may function suitable within the scope of the present invention. These teaching are not intended to limit the attached claims below. Other product containers may also be used in the instant inventions. These product delivery containers are commercialized/distributed to the customer having volume cubic capacity sufficient in substantial proportion to the collection and the disposal of waste materials. The instant embodiments reduce the amount of plastic introduced to the waste stream. The instant embodiments reduce the recycling, reprocessing and labor associated with the handling and re-use procedures thereby lowering the associated costs of waste removal. The instant embodiments reduce the supply chain costs from manufacturing to disposal. Collecting fluent waste material in fluid enclosing delivery containers such as open top blow molded, or continuous containers, intravenous solution containers or closed top blow fill seal containers which have been const effectively fabricated with thin walls which do not have the strength or construction to resist high vacuum implosion forces provide various solution. Options solving the disadvantages and problems of prior art containers. When the methods and apparatus embodied in the teaching in the instant application are utilized, the instant embodiments also provides for reducing the handing, reducing the labor and reducing the costly process of recycling, re-using re-processing sterilizing and or re-sterilizing. Certain product delivery transfer containers are fabricated commercialized and are already present or in the supply, distribution, inventory, administration chain and or in the customer facility. Present invention conveniently transforms converts and integrates these fluid enclosing transfer delivery containers for their transformation to waste materials collection containers creating a new type of environmental supply chain. We refer in part to this new novel environmental process as a disposal chain supply system by the deployment of disposal chain supplies to collect, remove and dispose of waste material. This defines new supply and disposal chain systems, methods and apparatus for using fluid enclosing distribution containers and methods for processing systems from the clean delivery side to the fluid administration/consumption into the dirty collection removal and disposal side integrating the disposal chain and the supply chain for environmental purposes herein referred to as disposal chain supply systems. In essence disposal chain supply systems define a novel environmental process. In essence disposal chain supply systems are defined by transforming distributing containers into collection removal and disposal containers. In essence a dispose and supply containers an environmental conversion and transformation methods. In essence a disposal chain/supply chain container utilizing disposal chain supply chain systems confers to =options and advantages and disclosed by the instant case. In essence disposal supplies are environmentally preferred. In essence disposal supplying is the environmentally preferred method.

Difficulties exist with the use of certain containers when integrated into high negative pressure vacuum/suction system. Negative vacuum draw pressures at times up to minus one atmosphere of negative pressure is common for drawing surgical waste materials from a surgical site into a collection receptacle. One problem is that the common blow molded or blow fill sealed containers are cost effectively manufactured with relatively this plastic wall sometimes down the thickness range of 0.025 inches or less and are generally made with a plastic materials such as high density polyethylene, polypropylene, polyvinyl chloride, or other like materials. Thin walled containers are commonly fabricated to reduce the plastic material mass (volume of plastic materials per unit) and hold down production costs and shipping weight. It is common practice of container manufacturing to consume the minimum amount of material used per unit to fabricate each container yet maintain user function for cost effective manufacturing purposes. Common container material durometers comprising containers having such ranges of this wall thickness I these like materials are hot generally strong enough to withstand the negative differential pressures of up to minus one atmosphere of negative pressure as commonly found in a vacuum/suction system without imploding or deforming. Product fluid enclosing distribution transfer containers are commonly fabricated using processes know by artisans skilled in the arts of blow molding or Continuous blow molding of open top containers and/or blow fill sealing of closed top containers as well as using such manufacturing processes such as thermal lamination of plastic sheet to form cavities/enclosures for the filling and production of intravenous solution containers and other parenteral containers and the like.

The solution to the problem of implosion and bottle/container deformity which occurs under high vacuum pressure is to connect to container to a suction collection system whereby container wall is interposed between its inner chamber and an outer space with each space subjected to a common amount of negative draw vacuum force/pressure. This force envelops itself inside and outside of the container which forms opposing differential pressures with provides enforcing balances by effecting a similar positive and negative neutralizing net force at the same time on the container wall eliminating negative implosion forces on the container wall. This is carried out by the container and canister of the instant case co-acting to contain waste and balance negative draw forces along the composite draw path. This addresses the issue of container deformity. This instant application discloses the neck of the pour bottle as the utilitarian area of the bottle for coupling with the lid of a canister system. The instant application discloses a throat aperture space (pour spout) of a plastic pour bottle as a utilitarian area for engagement of draw forces. The instant application discloses the throat space aperture, pour spout as a utilitarian area for coupling of a throat aperture plug. The instant application discloses a positive and negative exchange plug for providing communication between the draw force and the inside and outside of a fluid enclosing container. The instant application discloses locating an atmospheric pressure draw exchange at the neck of the container. The present application discloses interposing the container neck (pour spout) annularly between a plug and a lid for conversion coupling peripherally (not necessarily round). In an alternative embodiment container neck cap is interposed between a bottle and a container neck and a canister lid cover. In still a further embodiment, a boss projecting downward off of a canister lid is interpose peripherally between a container neck and a container neck negative atmospheric draw force exchange plug. The present application discloses fabricating a blow molded container for delivery transformation and conversion and bayonet coupling (push and twist) to a canister system. It is understood the invention is not intended to be limited to bottle neck configuration which are round. Any shaped bottle/neck shape lid/cover cap, plug, and boss configuration suitable for arrangement/construction having structuration to carry out the utility of the present invention may be fabricated and deployed to a carry out the utility of the instant case. The present invention discloses positioning the plastic container throat space in a negative pressure draw vacuum system whereby an in draw force is disposed to transfer and deposit medical waste material into the container and an outdraw force is disposed to transfer the differential draw forces. The embodiments of the instant case utilizes the inner chamber of a plastic pour bottle as part of the pressure vacuum draw path. The present case discloses several embodiments for carrying out the invention. In one embodiment the container cap is shown guiding the exchanging forces and positioned along a negative vacuum force draw path at a locating along a site of waste material (surgical site/patient site) and a source from which the draw force emanates. The cap is connectable to a lid cover which is attached to a canister body. In a second embodiment a bottle neck is peripherally (not necessarily meaning round) interposed between a lid and a throat space, the pressure exchanger, whereby in the throat space and is disposed in the guiding position which exchange forces along a draw path at a location between a site of waste material and the source of vacuum draw.

PURPOSE AND METHODS OF THE INVENTION

One object of the invention is to position a liquid transfer fluid enclosing container upstream to a patient delivery sequence, and then place the container downstream in connection with the flow of a waste material. Another object of the invention is to convert a liquid container affecting egress of the liquid and then the positioning of the container in flow confining connection downstream to a source of waste material. Another object of the invention is to pour solution from a container and then place the container downstream along a vacuum draw path in flow control connection with a suction wand. Another object of the invention liquid transfer container upstream to and in vascular access connection with a patient and then position the transfer container downstream in flow control composite connection with a vacuum draw path.

Another object of the invention is to provide supply chain efficiency whereby the dispensing container is also the receiving receptacle/container. Another object of the invention is to provide the waste reducing processes whereby the egress of the container upstream from a healthcare patient is the same container positioned downstream in flow control association with a negative atmospheric pressure draw force and flow confining connection with a suction wand. Another object of the invention is to provide practical steps for internal container handling including a) fabricating a transfer container, b) taking a transfer container and extending a draw path between a vacuum source and a suction wand, c) connecting a fluid enclosing delivery container to the path, d) depositing the waste material into the container. Another object of the invention is to provide methods and apparatus including a) enclosing a fluid in a container at manufacturing and transferring through distribution and administration for health care consumption, b) consuming at least a portion of the fluid product, c) converting the container into a vacuum collection system, d) removing the waste in the container e) disposing the waste. Another object of the invention includes a supply and disposal method comprising a) manufacturing a fluid enclosing container for the distribution, transfer and administration of a fluid product, b) consuming at least a portion of the liquid, c) directing a draw force to and from the container along a composite draw path, d) depositing waste material into the container.

Another object of the invention is to provide a method for reducing supplies comprising, a) providing a container fabricated for the delivery of a product, b) delivering the product, c) connecting the container to a vacuum source system, d) drawing waste material into the container, e) removing the waste material in the container, f) disposing of the waste material. Another object of the invention is to provide a method for reducing waste comprising a) transforming a waste receptacle from a container manufactured for enclosing and delivering a fluid, b) connecting the container to a composite waste draw conduit, c) depositing the waste material in the container, d) removing the container from the draw path, converting another delivery container into a waste receptacle comprising transformation of a fluid enclosing supply container into a waste collection receptacle. Another object of the invention includes providing the methods and apparatus for the transforming a plurality of supply containers into a plurality of waste containers. Another object of the invention is to enclose a plurality of supply containers having been transferred into a plurality of collection container within a single enclosure. Another object of the invention is to provide methods for transforming supplies into waste receptacles comprising a) constructing a fluid enclosing container, b) taking the container c) extending a draw path between a vacuum source and a suction wand d) connecting a delivery container to the path, e) depositing waste material into the container. Another object of the invention is to provide methods for deriving waste receptacles from supply containers including a) providing a liquid product in a selectively connectable waste receptacle b) disposing the receptacle in a vacuum collection container system, c) drawing a force along a composite draw path between a source of waste material and a vacuum source d) depositing waste in the delivery receptacle. An object of the instant case comprises positing a transfer container upstream in the flow of patient care sequence fro liquid dispensing and administration, b) positioning the container downstream in the flow of patient care in a material receiving and receptacle mode. Another object of the embodiments herein disclosed whereby the receptacle is positioned on the clean side of the supply and disposal chain for dispensing of it contents and the dispenser is position on the dirty side of the supply and disposal chain for receiving waste material as a receptacle, and this receptacle is in receiving structuration with a gravity flow system and or a composite vacuum draw path. Another object of the invention is to provide methods and apparatus for drawing a negative pressure within a transfer dispensing container. Another object of the invention is to provide methods for placing the container downstream to a flow control conduit depositing waste into the container under a positive push force, not a negative vacuum force. Another object of the invention is to provide methods and apparatus in structuration with a draw force including a) enclosing a fluid in a container at fabrication and providing the liquid product in a selectively connectable receptacle, b) disposing the receptacle in a vacuum collection canister system, drawing a force along a composite path along a source of waste, depositing the waste into a delivery receptacle. Another object of the embodiments herein disclosed is to provide connect ability to a transfer container and a vacuum canister collection lid. Another object of the invention is to provide a composite negative atmosphere draw path formed at least in part by the interior of a transfer container. Another object of the invention is to provide a draw force directed by a composite draw path in part co-acting to transform a delivery container to dispose waste material. Another object of the invention is to provide a canister in structuration with a fluid enclosing supply transfer container forming at least a portion of a composite draw path interposed between a vacuum source and a site of material waste. Another object of the invention is to combine in association with the novel features cited above, a negative draw path with a material flow path. Another object of the invention is to combine a draw path with the material draw path to dispose material in a transfer container to remove waste material from a site. Another object of the invention is to provide a throat aperture space/plug/seal disposed in a transfer container access/port site forming at least a part of the draw path controlling draw force to and from a transfer container. Another object of the invention is to provide a receptacle derived from a health care delivery sequence converted to co-act with a canister, a lid, a draw force, a composite path, a throat plug to dispose waste. Another aspect of the invention is to provide supply chain efficiency methods comprising a)

fabricating liquid enclosing delivery container, b) transferring the liquid to a delivery site, c) administering the liquid and connecting the container in structuration with a waste collection, d) collecting the waste. Another aspect of the invention is to provide supply chain efficiency methods comprising a) manufacturing a fluid enclosing container for the distribution of a liquid product b) distributing a liquid product, c) consuming at least a portion of the product d) directing a negative suction vacuum draw force to the container, e) connecting the container to a composite draw path having a suction wand at one end thereof, e) placing the suction wand in suctioning wand with waste material and drawing the waste material into the container, f) removing the material in the container, g) disposing the material. Another object of the invention is to a) fabricate a fluid enclosing delivery container for disposal and collection in a waste collection system. Another object of the invention is to provide a method of reducing waste comprising enclosing a fluid product in a fabricated delivery container, egressing the fluid from the container, and connecting the container along a vacuum draw path, drawing waste material into the container, removing the material for disposal, disposing the material. Another object of the invention is to provide a method of collecting supplies and transforming them into waste receptacles comprising a) collecting delivery supply containers, b) placing the containers positioned to receive waste in vacuum canisters, c) drawing vacuum, d) controlling the draw force to direct waste material for disposing waste in the transfer container. Another object of the invention is to provide a method of converting containers having dispensed at least some container contents, converting the container into a vacuum collection system receptive to waste collection and or removal and or disposal. Another object of the aforementioned objects is to provide a method of handling a dispenser and a receptacle wherein the dispenser is the receptacle. Another object of the invention is to provide a delivery collection container system using fluid enclosing bottle fabricated from a blow molding, and or a continuous blow molding process out of previously shaped polymer performs. Another object of the invention is to provide a delivery and collection container fabricated from a fluid enclosing blow fill seal manufacturing process container. Another object of the invention is to provide a suction/vacuum system which renders product distribution/transfer containers receptive to waste materials. Another object of the invention is to provide a collection system for reducing waste that is derived from product delivery. Another object of the invention is to reduce internal/external distribution, internal/external inventory management whether management is carried out by a vender management program or by a customer. Another object of the invention is for the consumer to account for the cubic volumes of incoming fluids and cubic volumes of outgoing waste materials for analysis and matching incoming and outgoing waste materials to the number of containers needed to optimize the supply purchasing process as practiced within the scope of the instant case. Another object of the invention is to provide methods and apparatus for sealing a vacuum draw path and for unsealing a vacuum draw path so that pour bottles, intravenous solution containers, and other types of containers may function to improve supply chain metrics relating to reducing inventory, labor, costs, shipping, and for reducing the overall mass of materials contributed to the waste stream. Another object of the invention is to provide convenient methods and apparatus for connecting and disconnecting a composite draw path utilizing in part at least one collection container derived from a supply chain matrix involving the commercialization of a fluent material, that but for this invention would ordinarily be utilized in such a way as not to confer ecological efficiency. Still a further object of the invention is to provide a lid handle such that movement of the handle in one direction causes a salability of a vacuum draw path between both a bottle and lid, and lid and canister. Still a further object of the invention is to provide a lid handle such that movement of the handle in the other direction causes an unseal ability of a vacuum draw path between both a bottle and lid, and lid and canister.

BRIEF DESCRIPTION OF THE DRAWINGS

FIG. 2 and FIG. 2a comprise an exploded view of FIG. 1.

FIG. 2 shows a top perspective view of a container 14, measuring stand 3 and container 2.

FIG. 2a shows lid 4 in its associated attaching components, handle thrust 6, lock 5, plug 7 spider 8, transfer hose 9, patient hose 11, vacuum hose 10, and cap 15.

FIG. 5a shows dual shot soft seal 4a3 as shown interposed in-between 4o of lid 4 and container flange 14g providing a seal there between.

FIG. 5b shows dual shot soft seal 4f interposed between plug 7 and the inside wall of throat (pour spout) of container 14 providing a seal there between.

FIG. 5c shows dual shot soft seal 4a2 interposed between lid 4 and canister 2 providing a seal there between.

FIG. 6 shows circles around container lid seal and shows a circle lid canister contact area.

FIG. 6a is a blow up of the sealing and contact area between lid 4 and canister rim 2.

FIG. 6b shows a detail of a connection of the connection between thrust 6 and lid 4 as well as the detail of the sealing area between lid. 4 and container 14.

FIG. 7 shows a container process whereby container 16 is processed into container 14 which is processes into to container 17 which is process into container 14. This comprises a disposal chain supply system which relates to FIGS. 19 through 19_of sheet 19 which show various stages of container utility.

FIG. 7a shows potential position of the sealing area between canister 2 and lid 4 defining space 4l having closing seal when thrust 6 is fully oriented clockwise.

FIG. 7*b* is a blow up detail showing sealing area between container 14 and lid 4 when thrust 6 is in its full clockwise position 6*w*.

FIG. 8 also shows a blow up detail of the relationship of lid 4 and canister 2 during thrust position 6*x*.

FIG. 8*a* shows a gap 4*l* between canister 2 and lid 4 as thrust 6 takes a counter clockwise orientation 6*x*.

FIG. 8*b* shows a detailed blowup of the unsealing relationship of container flange 14*g* and lid 4 as thrust 6 engages in a counter clockwise orientation 6*x*.

FIG. 9*a* shows the unsealing potential at dual shot soft seal 4*a*2 between canister 2 and lid 4 and depicts space 4*l* between lid 4 and canister 2 as becoming greater as thrust 6 takes a counter clockwise position 6*x*.

FIG. 9*b* shows a blow up detail of the unsealing area between container 14 and lid 4 at 4*k*. FIG. 9*b* also shows a blow up detail of the thrust 6 taking counter clockwise position 6*x*. Thrust thread 6*a* having lead, height and a pitch contacts container thread 14*d*. Counterclockwise orientation of 6*x* creates a thrust motion downward thrusting bottle 14 downward creating a counterforce provided by sealing friction at dual shot soft seal 4*a*3 and 4*a*2, said friction imparts a force counter force back through container 14 through thread 14*d* through thread 6*a* through thrust 6 which transfer said counterforce through thrust 6 through thrust bottom bearing 6*g* to bearing surface 4*a*9 of lid 4. This action counter action (effect cause effect) comprises and easy way for the separation of bottle 14 and lid 4 at sealing area 4*k* as well as canister 2 an lid 4 at sealing area gap 4*l*. Thrust 6 provides an easy to rotate smooth significant force giving a mechanical disassembly for the sealing and unsealing of a container lid and bottle.

FIG. 10*a* is a blow up detail jacking lever 21 flexed into a downward jacking position providing seal separation between canister 2 and lid 4.

FIG. 10*b* shows thrust 6 in an intermediate orientation between 6*x* and 6*w* defining a counter clockwise effect causing an effect of unsealing container 124 and lid 4 at 4*k*.

FIG. 11*a* shows the acting of jack lever keel 21*b* having contacted canister 2 at 2*b* after lever jack 21 has been flexed downward providing a mechanical leverage for the separation of lid 4 and canister 2.

FIG. 11*b* is a blow up detail of thrust 6*x* at an intermediate counterclockwise orientation 6*x* of FIG. 10 *b* further defining a process of thrust effect and counter effect describing the vertical thrust forces moving the container 14 down relative to lid 4 and unsealing the lid and bottle at 4*k*.

FIG. 14 *a* shows a blow up detail of the leverage jack making contact with container 2.

FIG. 14*b* shows thrust bearing 6 in a full clockwise orientation.

FIG. 15 *a* shows a cross section of lid 4 taken at one of two perpendicular sections that would show one of four locks 5 in an up unlocked position and one of four locks 5 locked in a downward locked position.

FIG. 15*b* shows a blow up detail of lock 5 up in the unlocked position and spring lock 4*r* in its unlocked/unengaged resting position.

FIG. 15*c* shows one of four locks 5 in a downward locked position showing lock push ramp 5*c* having moved the end of spring lock 4*r* into an interference locked position under canister lip 2*f*.

FIG. 17*a* is a blow up detail of lack 5.

FIG. 17*b* is a blow up detail of thrust bearing 6.

FIG. 17 *c* is a blow up detail of thrust bearing retaining hook 4*f* of lid 4 and thrust handle surface 4*a*9 if lid 4.

FIG. 17*d* is a blow up detail of jacking lever 21.

FIG. 18*a* shows a side elevation view of a container depicting its height and a dimension showing its thread.

FIG. 18*b* shows another container size depicting g its height and depicting a dimensions from its top to the sealing area.

FIG. 18*c* shows a side elevation view of an alternative bottle size showing a dimension of its height and a dimension of its center to its flat side wall.

FIG. 18*d* is a side elevation cross section of the assembly of canister 2 and measuring stand 3 showing a dimension of bottle of said stand to the bottom so stand bottle slot showing a dimension of subassembly center line to inside wall of said bottle slot and showing a dimension of sealing rim canister 2 and a bottle thread height as further depicted in FIGS. 18*e*, 18*f*, and 18*g*.

FIG. 18 *e* shows a side elevation view showing measuring stand 3 in two parts, 3*a* and 3*b*. A large container, a dimension between the bottom of stand 3 and the bottom of bottle slot a dimension showing the center of the sub assembly and the inside of bottle support stand and a dimension showing ht top of the bottle to the bottle flange seal 14g.

FIG. 18f is similar to the FIG. 18e but showing an alternative container size.

FIG. 18g is similar to FIGS. 18e and 18f showing an alternative container size. It is important to note that thread height 14j of FIG. 18a dimension 14q of FIG. 18b dimension 14o of FIG. 18c dimensions 14t of FIG. 18d, e f, & g, and dimension 3u of FIGS. 18 e, f, & g as well as dimension14s of FIGS. 18 a, b, & c all correspond to matching a thread having a thread height, a thread having a thread pitch, a thread having a thrust lead to thrust handle such as 6 shown in FIG. 16 and other figures of the instant case such that a single thread or a common thread of an extremely high volume containers made in various volumetric cubic capacities, such as 14, 14a, 14b, 14c, etc., may all be functionally coated into a collection system designed for supply chain efficiency such that XX-nut dimension and XX-bottle of FIG. 15 as well as the assembly contact points of z. x. and the alignment assemblies aided by leads 4g, 4h, 3w, 14v, 14g, all provide horizontal and vertical alignment system that is easy to assemble such that thrust thread 6a and bottle thread 14d properly engage without undo attention.

FIG. 19a depicts a container which has been hermetically sealed enclosing so sterile/other liquid 16B.

FIG. 19b shows an empty container is sequence waiting to be placed into the canister system of the preferred embodiment (the apparatus of FIG. 19 with its cap having just been removed.

FIG. 19c shows lid 4 removed from the subassembly of the preferred embodiment.

FIG. 24 shows a lid positioned above a canister 2' with pour bottle 14' positioned to seal said lid 4' against said canister 2'.

FIG. 24a is a close up view depicted in the small circle of FIG. 24. This view shows a close up of the thrust handle 6' after it has been snap assembled into the retaining hook thrust stops of lid 4'.

FIG. 26a is a close up view of the small reference circle of FIG. 26. In FIG. 26a, a gap is shown being caused by thrust contact between bottle neck threads 14' and thrust handle 6' threads.

FIG. 26b is a close up view of the interface between lid 4' and thrust handle 6' as the threads from bottle 14' have made contact with thrust handle threads.

FIG. 28a is a close up view of a small reference circle of FIG. 28.

FIG. 28a is a close up view of the seal of o-ring 24' and o-ring 23' which is allowed by the thrust handle 6' having been moved in the direction aaa'.

FIG. 28b shows the relationship between lid 4' and thrust handle 6' as thrust handle 6' has been rotated in the aaa' direction.

FIG. 30a is a close up view of the small reference circle of FIG. 30. FIG. 30a shows o-ring 24' and o-ring 23'.

FIG. 30b shows a relationship between thrust handle 6' and lid 4' defining an push interference thrust feature, when thrust handle 6' is rotated in the bbb' direction at a point prior to the separation of the seal between the lid 4' and canister 2' at O-ring seals 24' and 23' and separation of bottle 14 from lid 4'.

FIG. 32a is a close up view of pour bottle 14' preassembled to lid 4', thrust handle 6' having been rotated indirection aaa' causing thrust contact between pour bottle flange 14e' and o-ring seal 22' forming a seal between pour bottle 14' and lid 4'.

FIG. 34a is an isometric close up view of thrust handle 6'.

DETAILED DESCRIPTION OF THE DRAWINGS

Figure 1:
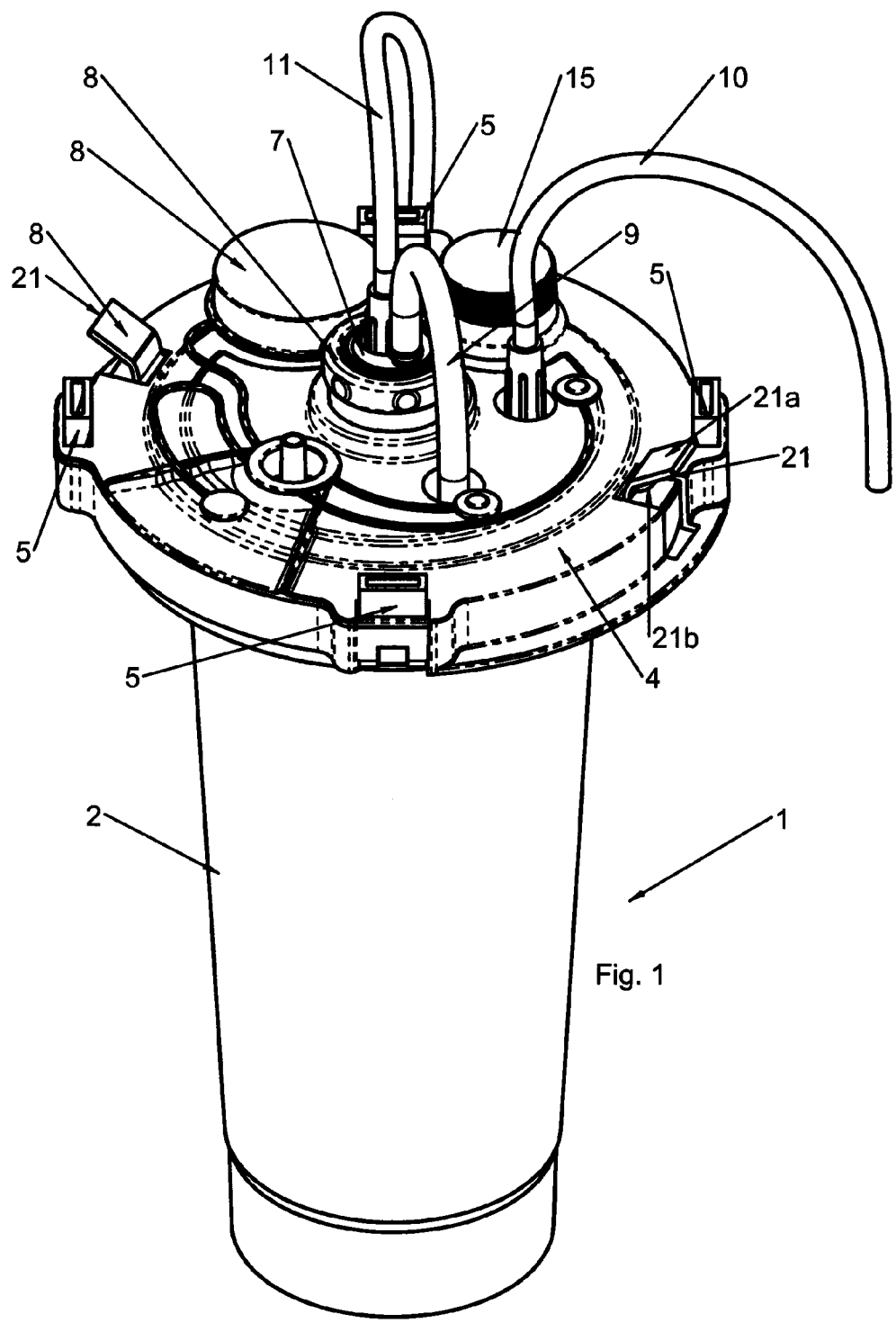
FIG. 1 is a top perspective view of a disposal chain supply system.

FIG. 1 is a top perspective view showing the system of the preferred embodiment 1, canister body 2, lid 4, four locks 5, thrust handle 6, plug 7, spider cap 8, transfer hose 9, vacuum transfer hose 10, patient hose 11, leveraging jack 21, and pressure surface 21a of leveraging jack 21.

Figure 2:
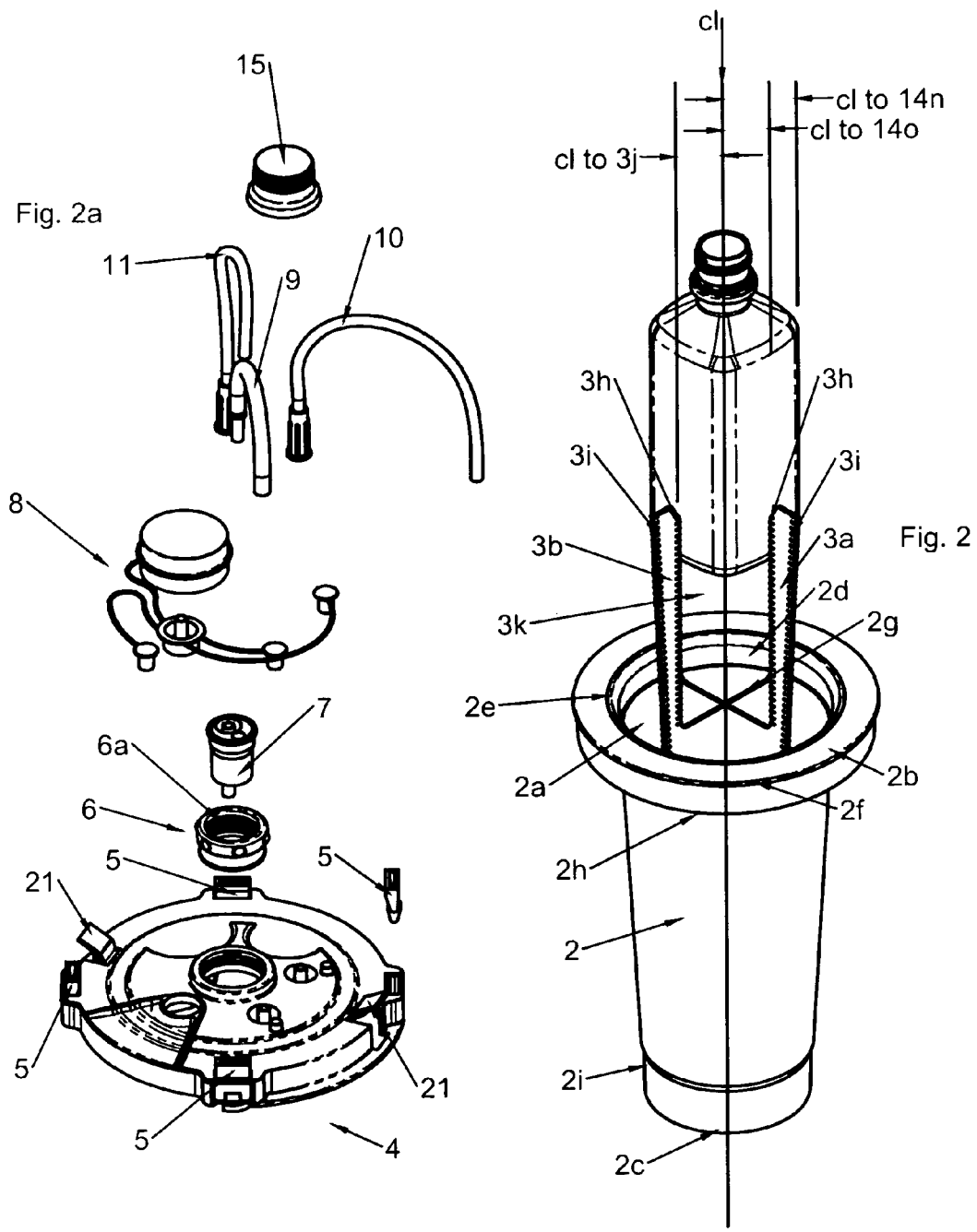

FIGS. 2 and 2a is an exploded view of the system in two parts. Referring to FIG. 2 specifically, showing a centerline of the exploded assembly vertically up and down the center of the parts. Canister body two is shown with base 2c, stack rim 21, interference lip 2f, contact surface 2b, main housing body 2, carrying rim 2h, inner housing space 2a, horizontal top surface seal 2e, and angled inner surface seal 2d. Also shown is measuring stand 3, featuring cutout card 3a and cutout card 3b, one of which is manufactured with a slot so the two cards may be assembled perpendicular to each other so that they nest into inside of canister 2. Measuring indicia 3h is shown which has incremental volume measurement markings relative to fluid collecting into container 14 and incremental volume measurement markings 31 relative to fluid collecting which may be collected in an overflow from container 14 and into canister 2. It is important to note the inside distance from centerline to 3j, the inside edge of the measurement stand post as well as to the measuring distance from the centerline from 14n the corner of container 14.

Referring to FIG. 2a showing cap 15 of container 14, patient hose 11, vacuum transfer hose 9, vacuum source hose 10, spider cap 8, plug 7, handle thrust 6 having inside thread 6a, one of four locks 5, an jacking lever 21.

Figure 3:
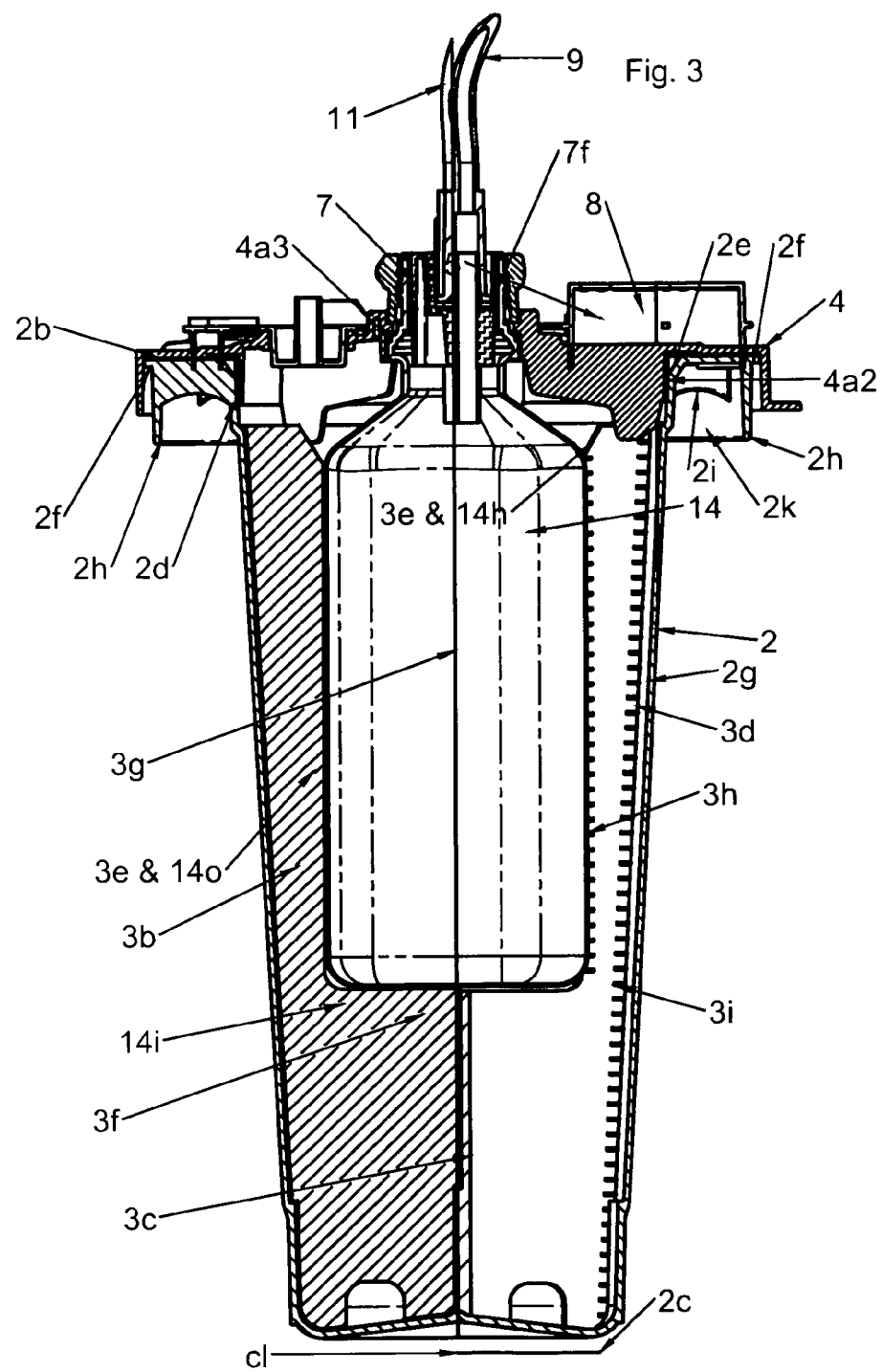
FIG. 3 is a cross section of the embodiment show in FIG. 3 showing 3 blow up circles to illustrate the location of dual shot soft seals. The Embodiment of FIG. 4 has a break at an intermediate portion along the canister and measurement stand.

FIG. 3 shows a cross section of component parts in their assembled position. Shown is patient hose 11, vacuum hose transfer hose 9, plug 7, dual shot plug soft seal 7f, spider cap 8, dual shot soft seal 4a3, dual shot soft seal 4a2, canister lock interference lip 2f, lock 5, contact surface 2b of canister 2, canister carrying rim 2h, canister rim support struts 2i, canister finger curl space 2k. Container 14 sealed to lid 4 by tradable engagement using handle thrust 6. Measurement card 3a and 3b are seen nested with canister 2 and are supporting container 14. Canister 2 sits on its stable base at 2c.

Figure 4:
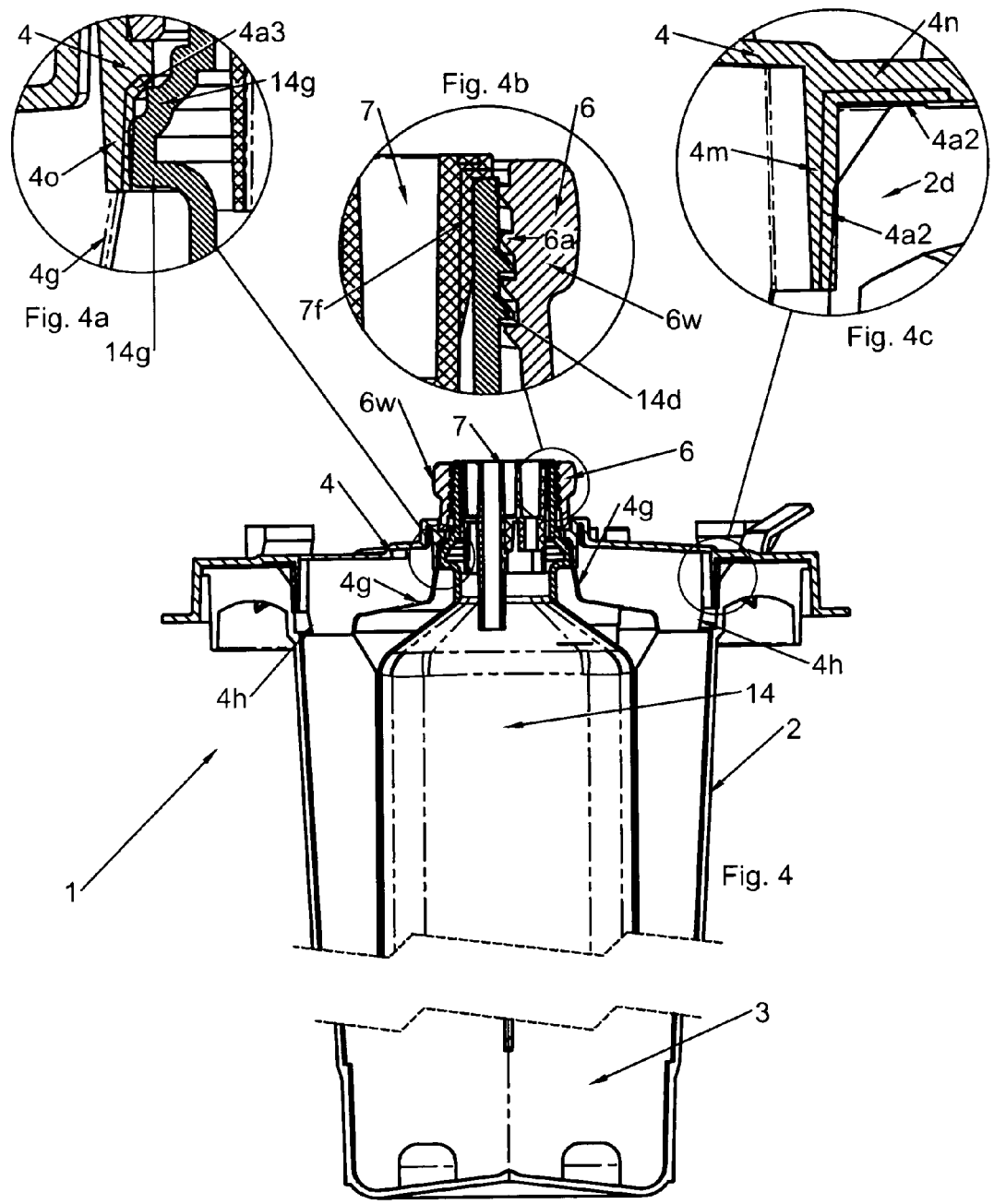
FIG. 4a shows a blow up of a dual shot soft seal 4a3 attached to lid 4 at 4o during molding of lid 4.
FIG. 4b shows dual shot soft seal 7f attached to plug 7 and it is affixed to plug 7 during molding of plug 7.
FIG. 4c shows dual shot soft seal 4a2 attached to lid 4 along surface shown at 4n and surface 4m.

FIG. 4 shows a cross section of system 1 with canister 2 measuring stand, cards 3a and 3b and bottle 14 cutaways. Lid 4 shows assembly bevel leads 4h and 4g which are associated with a plurality of strut support wall sections extending downwardly from the main level of lid 4. Bottle 14 is thread ably engaged handle thrust 6 with handle thrust 6 fully clockwise oriented 6w if a fully sealable position.

FIG. 4a is a blow up showing the seal between bottle 14 and lid 4. Bottle flange 14g engages dual shot 4a3 of lid 4. Dual shot 4a3 is molded into lid 4 at 4o.

FIG. 4b is a close up detail showing the dual shot seal interposed between plug 7 and the throat of canister 14. Also shown is bottle thread 14d engaged with handle thrust thread 6a. Handle thrust 6 is shown in a full clockwise orientation 6w. This view also depicts showing a cross section of interposing a soft dual shot seal between plug 7 and bottle neck 14 peripherally. This view also depicts showing interposing the neck of bottle 14 between a plug 7 and a handle thrust 6.

FIG. 4c shows a blow up of a cross section showing the interposing a soft dual shot 4a3 between lid 4 and canister 2. Dual shot 4a2 is molded into lid 4 during molding of lid4 and provides a seal horizontally at 4n and substantially angularly at 4m of lid 4.

Figure 5:
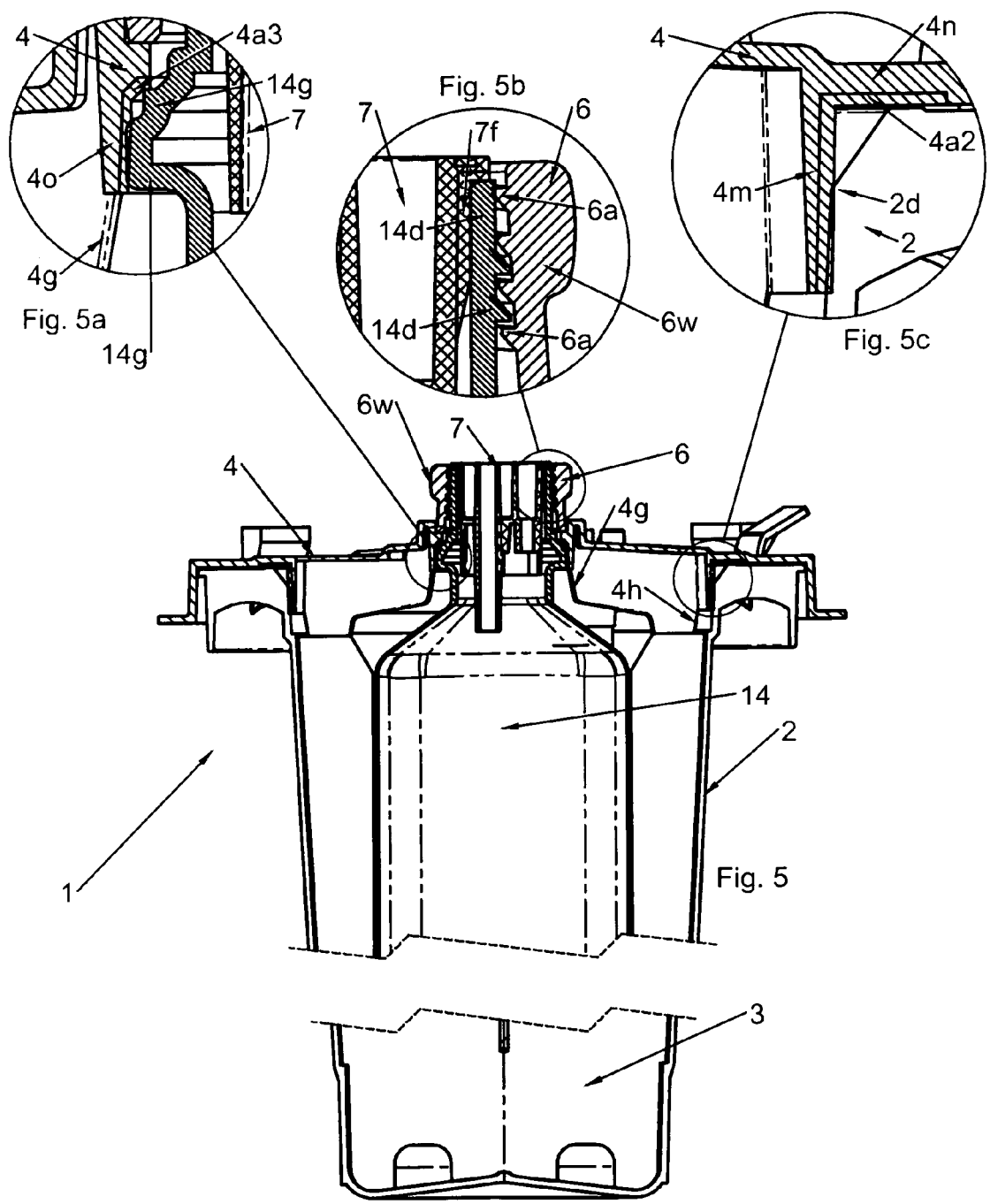
FIG. 5 show a cross section of embodiment show in FIG. 4 depicting the relationship of the three seals described in FIGS. 4, 4a, 4b and 4c. When thrust 6 is rotated clockwise to its endpoint the three said seals and associated mating and sealing surfaces and components are show sealed in the above three blow up figures.

FIG. 5 is a cross section of system 1, showing measurement stand 3, canister 2, bottle 14, lead bevel 4h of lid 4, lead bevel 4g of lid 4, lid 4, plug 7 handle thrust 6 and 6w depicting the handle thrust 6 fully orientated clockwise fully forming a seal between bottle 14 an lid 4.

FIG. 5 a shows a blow up detail of dual shot 4a3 as handle thrust 6. FIG. 5 is rotated clockwise as bottle flange 14g is increasing engages lid at 4o notably as a result of slight draft angle lead 4o.

FIG. 5b show plug 7 soft dual shot seal 7f, bottle thread 14d, handle thrust thread 6a all being respectfully oriented in full counterclockwise orientation.

FIG. 5c shows a blow up detail of soft dual shot 4a2 interposed between lid 4 and canister 2 at horizontal 4n and substantially vertically angled surface 4m of lid 4.

Figure 6:
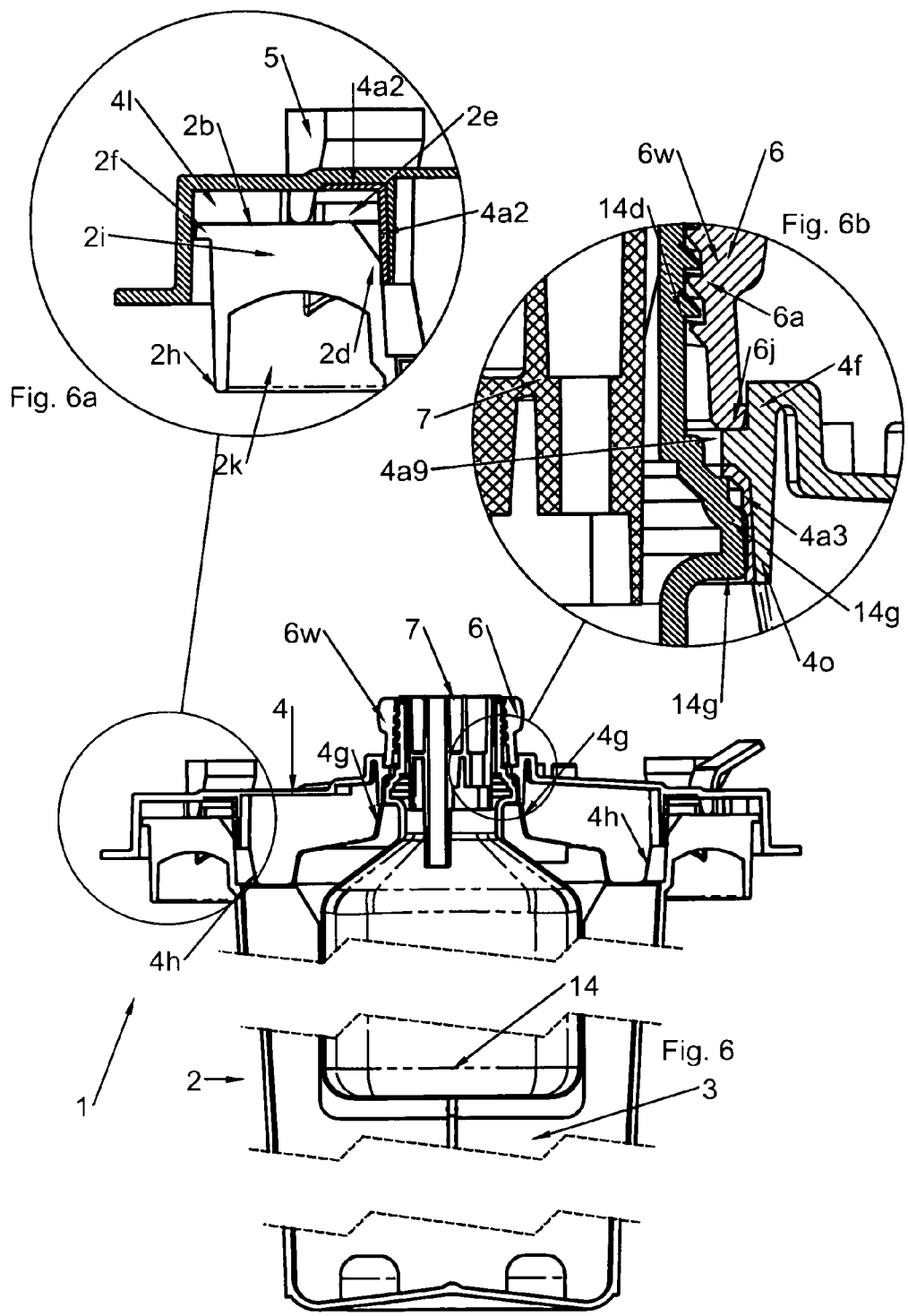
FIG. 6 is a cross section as shown in FIGS. 4 & 5 showing two breaks along the area of canister body 2.

FIG. 6 shows a cross section of FIG. 1 having 2 breaks along the vertical rise of canister 2, bottle 14, measurement stand 3 as well as a lower break across canister 2 and measurement stand 3. This view shows lid 4 having two lead bevels 4g and 4h, handle thrust 6, plug 7 and 6w depicting handle thrust 6 in a fully clockwise bottle/lid sealing orientation.

FIG. 6a is a blow up showing finger curl lifting/carrying space 2k of canister 2, lower canister rim 2h, rim strut supports 2i, substantially vertically angles canister seal surface 2d, substantially horizontal canister seal surface 2a, soft dual shot seal 4a2, horizontal and vertical 4a2, lock 5 in an up unlocked position, contact surface 2b of canister 2, separability space 4*l* showing separation between canister 2 and lid 4, and interference lock lip 2*f* of canister 2.

Figure 7:
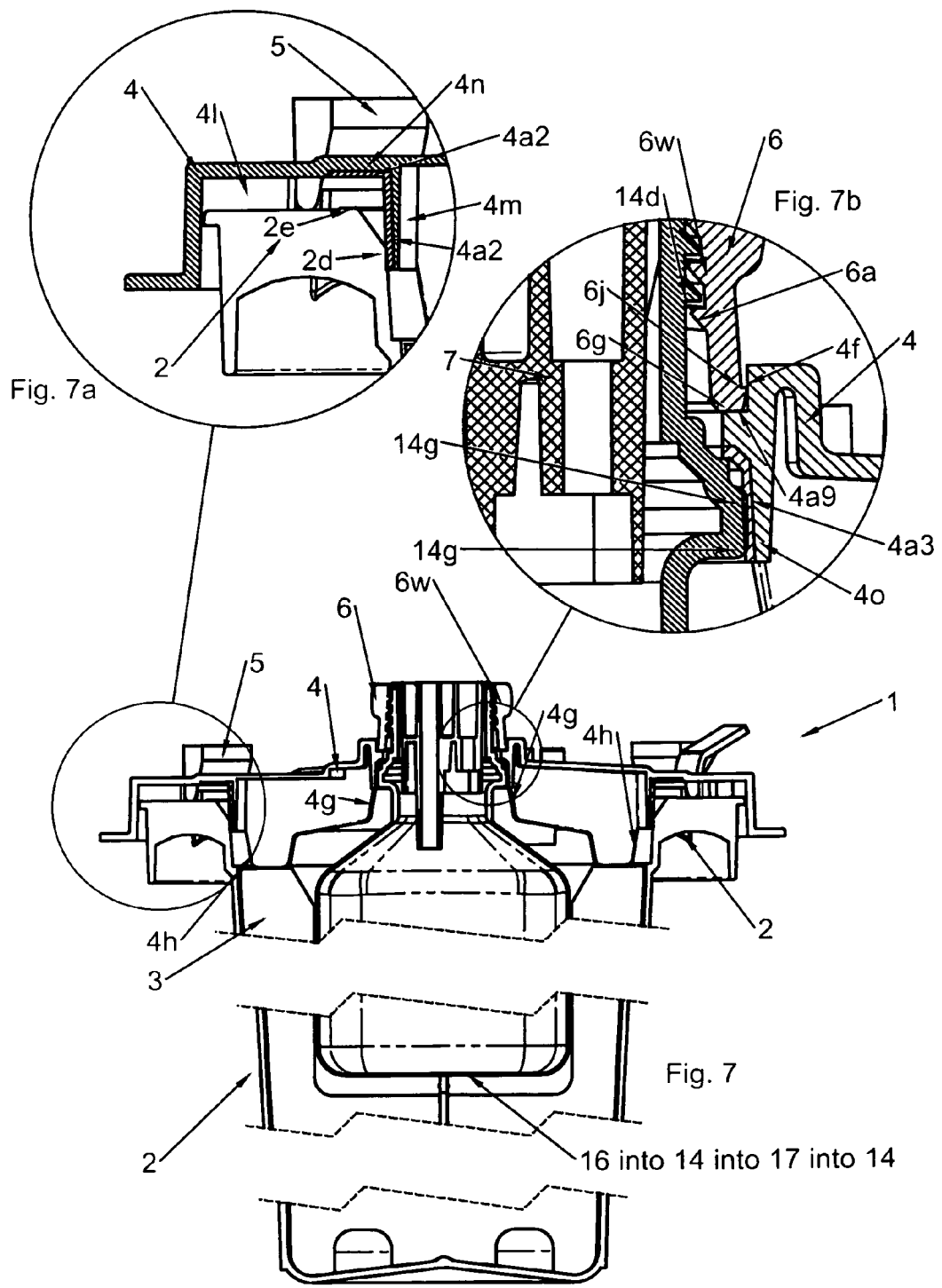
FIG. 7 is a cross section of the embodiments of FIGS. 4, 5 & 6 showing two breaks along the canister body and having circles around the container lid sealing area and the lid canister sealing area.

FIG. 6*b* shows a blow up detail depicting bottle flange 14*g* plug 7, soft dual shot bottle/lid weal 4*a*3 thrust handle bearing portinsurface 4*a*9, thrust handle retaining hook 4*f* of lid 4, thrust handle hook 6*j*, thrust handle thread 6*a*, thrust handle 6, and 6*w* depicting the thrust handle in full clockwise sealing orientation FIG. 7 depicts a cross section of system 1 depicting canister 2 and stand section card 3. This shows two breaks along the vertical rise of canister 2, card measurement stand 3, bottle 14 as well as a lower break across canister two and measurement stand 3. This view shows canister assembly bevel lead 4*h* and bottle assemble bevel lead 4*g*, one of four locks 5, lid 4, thrust handle 6. FIG. 7*a* is a blow up detail defining separability space 4*l* defining separation between canisters 2 an lid 4. Horizontal canister sealing surface 2*e* and substantially vertical canister sealing surface 2*d*, dual shot soft seal 4*a*2, substantially horizontal and vertical dual shot soft seal 4*a*2, at 4*n* and 4*m* of lid 4 and one of four locks 5 show up in unlocked orientation.

FIG. 7*b* depicts handle thrust 6 in its full clockwise sealing orientation as depicted by 6*w* showing the engagement of bottle thread 14*d* and handle thrust thread 6*a*. As handle thrust 6 takes its clockwise sealing orientation thrust bottom 6*g* contacts handle thrust bearing surface at 4*a*9 to the extent a light amount of friction resistance occurs as bottle flange 14*g* moves upwardly along soft dual shot seal 4*a*3 which is interposed between lid 4 and at 4*o* and bottle flange 14*g*.

Figure 8:
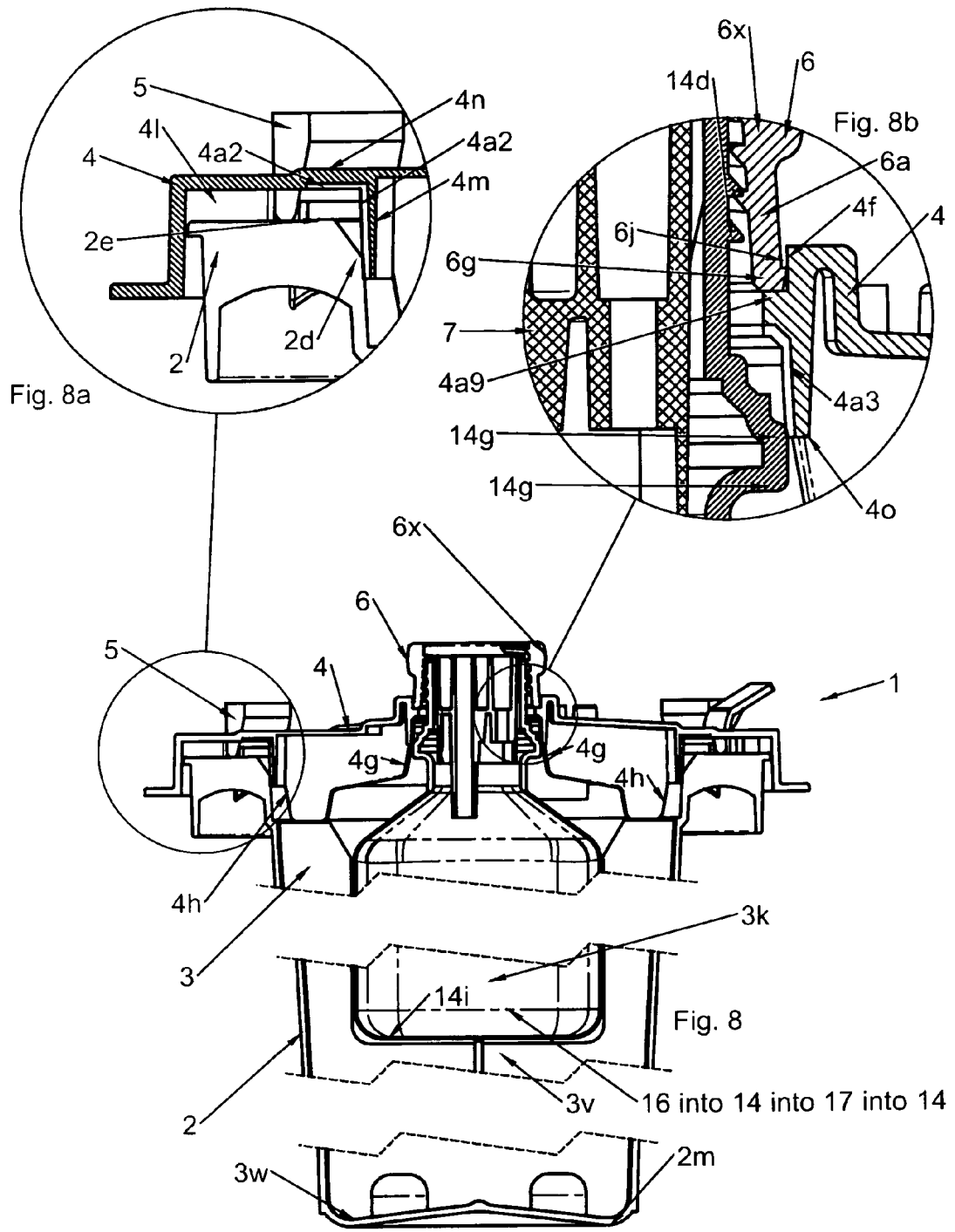
FIG. 8 is a cross section of the preferred embodiment showing detailed blow up circles of thrust 6*x* as it may be engaged in counter clockwise unsealing orientation.

FIG. 8 is a cross section view of the preferred embodiment 1 having two breaks along the vertical rise of canister 2 and measurement stand 3, and also across bottle 14. Indicia on this sheet shows a utility cycle of disposal chain supply systems container and fluid management as it relates to sheet 19 of 23. Sixteen depicting a hermetically sealed bottle, which becomes empty into bottle 14, which becomes inserted into a canister system which becomes a supply bottle having surgical suction waste, disposed therein which become 14, another empty bottle after fluid disposal. Also shown is canister bottom 2*m*, measurement stand bottom 3*w* canister 2, bottle slot bottom 3*b*, bottle bottom 14*i*, assembly canister lead 14*h*, assembly canister lead 4*h*, and bottle canister lead 4*g*, one of four locks 5, in an unlocked position, lid 4, handle thrust 6, and 6*x* depicting handle thrust having been rotated clockwise in a unsealing orientation.

FIG. 8*a* is a blow up detail of the effects of handle thrust orientation 6*x* in that separability space 4*l* is enlarged by counterclockwise unsealing orientation of handle thrust 6, also depicted is canister 2, canister sealing surface 2*d* and 2*a* associated with horizontally substantially vertically angled soft duals hot seal 4*a*2 of lid 4 at 4*n* and 4*m*.

FIG. 8*b* is a close up detail of the bottle lid and sealing orientation, 6*x* of handle thrust 6 during counterclockwise unsealing orientation 6*x* of thrust 6, container thread 14*d* is engaged by handle thrust 6*a* initiating a downward motion on container 14 effecting contact of thrust rim 6*j* upon lid hook 4*f* of lid 4, similarly causing container flange 14*g* to move downwardly unsealing from soft dual shot 4*a*3 and unseal ably engaging 4*o* of lid 4.

Figure 9:
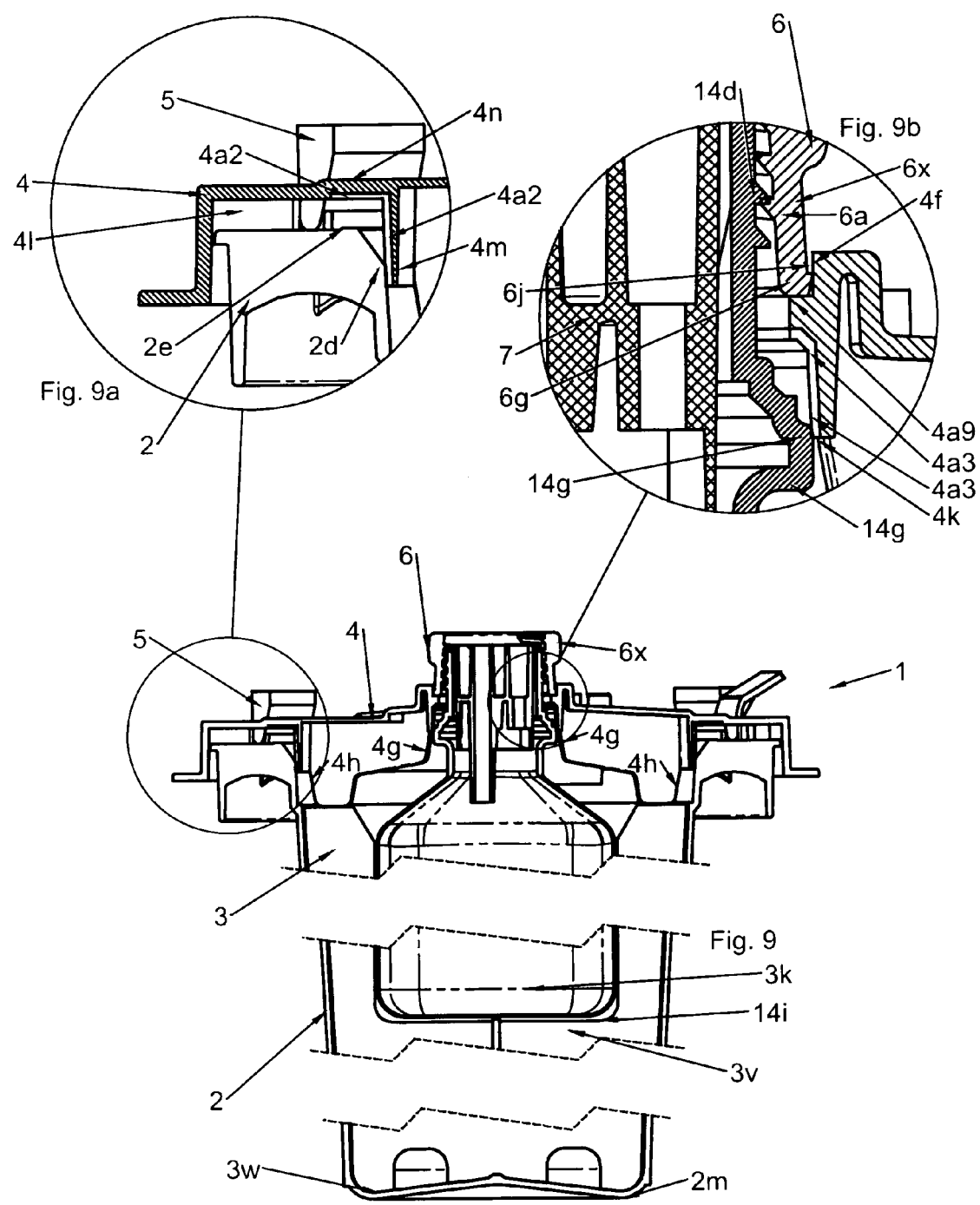
FIG. 9 shows a cross section of the preferred embodiment having two breaks along the canister body.

FIG. 9 is a cross sectional view of the preferred embodiment 1 showing canister base 2*m*, measurement stand base 3*w*, measurement stand bottle slot bottom 3*b* canister 2 measurement stand 3, bottle bottom 14*i* handle thrust 6 in counterclockwise unsealing orientation 6*x*. Also show is lid 4, and lock 5 in and upward unlocked position.

FIG. 9*a* is a respectively the same figures as shown in FIG. 8*a*. Shown in FIG. 9*a* is container flange 14*g*, unsealing from sealing space 4*k*, disengaging duals shot soft seal 4*a*3. As handle thrust 6 is moved counterclockwise unsealing orientation 6*x* further producing and upward force, 65*j* continuing as bottle flange 14*g* drops below sealing space 4*k*. As bottle thread 14*d* continues to engage handle thrust thread 6*a* even thought bottle sealing flange 14*g* is completely disengaged with soft dual shot seal 4*a*3, handle thrust 6 continues its counterclockwise orientation of unsealing. We must refer back to FIG. 9 which shows a further downward motion of container 14 enacting contact force between bottle bottom 14*i* and measurement stand sot bottom 3*b*, further enacting force between measurement stand bottom 3*m* and canister at 2*m* continually moving the bottle down further enacting an unsealing force increasing separability space 4*l* and unsealing lid from canister 2 at dual shot seal 4*a*2. and as the counterclockwise handle thrust 6 xs continually unseals the bottle 14 and the lid 4 and the lid 4 form canister 2.

Figure 10:
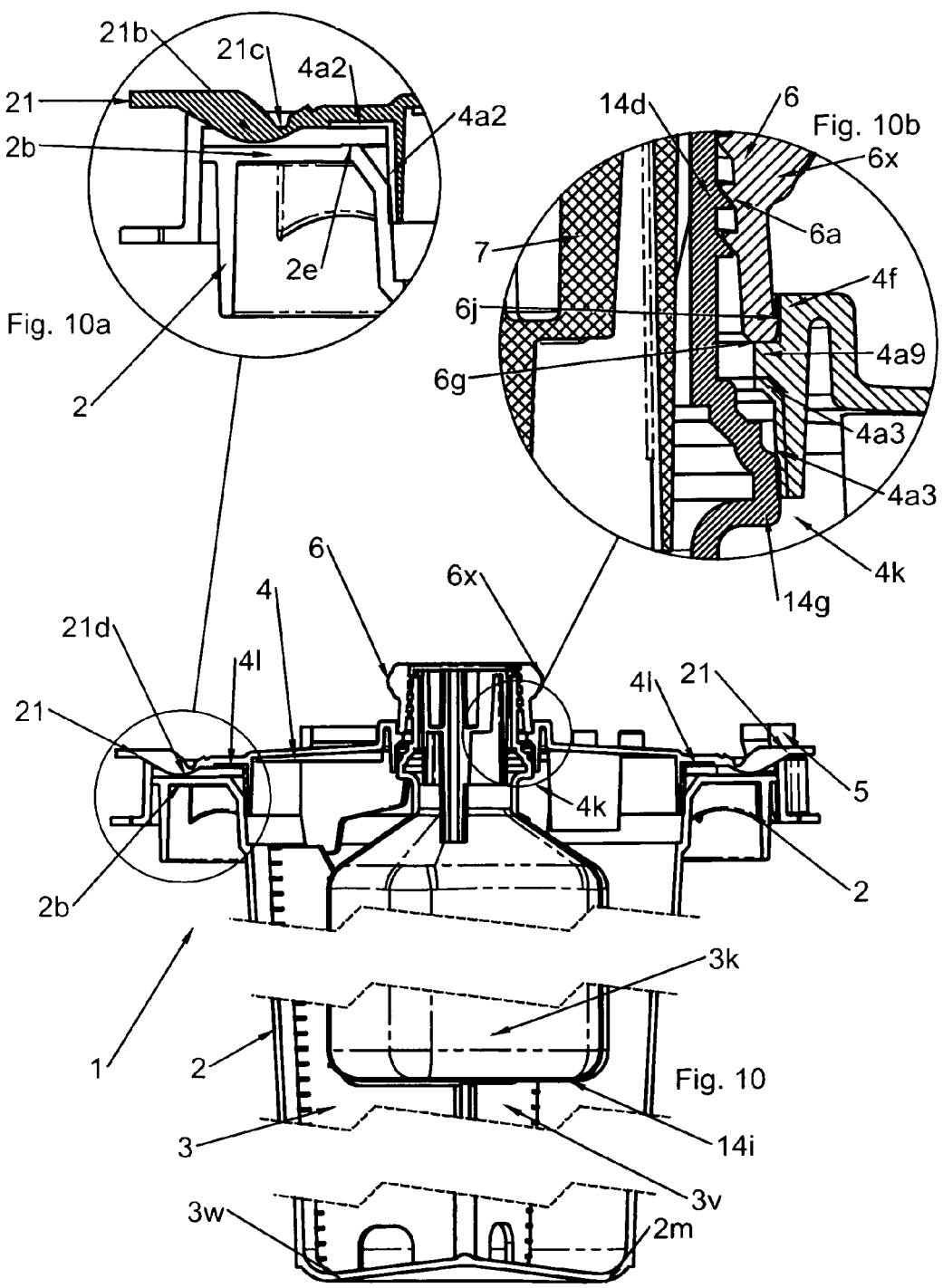
FIG. 10 shows the preferred embodiment showing circles of detail blow up thrust 6*x* in a thrust position intermediate to that as show in Figure on sheet 4 and sheet 5 and sheet 6 and sheet 7 and sheet 12 with respect to the thrust position shown in sheets 8 and sheets 9.

FIG. 10 shows substantially similar cross section view as shown in FIGS. 6, 7, 8, and 9, however handle thrust 6 is taken and intermediate unsealing/sealing orientation as well as jacking lever 21 is shown flexed down whereby push off keel 21*b* of jacking lever 21 makes contact with canister contact surface 2*b* further increasing separability space 4*l*.

FIG. 10*a* is a blow up detail of jacking lever 21 having been flexed at flexion detent 21*c* such that push off contact keel 12*b* makes contact with canister 2 at contact surface 2*b* causing further separation between lid 4 and canister 2 at dual shot soft seal 4*a*2.

FIG. 10*b* depicts handle thrust 6 in an intermediate counter clockwise unsealing orientation depicting container flange 14*g* in a partial disengaged and unsealed orientation with respect to dual shot soft seal 4*a*3 at sealing space 4*k*, during unsealing counterclockwise orientation 6*x* of thrust lever 6 unsealing friction at sealing area 4*k* between container flange 14*g* and dual shot soft seal 4*a*3 creates a counter upward force effect back through bottle neck 14*d*, engaging thread 6*a*, such that handle thrust hook rim 6*j* exerts an upward producing motion and force on lid retaining hook 4*f* of lid4.

Figure 11:
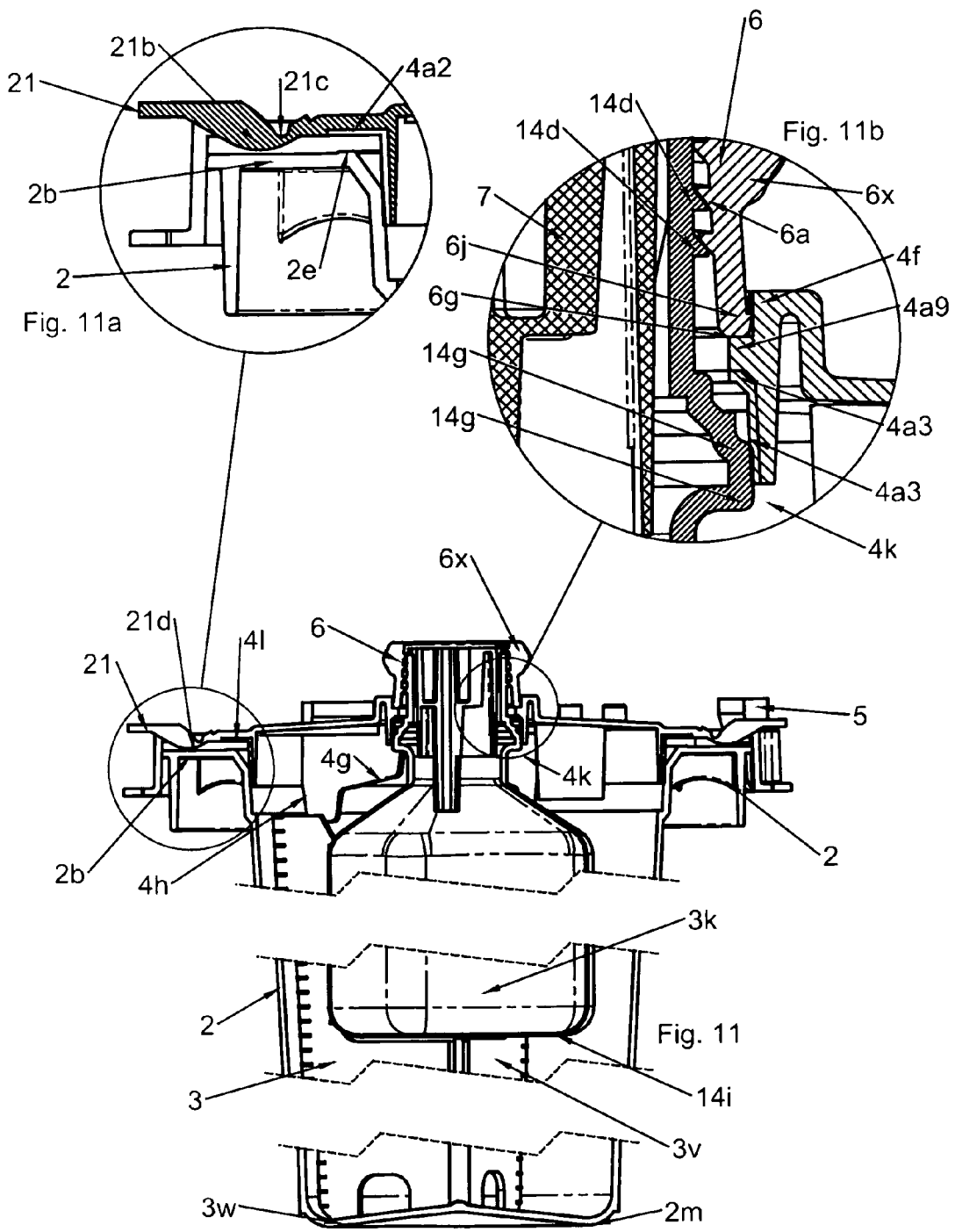
FIG. 11 shows the preferred embodiment of FIG. 10.

FIG. 11 shows a substantially similar cross section of the preferred embodiment as shown in FIG. 10.

FIG. 11*a* shows substantially similarly positioned leverage jack 21 having been flexed downward at 21*c* allowing push off contact keel 21*b* to make contact with canister contact surface 2*b*. Also shown is figure lift rim 4*a* and in this scenario would place a thumb on jacking leverage 21 and place the finger underneath finger lift rim 4*u* of canister lid 4 in opposing digital fashion allowing the facilitation of separation of lid 4 and canister 2.

Figure 20:
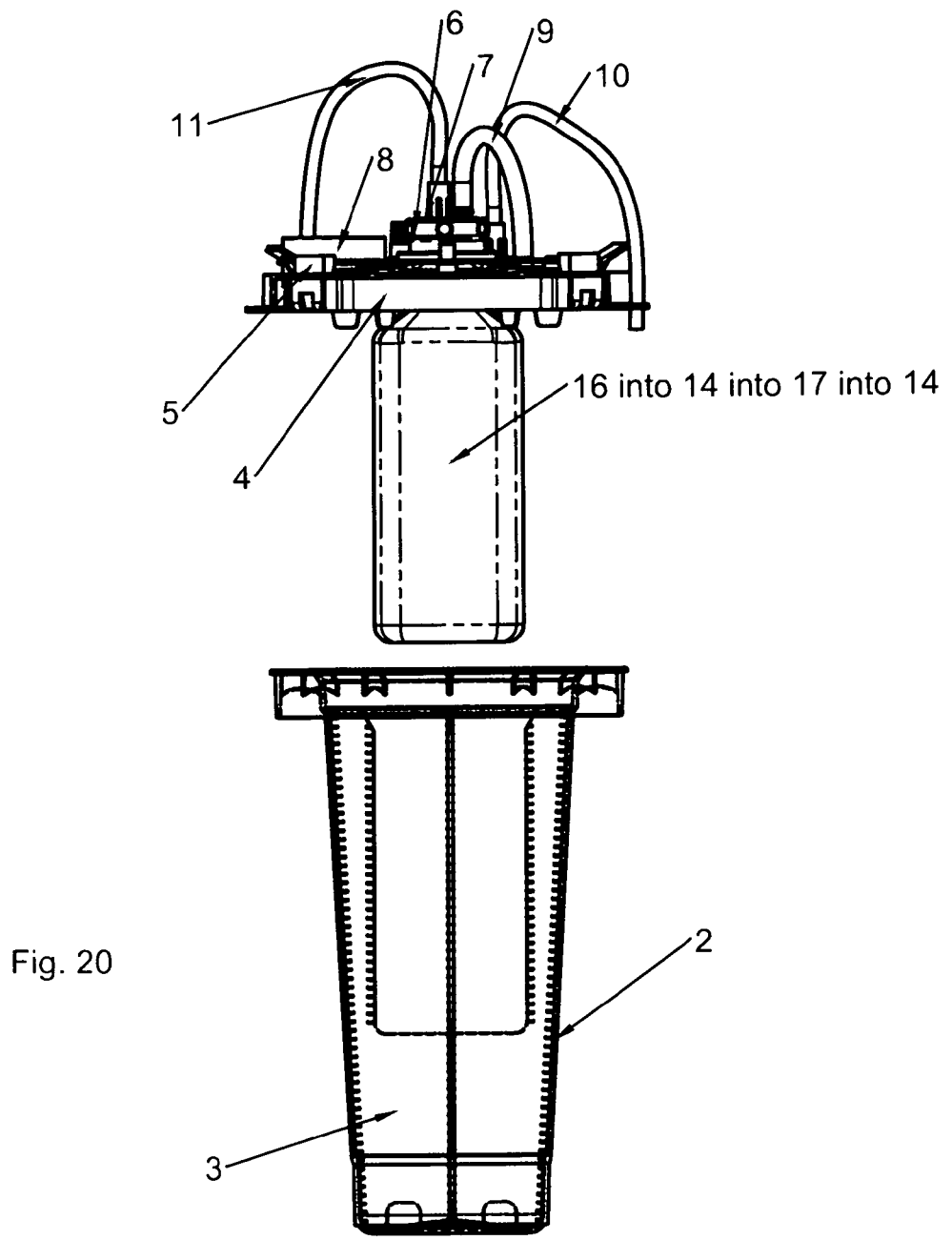
FIG. 20 shows an alternative means of separating the container s lid 4 subassembly from canister 2 and measuring stand 3.

FIG. 11*b* shows the relationship between the bottle 14 and lid 4 in similar handle thrust orientation 6*x* as shown tin FIG. 10*b*. This figure depicts the positional disassembly option of the system is that the leverage jack 21 may be pushed down so that contact keel 21*b* will push off canister 2 at 2*b* creating an upwardly jacking motion while finger lift rim 4*u* provides a lifting surface for opposing finger action for the disassembly between lid 4 assembly and canister 2. As illustrated in FIG. 20 of sheet 23.

Figure 12:
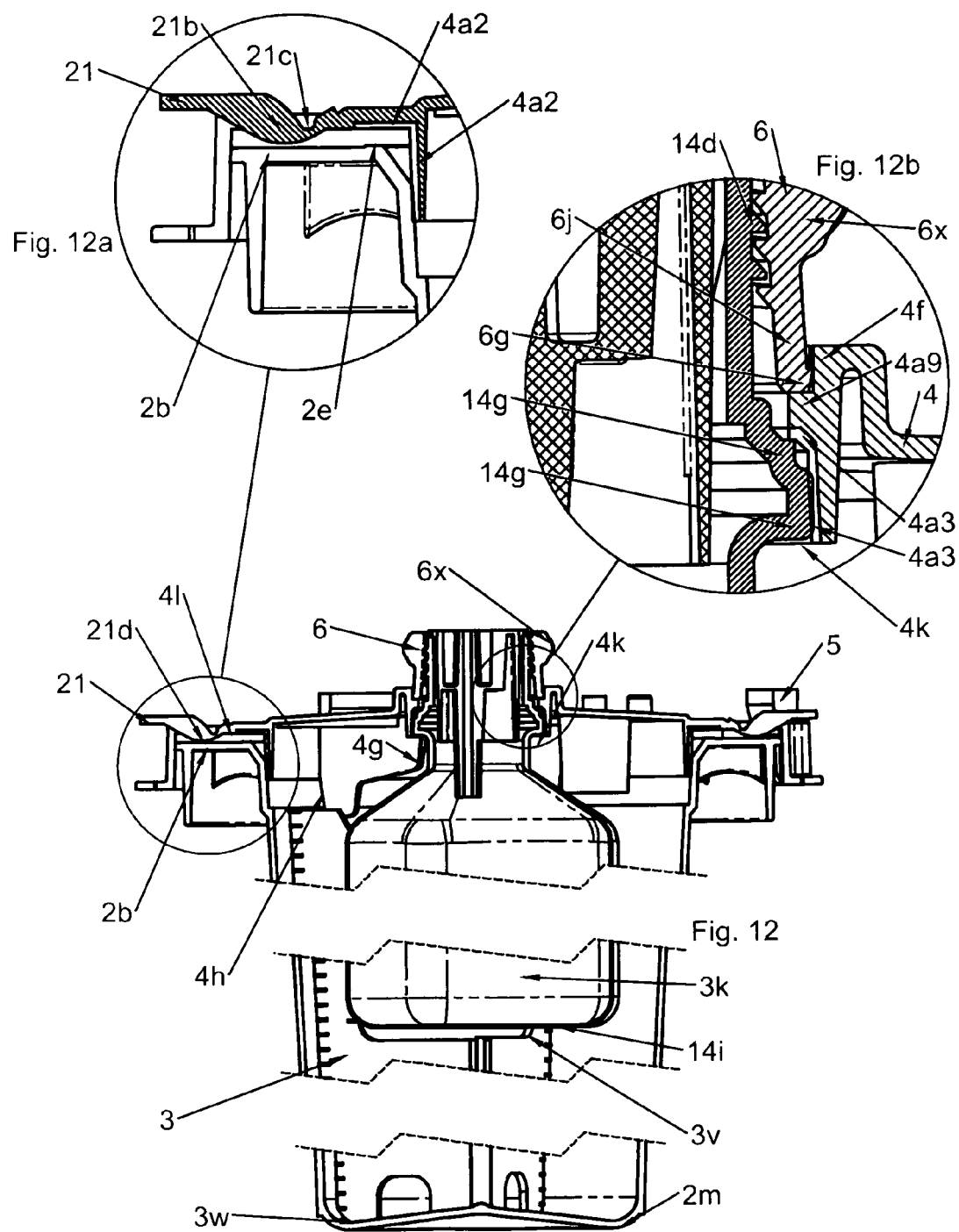
FIG. 12 is a cross section of the preferred embodiment defining blow ups of seal area 4*k* and jacking lever 21.

FIG. 12 shows a similarly oriented cross section of the preferred embodiment showing bottle 14 and lid 4 in full sealing orientation by the full clockwise orientation of 6*x* of handle thrust 6 and is noted here that a slight gap exists between container bottom 14*i* and measurement stand slot bottom 3*v*. This gap may also be achieved by downward thumb pressure on jacking lever 21 and upward finger lifting of finger rim lift 4*u*.

FIG. 12a shows similar orientation of jack lever 21 making contact with contact surface 2b canister 2, by push off contact keel 21b.

FIG. 21b shows substantially the same blow up detail as that of FIG. 7b.

Figure 13:
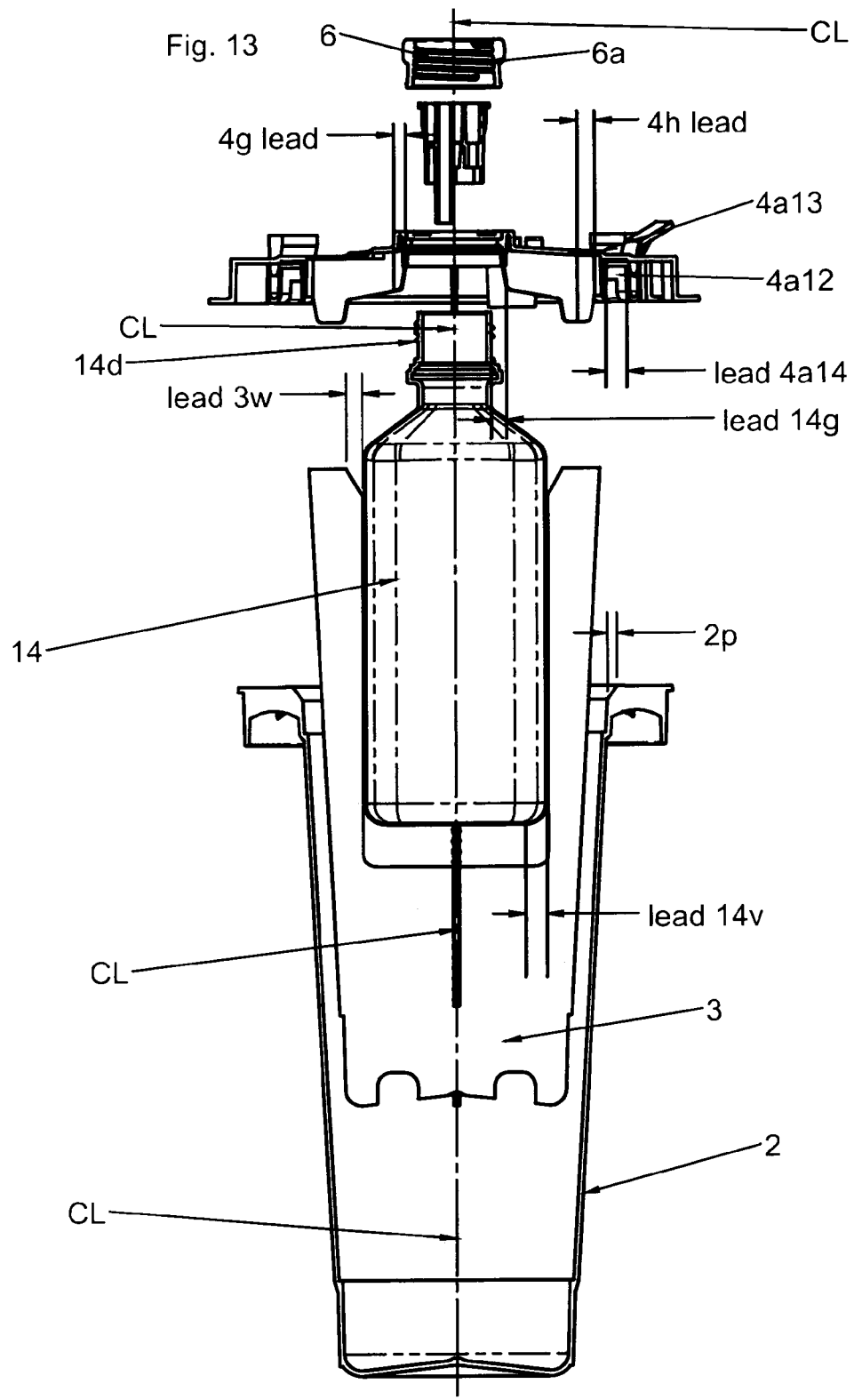
FIG. 13 shows and exploded view of canister 2 measuring stand 3, container 14, lid 4, plug 7 and thrust handle 6 with respect to an alignment relationship with a centerline as shown. Also shown are various component bevel/leads which are illustrated to show simpler assembly to provide alignment during assembly of the preferred embodiment such that assembly is easy and drops in under the weight of the parts themselves for the matching and mating of the thread thrust relationship between container 14 and thrust handle 6.

FIG. 13 depicts a cross sectional side elevation view of thrust handle 6, plug 7, lid 4, container 14, canister 2, and measurement stand 3. This view illustrates a number of assembly bevel leads such that vertical assembly of the parts may be established with a drop in self assembling system whereby the system self aligns and self assembles under the gravitation weight of its own component parts, or under the weigh of the sums of the component part which the assembly at the time of drop in assembly sequence. This figure depicts assembly lead 4g and assembly 4h of lid 4, auto flange lead 14g, measurement stand bevel assembly lead 3w, bottle/container assembly bevel/radius lead 14v, and measurement stand leads 3x and 3y. In an alternative embodiment, a curvilinear canister sealing rim 2o can make sealing contact with curvilinear soft dual shot soft seal 4a12 which has been affixed to lid 4 during molding at curvilinear lid sealing surface 4a13. The canister and lid leads at effected by the curvilinear shape of the sealing surface contours 4a12 and 2o, there between interposing the soft dual shot seal 4a12. Curvilinear lead 4a14 has a leading dimension from its curve which is closest to the centerline, and its curve which is furthest from the centerline. Curvilinear canister lead 2p has a lead dimension from its curve closest to the centerline and its curve which is furthest from its centerline. Lead 4a14 and lead 2p are shown in FIG. 13. Each of the leads, 4g, 4h, 4a14, 14g, 3x, 3y, 3w, 14v, and 2p also have a height which may be modified to further optimize the ease of assembly of the preferred embodiment 1 as each of the seals and contact point of the preferred embodiment herein defined assemble in sequence. Sequence for ht purposes of this application may indicate that the parts assemble simultaneously or in any particular order as may be defined by the modification of the herein disclosed assembly leads, whether jointly, severally or together. Similarly, each of assembly leads 4g, 4h, 4a14, 14g, 3x, 3y, 3w, 14v, and 2p each have a width and may be further modified for optimization of assembly of the preferred embodiment 1. In addition, these assembly leads assist with the horizontal and vertical alignment of the component parts of the preferred embodiments such that the container threads 14d, and their respective height, pitch, lead, and thrust handle threads 6a, and their respective height, pitch and lead may be aligned properly for engagement during assembly such that sealing and unsealing of the preferred embodiments may be easily achieved to prepare for operations and to carry out the functional and method purposes of the supply chain efficient scenarios described by the instant case. These leads are properly aligned so the canisters, of varying sizes may be easily integrated with the preferred embodiment 1.

Figure 14:
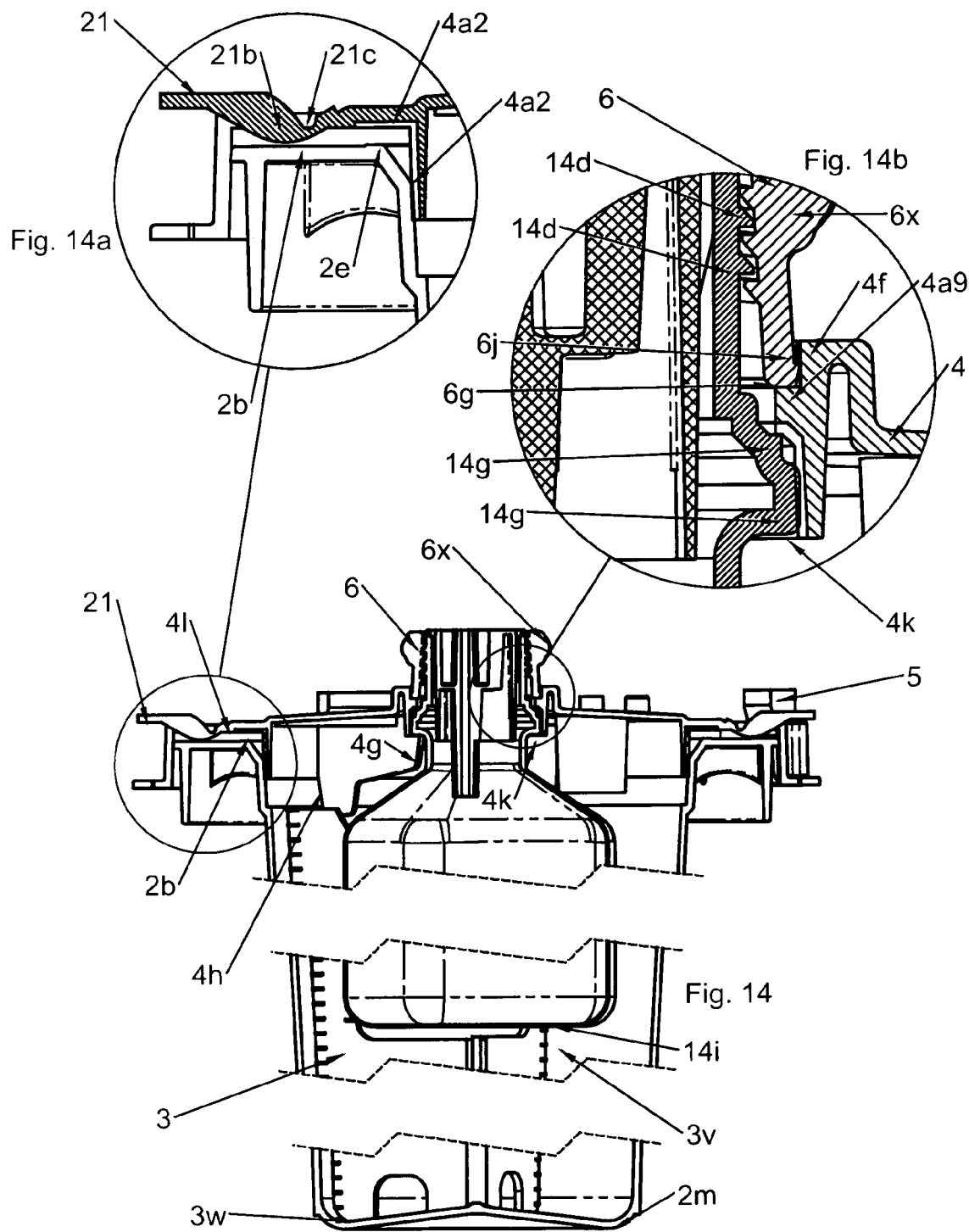
FIG. 14 shows a cross section of the preferred embodiment.

FIG. 14 is a crass sectional cutaway view of the preferred embodiment.

FIG. 14a is substantially similar to that of FIG. 12a.

FIG. 14b is substantially similar to that of FIG. 12b.

Figure 15:
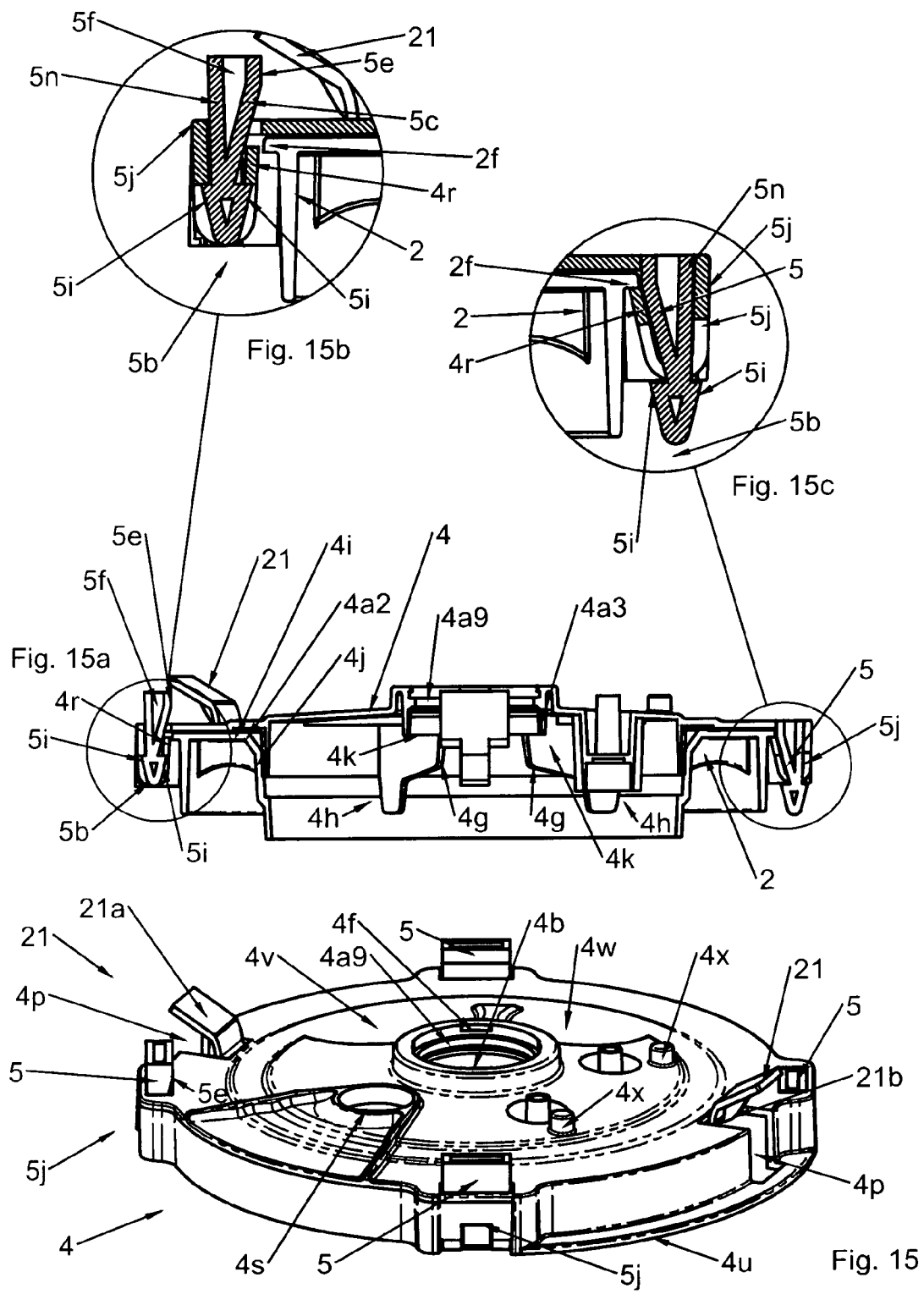
FIG. 15 shows a top perspective view of lid 4.

FIG. 15 shows details of lid 4.

FIG. 15 shows finger lift rim 4u, and four captured locks 5, jacking lever cutout slot 4p, first and second jacking lever 21, first and second jacking keel 21b, first and second jacking lever thumb push surface 21a. Also shown is bottle slot 4b, bottle cap cutaway 4w, spider cap cutaway 4v, pour spout 14s which corresponds with spider plug 8s.

FIG. 15a is a cross sectional view taken at cross section center of two of the captured locks 5, through its center. Detailed here are dual shot soft seals 4a2, 4a9 and 4a3. Soft seal bottle lid are 4k, bottle lid leads 4g, lid/canister leads 4h, jacking lever 21, flat horizontal, canister lid seal surface 4i. On the left side of the drawing captured lock 5 is shown in its upright unlocked position showing lid spring lock 4r juxtaposed to canister hook 2f in its resting position. To the right of the figure second captured lock 5 is shown in its down and locked position with the body of lock 5 having pressed lid lock 4r into an interference fit position under canister hook lip 2f. Back to the first lock 5 on the left side of the view the molding slot 5f of lock 5 is shown as well as the lock advancing body 5e is shown.

FIG. 15b is a detailed blow up of the left circle as shown in FIG. 15a, as seen 21 depicts the jacking lever. Lock 5 is depicted by its molding slot 5f, its back side 5n, slot back lock support 4a11 of lid 4, retaining hooks first and second, 5i, lock finger push up bottom 5b, canister 2, lid spring lock 4r, lid hook lift 2f, spring lock push ramp 5c, and spring lock set surface 5e. This figure depicts the captured lock 5 in the upright position, also shown is that it is retained by the interference dimensional fit between lock retention barbs 5i as they are held in place by slot push back 4a11 and spring lock 4r. Lock 5 is assembled to lid 4 by pressing lock 5 down into slot 4q of lid 4. Spring lock 4r springs out and allows first and second retention barbs 5i of locks five to snap into place below spring lock 4r. Spring lock 4r and slot push away surface 4a11 co act together. It is also noted that lock ramp 5c and set surface 5e are positioned towards the center of lid 4 as it is snap assembled into slot 4q.

FIG. 15c is a blow up detail of the right blow up circle as depicted FIG. 15a. FIG. 15c shows the captured lock in a downward locked position. It is shown when the captured lock is pressed downward such that lock top 5a is substantially flush with the surface with lid 4 as shown. Lock spring push ramp 5c pushes lid spring lock 4r which has been juxtaposed to canister rim 2f, which in turn causes an interference fit and locks lid 4 to canister 2 for safe transport of the preferred embodiment 1. As lock 5 is pressed down and lid spring lock 4r resists locking translation under canister hook lip 2f, lock back 5n is stabilized by lid lock support back at 4a11.

Figure 16:
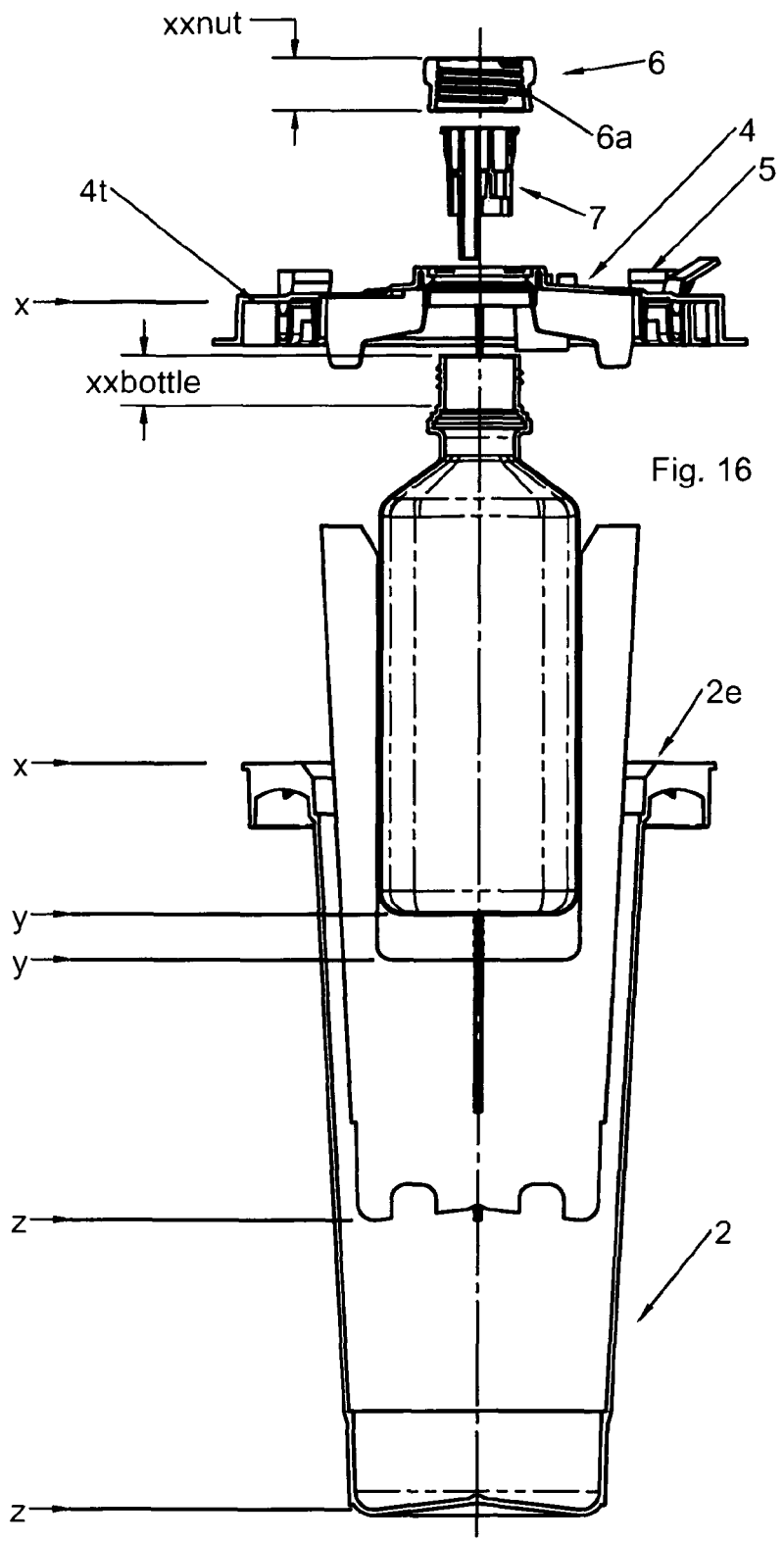
FIG. 16 shows an exploded cross section view of the preferred embodiment of sheet 13 depicting horizontal special relationships of the sub-assembly. This view details specific assembly contact points that are important relative to the clockwise and counterclockwise thrust orientation action of thrust 6 relative to its imparting its thrust onto container 14. XX-nut depicts a thread height of thrust 6, XX-bottle depicts a thread height of bottle thread 14*d*. When thrust 6 is fully orientated in clockwise orientation as defined in FIG. 3, FIG. 4*b*, FIG. 5*b*, FIG. 6*b*, FIG. 7*b* FIG. 12*b*, FIG. 14*b*, FIG. 18, FIG. 20, FIG. 21, & FIG. 22 and well as would be in FIG. 1, dimension XX-nut and dimension XX-bottle substantially overlap dimensionally and or are dimensionally superimposed. When thrust nut 6 is rotated fully in its counterclockwise orientation dimension XX-nut and dimension XX-bottle un superimpose vertically and create a thrust unsealing dimension expansion comprising the sum of dimensions XX-bottle, and dimension XX-nut.

FIG. 16 is an exploded assembly view of canister 2, measurement stand 3, container 14, lid 4, lock 5, plug 7 and thrust handle 6. Also detailed are stack datum's x showing the lid and x showing the surface seal 2e of canister 2, which defined a mating sealing surface between the lid 4 and canister 2. Also shown are y and y the upper y showing the container bottom 14i and the stand bottle slot rest surface 3v of said stand. Also shown are z and z, the upper z showing the bottom of measurement stand contact surface 3y and the lower z showing the bottom of the inside 2n of canister 2. As assembled in the sealing position, plug 7 and bottle 14 seal at dual shot bottle plug and container throat seal 7f, the container and lid seal at seal 4a3 and the lid/cannier seal at 4a2. It is also noted that these sealing areas make contact with their respective contacting parts in a substantially horizontal relationship such that when the part are assembled as such is shown inn FIGS. 21 and 22 among other, vertical and horizontal relationships remain substantially accurate enough such that handle thrust threads 6a of thrust 6 properly engage container thread 14d of container 14. It is also important to note that the assembly bevel leads as described in FIG. 13, cooperate in a sequence to assistance in the vertical and horizontal alignment of thrust thread 6a and container thread 14d It is also important to note that these leads are arranged and have the structuration to align said threads such that as each lead self engages in sequence, each sequential lead component assembly the distance between the centerline and the point of center of each of these lead has cooperative sutrcutration such that, the leads effectively center and align thread 6a with 14d. It is also important to note that xx-nut defines a thread height of 6a, and xx-bottle defines a thread height of 14d. It is also understood that thread height xx-nut of 6a end thread height xx-bottle 41d may be threaded and unthreaded and vertically superimposed height wise, and create an excursion distance being defined by a clockwise sealing thrust and a counterclockwise unsealing thrust, effecting excursion distance which may equal the sums of the thread heights xx-nut and xx-bottle. The thrust handle contains the potential to impart a force through handle thrust 6, which is very easy to turn yet imparting a significant sealing and unsealing thrust. At sealing area 4k and at seal 4a2 and a counter clockwise unsealing thrust, the thrust excursion distance between container 14 being the sum of xx-nut and xx-bottle, and an unsealing force at x and x contact areas at dual shot seal 4a2 and also bottle lid sealing area 4k at soft dual shot seal 4a3 through a counteracting contact at container stand yy and stand canister contact zz.

Figure 17:
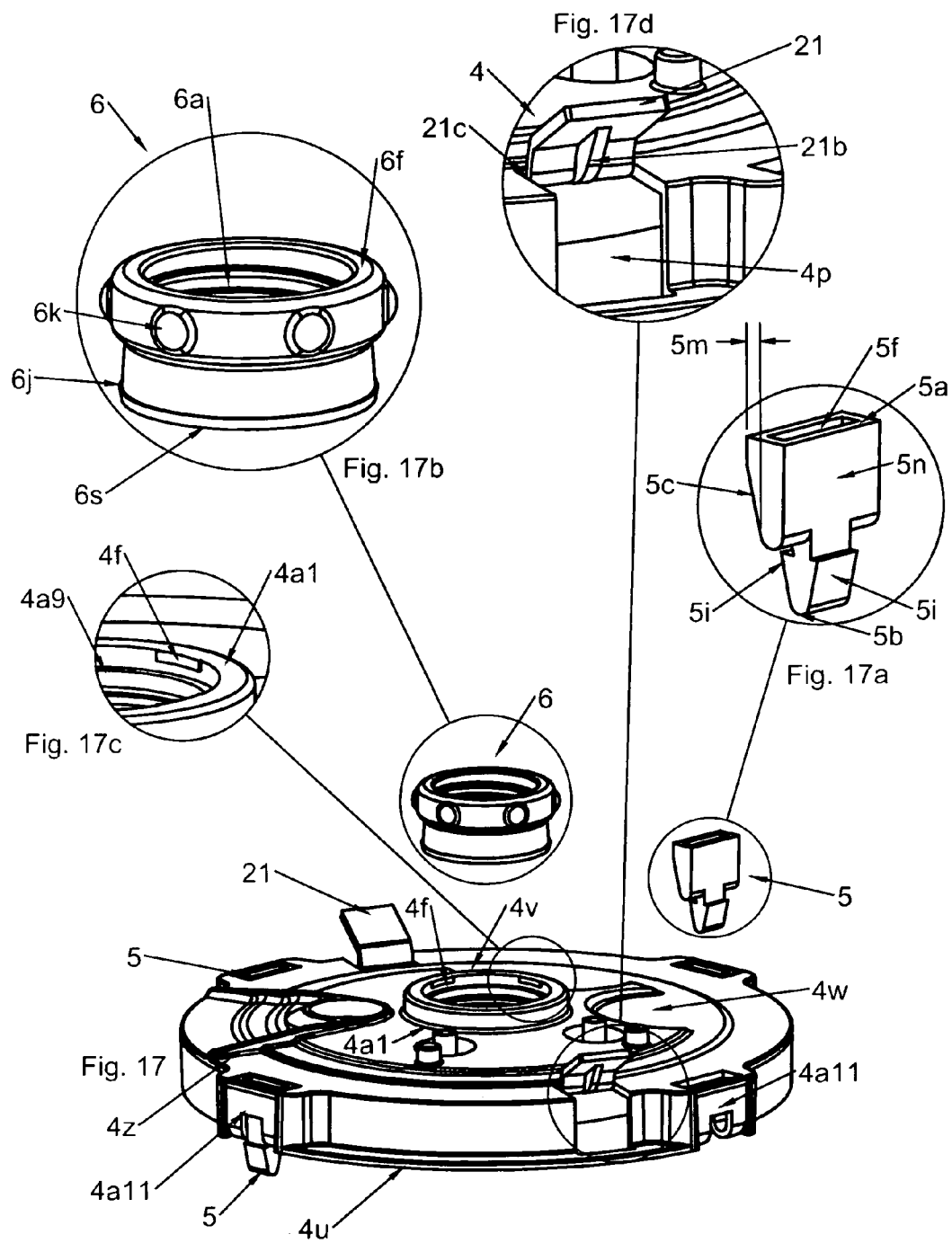
FIG. 17 is a top perspective view of lid 4.

FIG. 17 is a top perspective view of lid 4 showing finger lift rim 4u, one of four locks 5 in the down locked position, lock push back slot 5j of locks slot 4q shown in two of four places, pour spout fluid guides 4z, locks five, leveraging ramp 21 lid hook catch and thrust handle retaining hook k4f, spider cap boss 4a1, spider cap cutout 4v, container cap cutout rest 4w.

FIG. 17a shows a blow up detail of lock 5. Shown here is lock 5 bottoms 5b, a finger push up area, first and second retention barbs 5i, lock back 5n, spring lock push ramp 5c, molded in lock slot 5f, lock top 5a, 5m depicts a spring lock push distance.

FIG. 17b is a blow up of handle thrust 6 showing thread 6a, thrust top 6f, thrust retaining rim 6j, thrust bottom 6g, finger friction bumps 6k.

FIG. 17c is a blow up detail of the features of lid boss 4a1 and its handle thrust 6 retaining features. Show in the blow up of 17c, is lid boss 4a1, hook catch thrust retaining hooks 4f, and sealing thrust bearing surface 4a9.

FIG. 17d is a blow up detail of leveraging jack 21 detailing push off contact keel 21b showing lid 4, flexion detent 21c of lid 4, leveraging jack cutout 4p.

Figure 18:
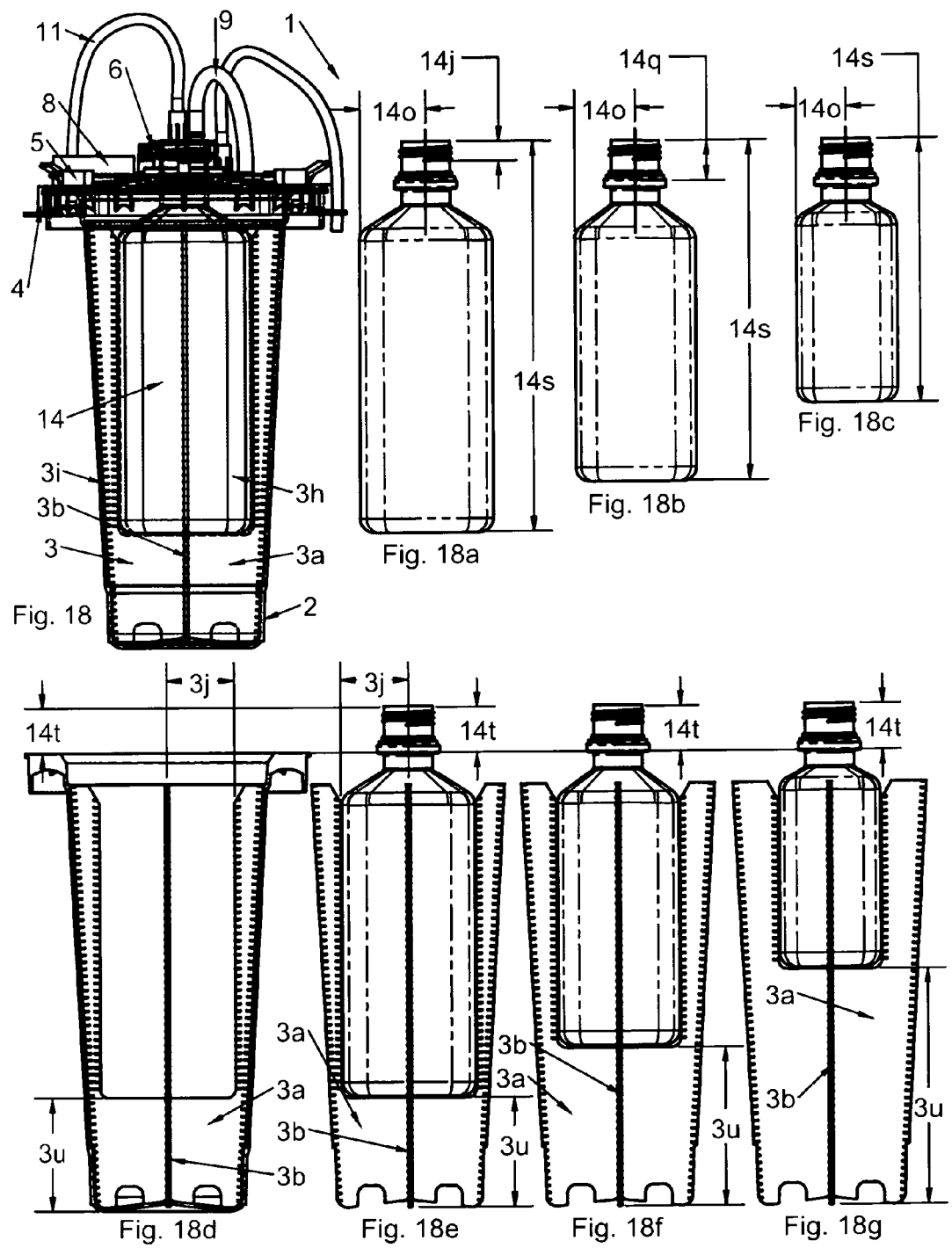
FIG. 18 shows the side elevation transparency view of the preferred embodiment of FIG. 1 in a different rotation view, and in horizontal alignment aspect with respect to different container sizes of FIGS. 18, 18*a*, 18*b*, & 18*c*.

FIG. 18 shows a transparency view of the preferred embodiment 1, detailing patient hoe 11, transfer hose 9, thrust handle 6, spider cap 8, lock 9, lid 4, container 14, measuring stand indicia, 3i, container measuring indicia 3h, measuring stand 3, comprising the subassembly components 3a and 3b of stand 3, canister 2.

FIG. 18a shows thread height 14j of thread 14d, distance between the centerline to the flat side of container 14o.

FIG. 18b shows the distance form the assembly centerline from the flat side 14o of container 14, the 14 q which is the height distance from seal flange 14g of container 14 to the top of container 14h, the distance form the top 14h of container 14 to the bottom 14i of container 14.

FIG. 18c shows the distance 14o from assembly center line to the flat bottle side 14o of bottle 14 as well as a bottle height 14s showing a distance from bottle top 14h to bottle bottom 14i.

FIG. 18d shows a distance 14t depicting a measurement from the sealing rim 2e of stand 3 to the top 14h of container 14, measurement 3j defines a distance between the assembly centerline and the inside wall 3j of measuring 3 the inner pillar edge shown at 3e. Also defined is measuring distance 3u which defines the distance between the bottom measuring stand 3y and the bottle contact surface 3v of stand 3 as assembled comprising 3a and 3b.

FIG. 18e shows a measurement from the assembly centerline to measuring stand inside pillar edge 3j. Also shown is the height distance 14t defining the distance between bottle top 14h and horizontal canister seal surface 2e. Measuring stand parts 3a and 3b are shown assembled perpendicularly in the vertical plane with respect to each other, and distance 3u defines substantially similar features as found in FIG. 3d.

FIG. 18f substantially similar bottle 4p, 4h, sealing rim 2e, dimension at 15t as well as a substantially larger dimension 3u defining a distance 3u between measuring stand bottom 3y and bottle contact surface 3v and FIG. 18 depicts the substantially the same measuring distance 14t defining the top of bottle 14h and horizontal canister sealing surface 2e and showing dimension 3u from the bottom of stand at 3y to the bottle contact surface 3v as yet being again greater.

FIG. 18 through 18 g define a preferred embodiment system 1 may be provided with a first, second and third container/stand combination to accommodate the collation of fluid waste in various container sizes and volume, and shapes. Third fourth and fifth and possible more various sized and shaped containers may be made with similar thread height as shown in 14j with respect to the top of bottle 14h and the bottom of thread 14d as well as shown in FIG. 18d, a substantially similar distance between flange 14g and bottle top 14h as shown at 14q, bottle height distance 4s of FIG. 18 through 18c correspond in structuration differential distance 3u as depicted if FIGS. 18 d thorough 18d so that substantially similar bottle thread height xx-bottle as defined in FIG. 16 may be similar yet accommodated by the preferred embodiment 1 irregardless of volume, size shape etc, with different 3u distances as defined in FIGS. 18 d, e, f, & g. In sheet 18 of 23 it is show how very high volume production containers of various volumes, shapes and sized may be made with a common thread area, a common sealing area such as thread area 14d and thread flange 14g, as well as common sealing dimensions, and common assembly contact sealing and unsealing dimension allow integration of a plurality of container volumes and sized into the preferred embodiment, by the modification of a measuring stand 3 as shown in sheet 18. The modification of measuring stand 3 allow for various bottle volume sized to be embodied by the preferred embodiment whereby a thrust handle provides a significant sealing and unsealing thrust to a plurality of containers having a common thread height area and a common sealing area.

Figure 19:
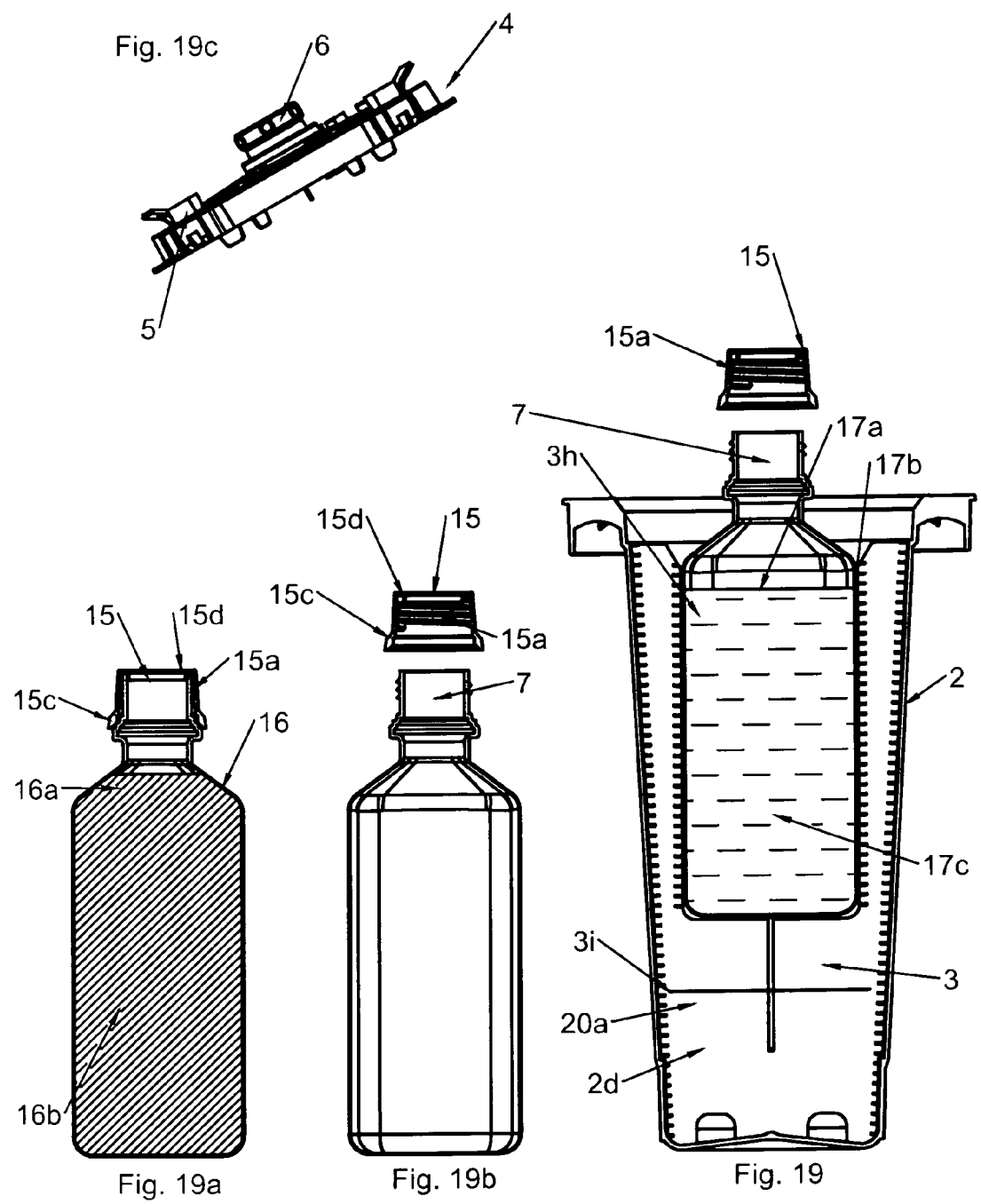
FIG. 19 is a side lavational cross section of the preferred embodiment having lid 4 removed. Waste material has been vacuum drawn (suctioned) into the container and cap 15 is shown in position for readily placement onto bottle 14 sealing in the contaminated waste. This view depicts lid 4 as having the associated vacuum draw hoses/tubing removed thread 6a and thread 14d having been disengaged, thrust handle 6 may be used as a handle, to be held in one had to hold lid 4 in one hand and while lid 4 occupies one handoff an operator, and exchange operation may be carried out with the other hand whereby cap 15 is removed from cutout 4v of lid 4, cap 15 may then be threaded onto bottle 14 while being held in the measurement stand 3, sealing the container. This provides and easy way to seal contaminated waste into container 14 without having to handle or transfer the container 14 while it is unsealed and full of contaminated biological wage fluid material. Container 14 can then be easily removed and another empty container such as in 19b can be placed into measurement stand 3 as shown in FIG. 19, and then lid 4 may be places onto canister two in fairly smooth ergonomic fusions.

FIG. 19 is a cross section of the preferred embodiment having lid 4 removed. FIG. 19 shows an improved and efficient human factors and ergonomic sequence for and operator such that one hand may pack up lid 4 by thrust 6 and carry out the operation of changing out the container 14 having waste material and replacing it with a empty container using one hand. Bottle 14 contains-waste material 17a places within lid 2 making contact with stand 3 at stand location3v and bottle bottom 14i. Lid 4 has been removed. Also for illustration, canister fill line 20a shows the potential of overflow of waste material into the canister housing area 3h is shows as indicia measuring the amount of waste material in the bottle, and 3i shows indicia on stand 3 showing the potential amount of the sums of the material both in the bottle and the canister at 3i. It is noted that although the bottle in FIG. 19 is not completely full the indicia measurement at 3i would be useful if first the bottle was full and then there was overflow. Also shown is throat area, plug 7, bottle cap 15 with bottle cap thread 15a. In this view the preferred embodiment has been utilized to collect waste in a fluid enclosing bottle/container. The hoses/tubing is shown removed from lid 4, thrust handle 6 has been used to unseal the system using counterclockwise rotation imparting distraction excursion forces initiate by the engagement of bottle threads 14 and thrust thread 6a. Handle thrust 6 may be held in one hand by the operator as depicted in 19c (hand not shown), cap 15 has been removed from cap cutout 4w of lid 4 and disposed to re-seal waste 17a in container 14. Once cap 15 is completely tightened sealing bottle 14, the operator may lift said bottle out of the preferred embodiment with one hand (the free hand) and while still holding lid 4 in the other hand, place a new empty bottle 14 as defined in FIG. 19b into the stand 3 all of which may be carried out with one hand while the other hand holds lid 4. Lid 4 may then be placed back onto the canister to holding handle thrust 6 and thrust 6 may be oriented through a clockwise excursion thusly using forces emanating forces from contact between thread 6a and 14d to fully seal the bottle flange 14g with lid at sealing area 4k at seal 4a3. Full clockwise orientation of handle thread 6 superimposes in vertically dimensionally thrust thread xx-thrust and xx-bottle as defined in sheet 16 allowing superimposing of thread 6a and 14d closing the sum of the distances thread height 14j and thread height 6b each having a cooperative height thread angle pitch and lead to allow for captive structuration to align the sums of the heights are substantially superimposed and substantially reduced the one half of said height sums. This clockwise rotation allows for a dimensional stack up referencing sheet 16 such that canister sealing rim 2e and seal 4n may come into full seal contact, the bottom of bottle 4i and the bottle rest surface 3v and the measuring stand 3 has slight gap in the system and the system may be fully sealed at soft dual shot seal 4a2 and 4a3.

FIG. 20 shows another potential embodiment of unsealing lid 4 form canisters 2. In this view thrust 6 is left untouched and finger lift flanges, first and second 4u are lifted up while first and second jacking lever 21 are pressed down by thumb pressure separating lid 4 and canister 2.

Figure 21:
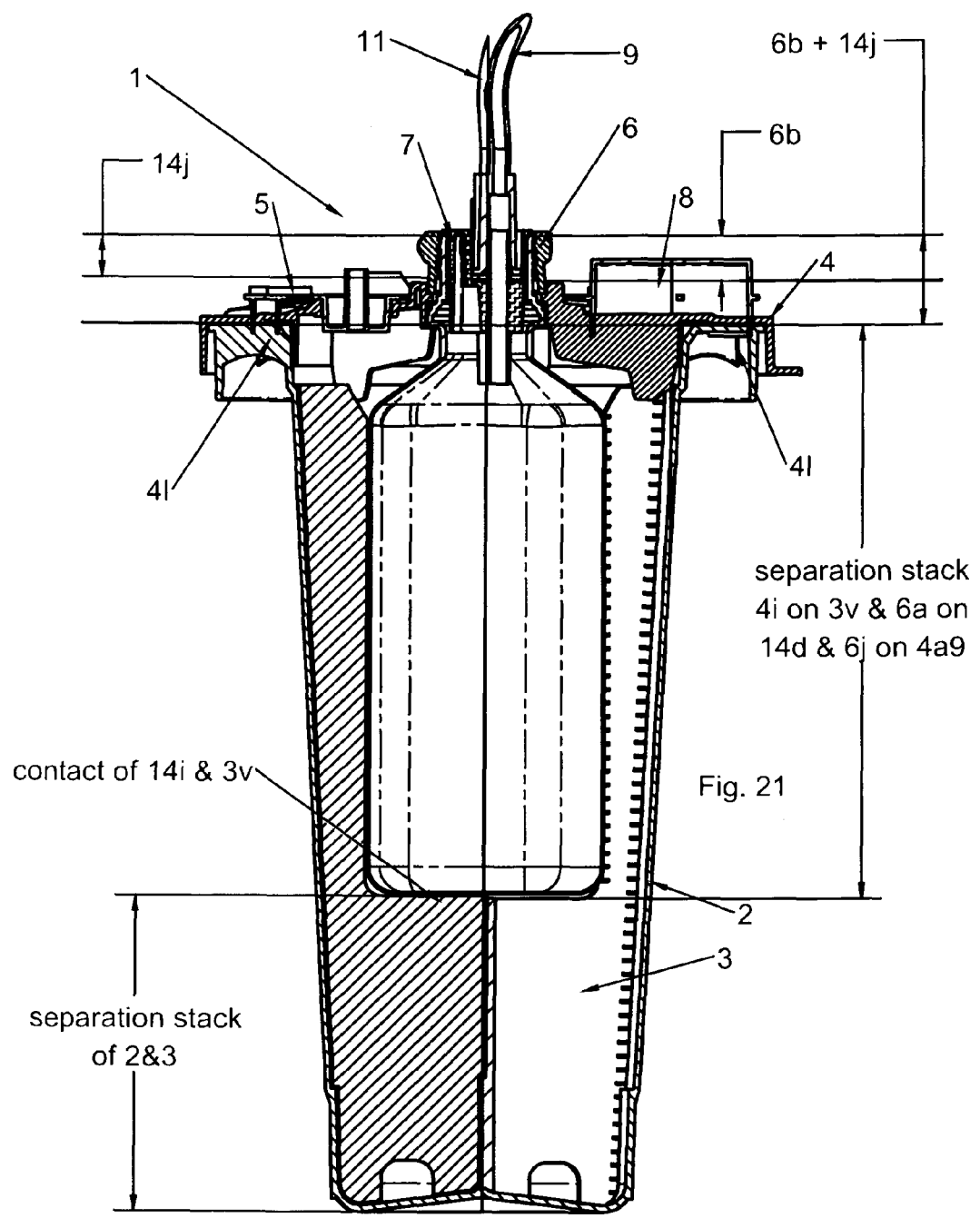
FIG. 21 defines the component s contact stack dimensions that operate under counterclockwise orientation of thrust handle 6.

FIG. 21 shows contact stack of the components that are in structuration during sealing and unsealing of the preferred embodiment. Shown here are measurement stand 3, canister 2, lid 4, lock 5, thrust 6, and spider cap 8. FIG. 21 shows the sums of the thread heights of bottle 14 and thrust 6, and further explains the sums of the thread heights providing separation excursion distances between lid 4 and canister 2 as explained in FIG. 16. 14j defines a bottle thread height. 6b defines a thrust thread height. 6b+14j defines the sums of the thread heights 6b and 14j, separation stack of canister 2 an did 3 is shown by horizontal line further defining contact of the bottle bottom 14i and slot bottom 3v of stand 3. Also shown is a vertical separation stack dimension defining a bottle stand contact between canister lid contact dimension which further defines a separation stack of 4i on 3v and 6a on 14d, and 6j on 4a9.

Figure 22:
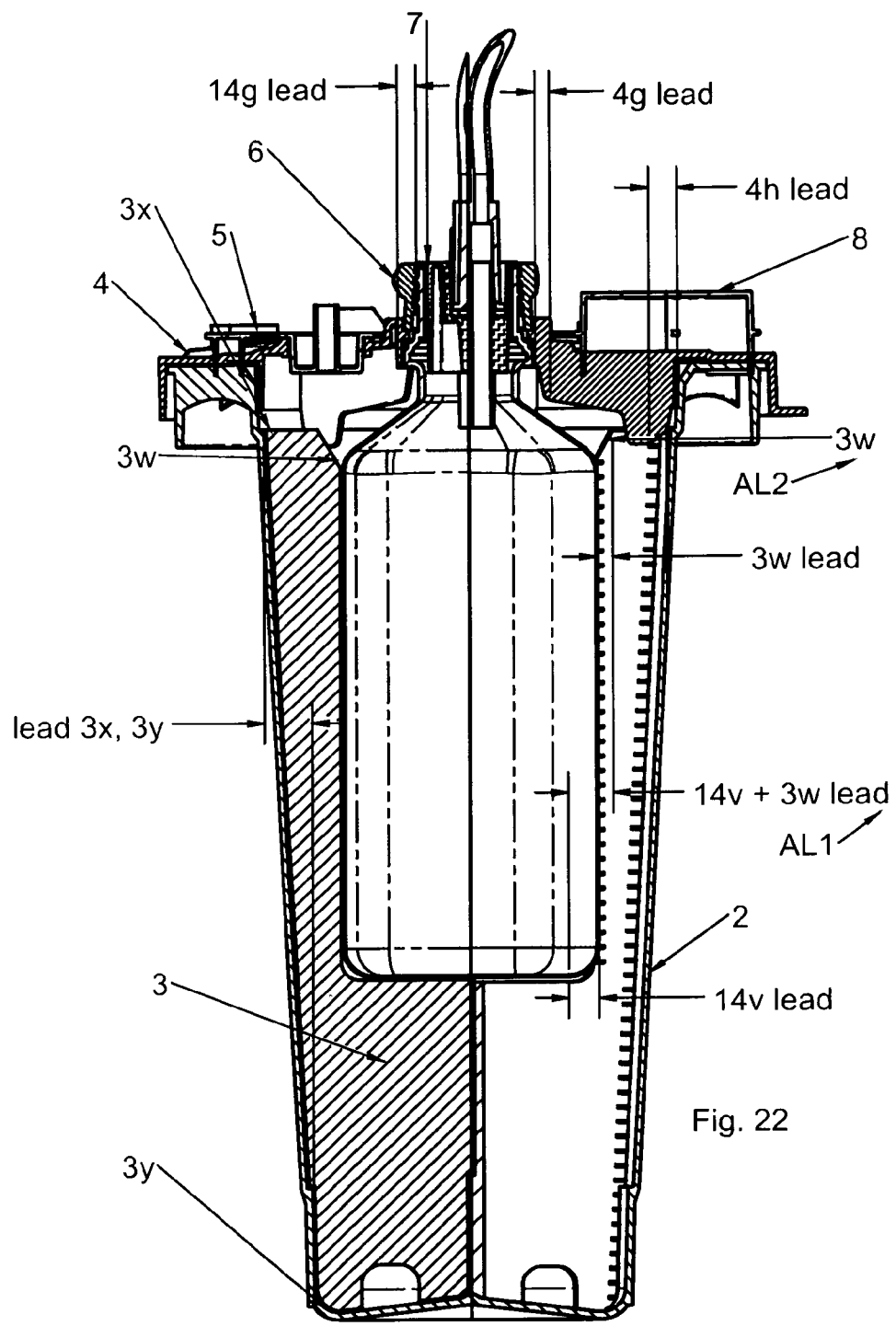
FIG. 22 further defines the vertical leads of the various parts defined in sheet 13 however in a cross sectional view of the assembly of the preferred embodiment.

FIG. 22 further shows the assembly leads defining a easy to use assembly structuration between canister 2, measuring stand 3, bottle 14, lid 4, to further assit in the proper alignment of the bottle thread and a lid thread and sealing surfaces 4a2 and 4a3 as well as sealing area 4k. Also shown is plug 7. Assembly lead 4g allows easier assembly and vertical and horizontal alignment of bottle 14 and lid 4. Assembly lead 4h allows easier vertical and horizontal alignment of lid 4 and d canister 2. Another helpful lead would be to have the mating surfaces and associated seal to be curvilinear shaped having corresponding mating seal surfaces having a vertical and horizontal lead from the portion of the curves which is closest to the centerline to the portion of the curves furthest from the centerline. This particular lead would allow a greater slop in assembly and disassembly as well as shorter vertical friction dimension required to unseal lid 4 from canister 2. Leads 4g and 4h are defined by a plurality of leads as they are built into t plurality of vertical wall mold support struts providing strength to the lid during high negative pressure. Also shown is lead 14v on the bottom corner of container 14 and lead 3w which is a cutout bevel of the tops of each of the four measurement stand pillars of components 3a and 3b of stand 3. these leads all work together to define easier drop in assembly for various bottle sizes to be integrated into the preferred embodiment and are further defined by the use of a plurality of measuring stands 3 each accommodating the size and shape to match threads 6a and 14d.

Figure 23:
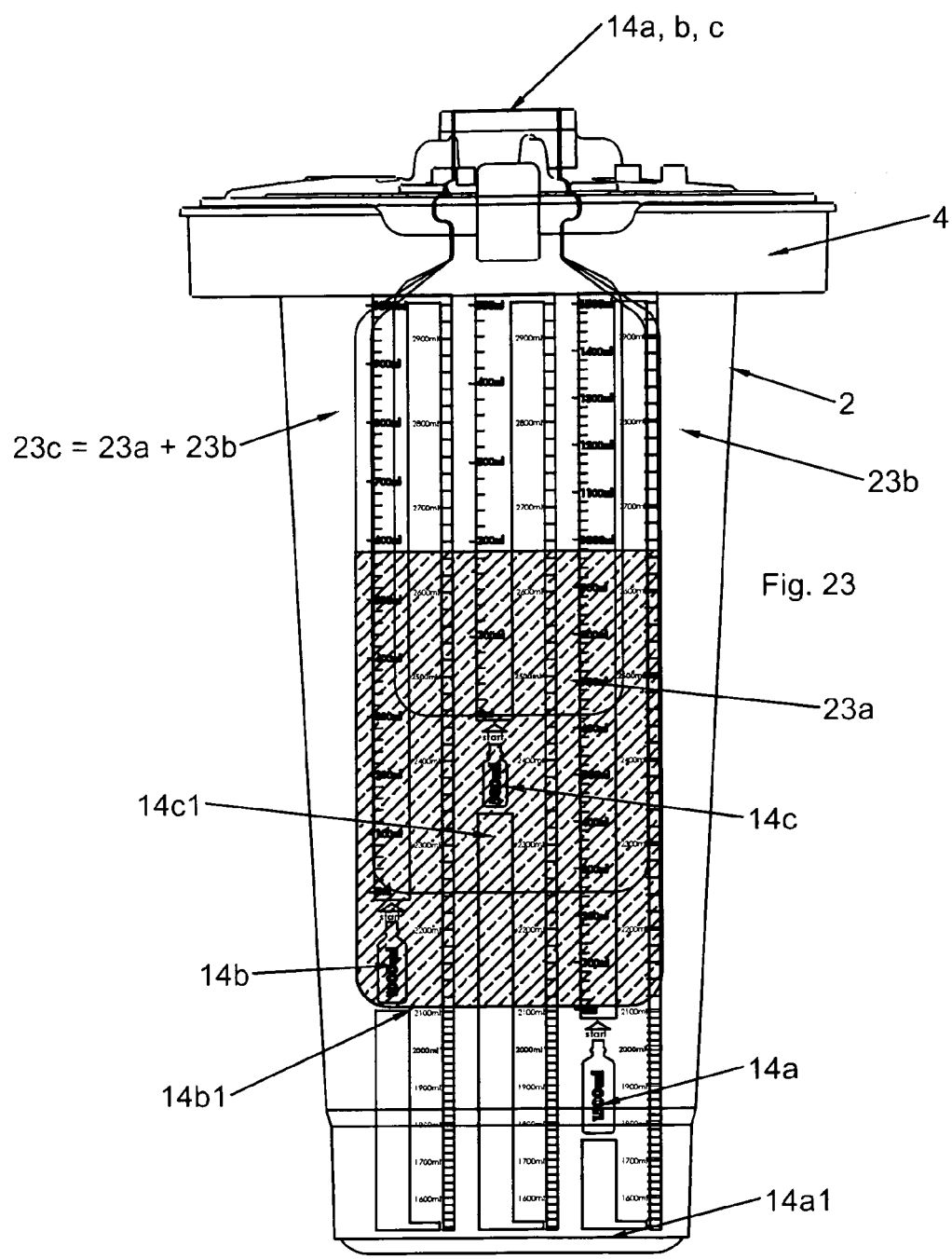
FIG. 23 is a side elevation of an alternative means of indicia depicting a three in one fluid volume measurements system laid out on the outside of a canister 2 whereby several different size bottle volumes can be measured from the outside of a single canister body. The different bottle volumes fit in and are measured off of the same canister body such that for each size there is an indicator of volume in the container and in the event of overflow from the bottle into the canister, measurement from each container volume size that indicate both the volume in the bottle and the overflow volume which has been drawn into the canister, by showing in one vertical measurement strip the volume equivalent to volumes associated with the waste collected in the bottle plus the overflow amount in canister. The measurement amount in the canister, at the bottom of the measurement strip begins with the volume of the bottle volume which is inside the canister. For example, if the measurement strips on the outside of the canister depict that there are three volumes of bottles associated with this canister, then there may be a picture of the bottle volume and the numbers for each respective measurement strip at the bottom of the canister begins at a volume number that represents the amount of fluid which has already been drawn into the bottle, for the volume of the particular bottle in the canister at that time.

FIG. 23 shows side elevation view of indica placed on the outside of the canister housing. This view shows six fluid measurement fluid level areas each measuring the level of fluid in the respective different container volume sizes plus that volume and the volume which would be in addition to that volume plus the volume of fluid in the canister 2 in the event of overflow from the bottle 14, through transfer hose 9 and into canister 2.

Figure 24:
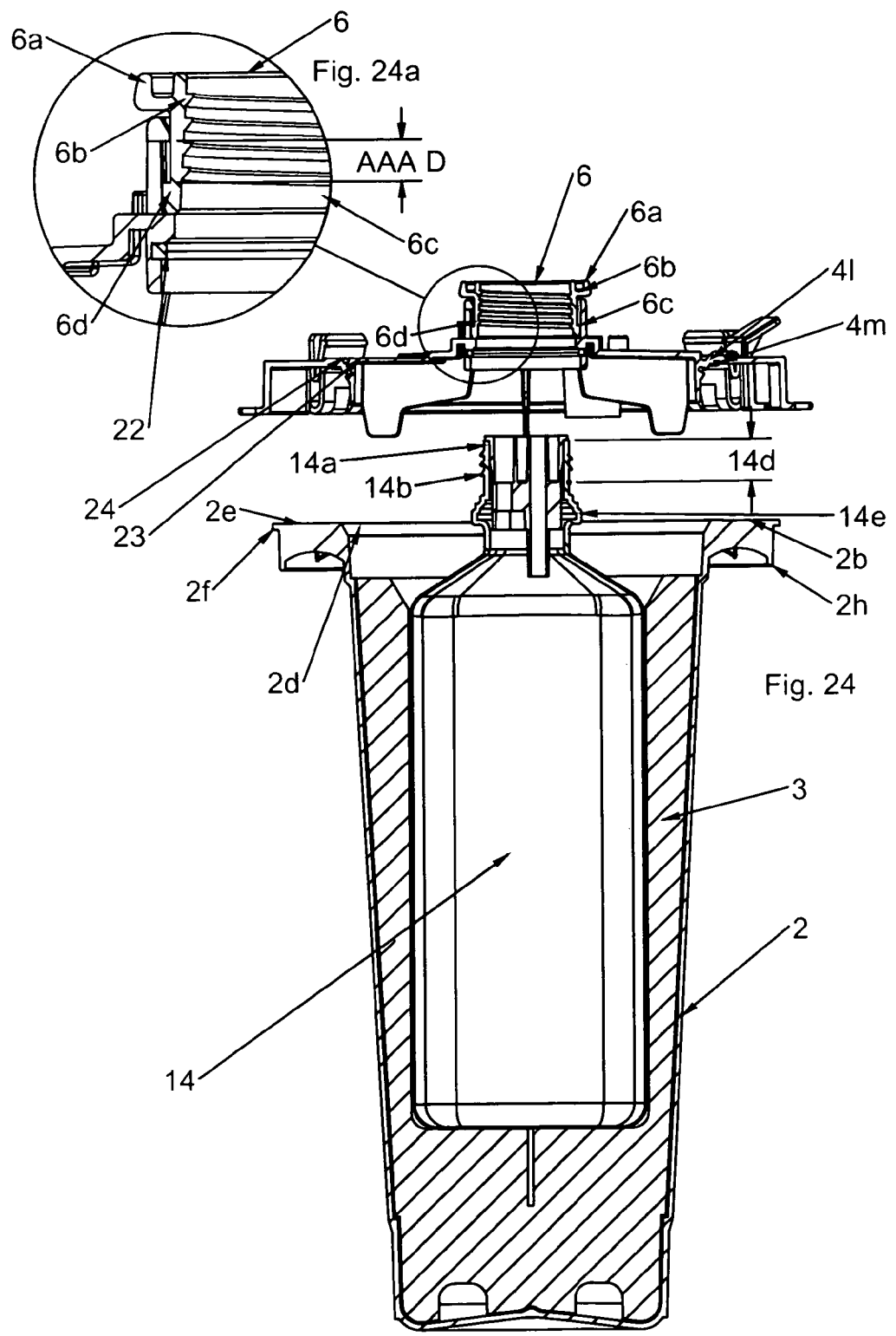
FIG. 24 shows a cross sectional plan view of a canister system prime'.

FIG. 24 shows a detailed description of canister system' embodying canister 2', pour bottle 14', measurement stand 3', canister handle grip 2h', contact surface 2b', sealing surfaced 2e', sealing surface 2d', bottle flange 14e'. FIG. 24 also shows at 14a' and 14b' the locations from the top to the bottom of the bottle neck thread. 14d' also depicts a distance whereas the distance is relative to a thread able engaging thrust relationship engagement wherein thrust handle 6' as well as how thrust handle 6' when moved in one direction aaa' reacts to cause a seal between lid 4' and bottle 14' and when rotated in the opposite direction bbb' may act to cause a thrust motion for unsealing FIG. 24a shows depicted by aaa' d a particular thrust distance of travel caused by thrust handle 6'. Also shown is o-ring 22', thrust handle retaining retention rim/hook 6d', thrust handle grip 6a', thread 6b' and thread 6c'.

Figure 25:
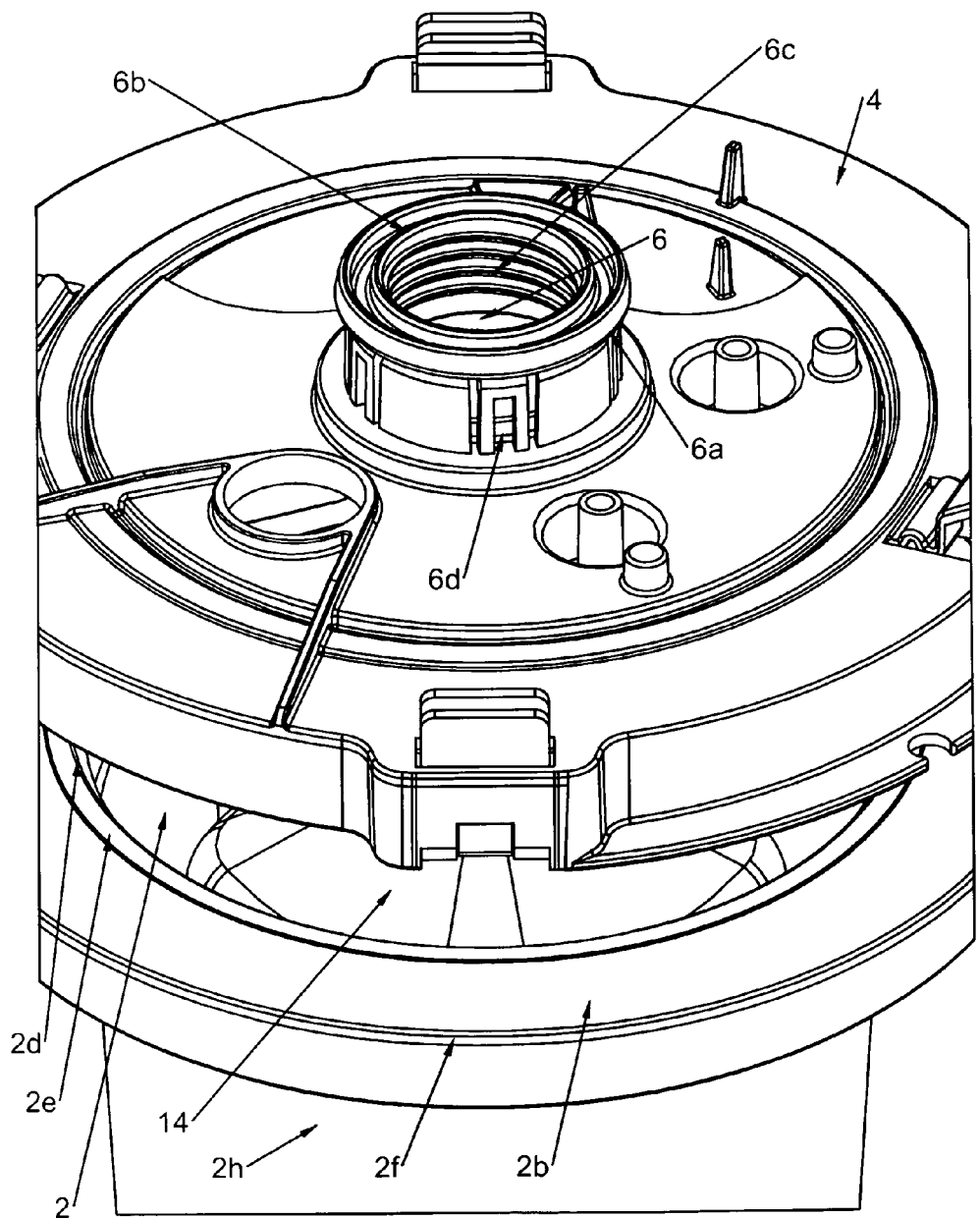
FIG. 25 is an isometric view of canister 2', pour bottle 14', lid 4', and thrust handle 6'.

FIG. 25 shows an isometric view of lid 4' above canister 2'. Pour bottle 14' is shown resting within canister 2' in measurement stand 3'. Also shown canister sealing surface 2e' and 2d'. Thrust handle 6' is shown attached to lid 4' showing threads at 6b' and 6c' and also showing thrust handle retaining rim/hook 6d'.

Figure 26:
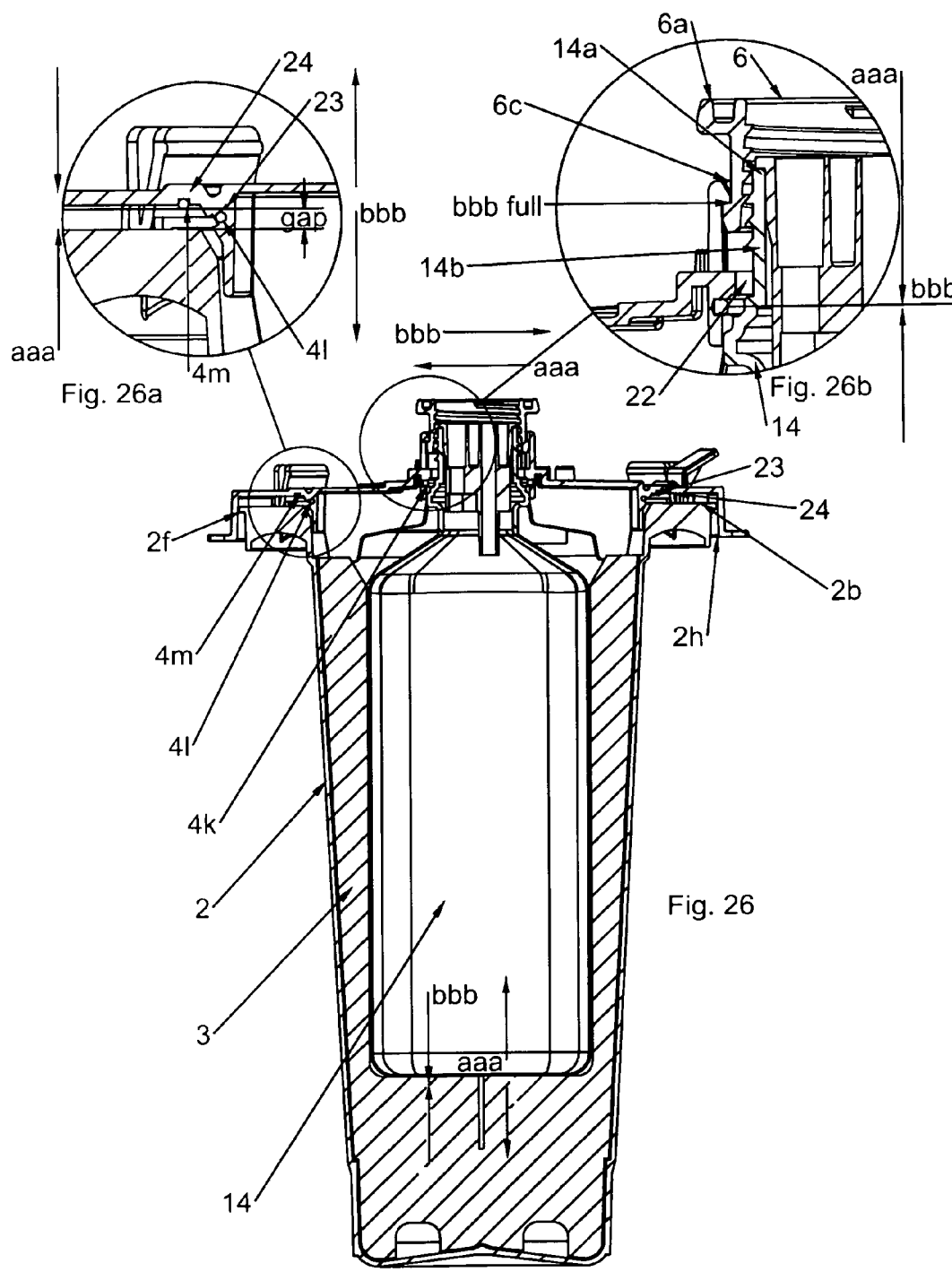
FIG. 26 is a cross sectional view of canister system', with thrust handle 6' in an up position as it relates to the threads of pour bottle 14' and the threads of thrust handle 6' having made thrust contact.

FIG. 26 is a cross sectional view of canister system 2'. FIG. 26 depicts thrust handle 6' having rotation in one direction aaa' and another direction bbb'. These two opposing directions may otherwise be referred to as clockwise and counterclockwise directions.

FIG. 26 depicts contact thrust pressure forces bbb' corresponding with the counterclockwise rotation of thrust handle 6' and FIG. 26 shows contact separation thrust aaa' which corresponds with thrust handle 6' being rotated in direction aaa'. Thrust handle 6' when rotated in clockwise direction aaa' may be defined as being defined as thrusting in a sealing direction. Thrust handle 6' when rotated in a counterclockwise bbb' direction can be defined as thrusting in an unsealing direction. Sealing in enacted by contact thrust between bottle 14', and o-ring 22' which sit in o-ring groove 4k' of lid 4', and sealing between surface 2e' and 2d' of canister 2' and o-ring 23' and 24' as situated in o-ring grooves 4m' and 4l'.

FIG. 26b shows a horizontal line across the level of o-ring 22' with arrows aaa' and bbb' each depicting the effects of sealing thrust and unsealing thrust effects as earlier described with respect to rotation of thrust handle in one direction and rotation of thrust handle of 6' in the other direction. FIG. 26b also shows contact bbb' full between lid 4' and thrust handle 6'. When this contact is made upon counterclockwise rotation of thrust handle 6', threads 6b' through 6c' engage threads. 14a' through 14b' enacting thrust force and causing unsealing thrust.

Figure 27:
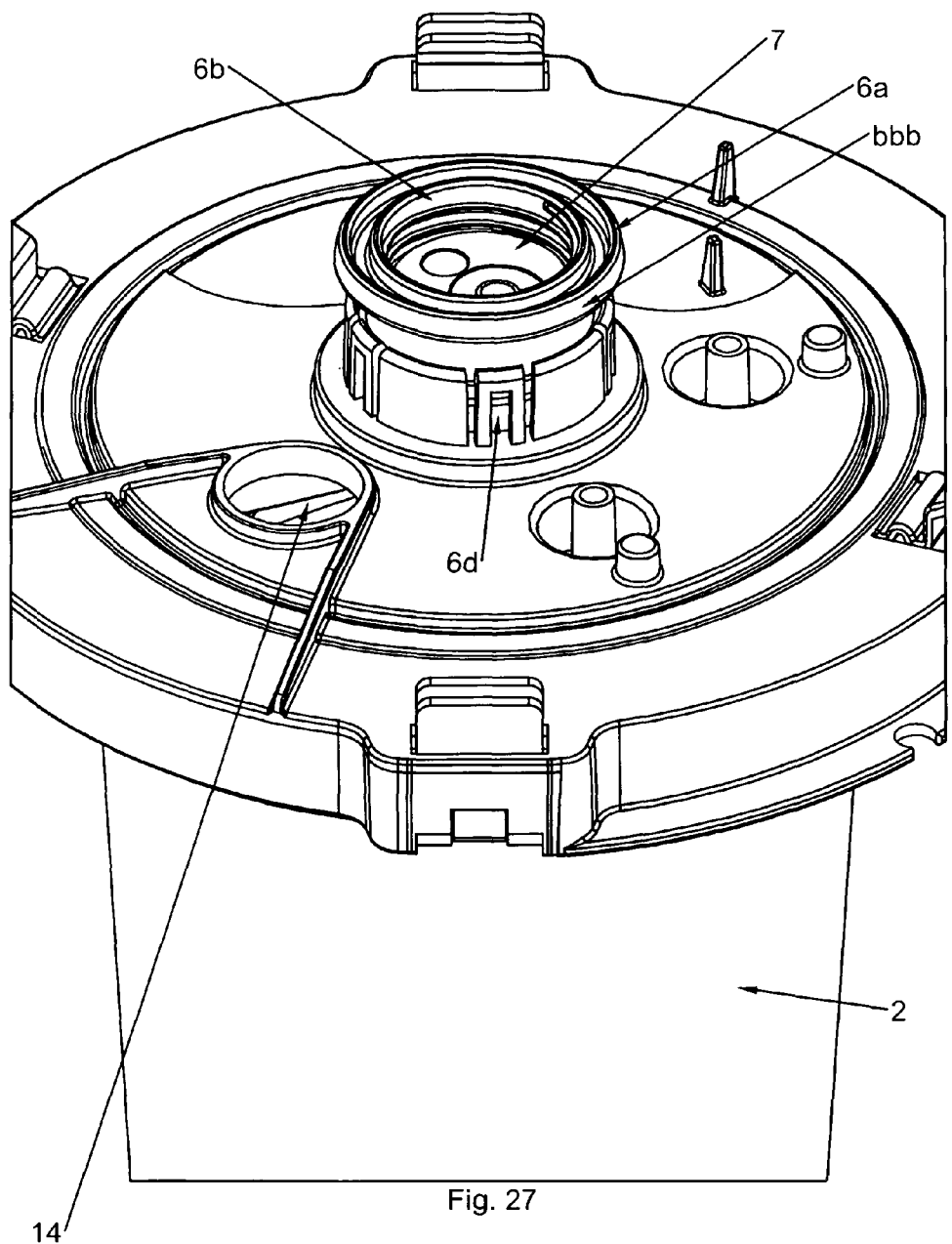
FIG. 27 is an isometric view canister 2', bottle 14', flush plug 7', thrust handle 6'.

FIG. 27 is an isometric view of assembled lid 4' and canister 2' and also showing bottle 14', flush plug 7', thrust handle grip 6a' and thrust handle retaining hook 6d'. This figure also shows at bbb' thrust handle 6' being rotated in a counterclockwise direction engaging the threads of thrust handle 6' with bottle neck 14' to cause downward thrust on bottle 14' enacting unsealing thrust.

Figure 28:
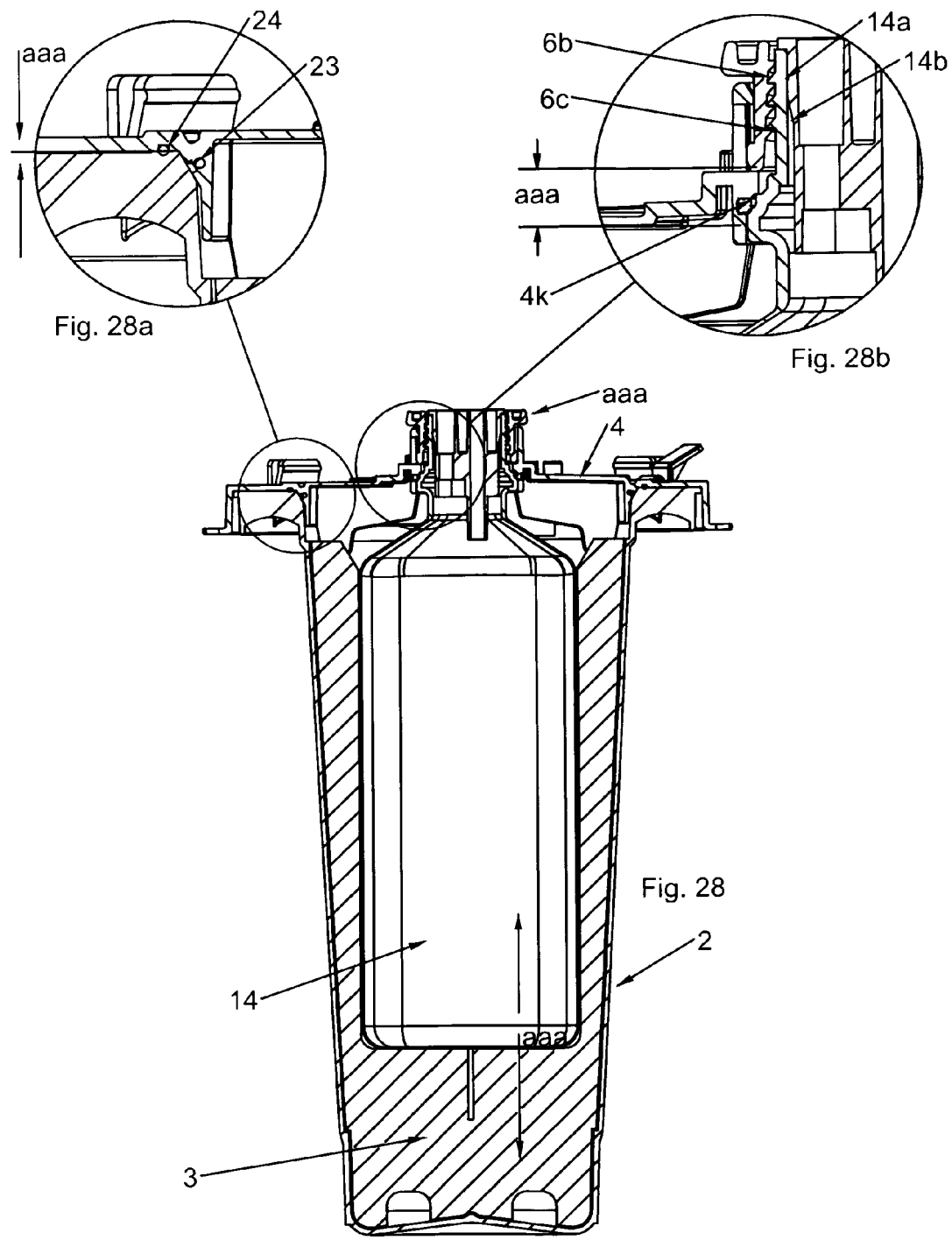
FIG. 28 is a cross sectional view of pour bottle 14' resting in measurement stand 3' with thrust handle 6' rotated in one direction shown by aura'.

FIG. 28 is a cross sectional view of canister system' with thrust handle 6' fully threaded in a clockwise direction aaa'.

FIG. 28 is a close up view of the relationship between canister 2' and lid 4' at o-ring seals 24' and 23' when thrust handle 6' is fully rotated in a clockwise rotation aaa'.

FIG. 28b is a close up showing thrust contact between 14e' and o-ring 22' as it sits in o-ring groove 4k'. FIG. 28b also shows handle thrust 6' in clockwise engagement aaa'. This figure also shows a relationship between contact points distance aaa' between thrust handle 6' and thrust bearing surface 4n' and thrust handle contact surface 6g'. Thrust handle 6' is rotated fully in a clockwise direction aaa' the results of the engagement of bottle threads and thrust handle threads result in thrust contact between 4n' and 6g' enacting a counter force which make for sealing o-ring 22' and bottle flange 14e'.

Figure 29:
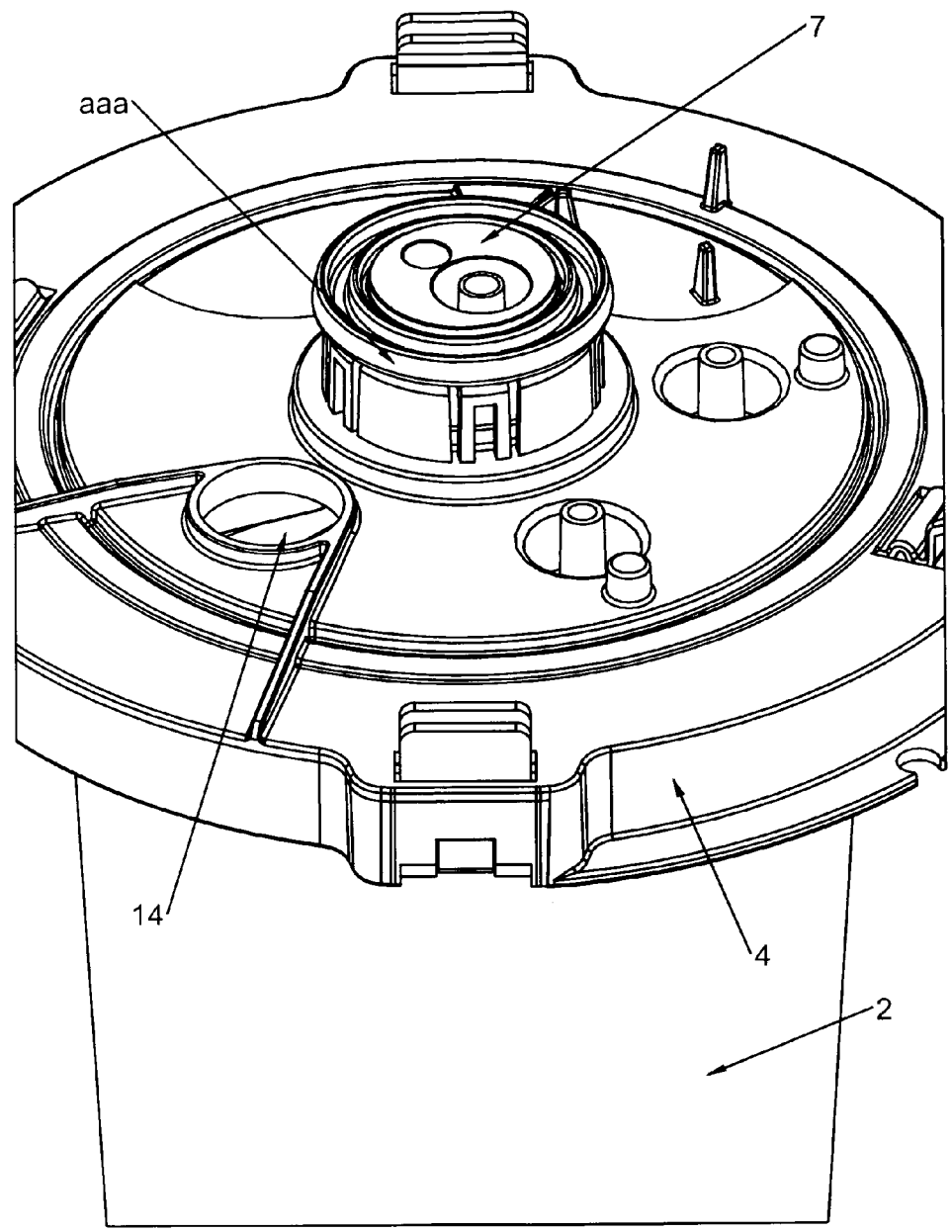
FIG. 29 is an isometric view of canister 2', lid 4', bottle 14', flush plug 7', in a perspective the shows the relationship of the parts when thrust handle 6' is completely rotated in the aaa' direction. The top of flush plug 7' is shown sitting disposed within a neck space of pour bottle 14' as a result of the tightening of thrust handle 6'. The top of flush plug 7' is flush with the level of the top of thrust handle 6'.

FIG. 29 shows thrust handle 6' in full clockwise aaa' and bottle 14' and flush plug 7' when threadably engaged to be level at the surface of flush plug top 7' and thrust handle rim 6'.

Figure 30:
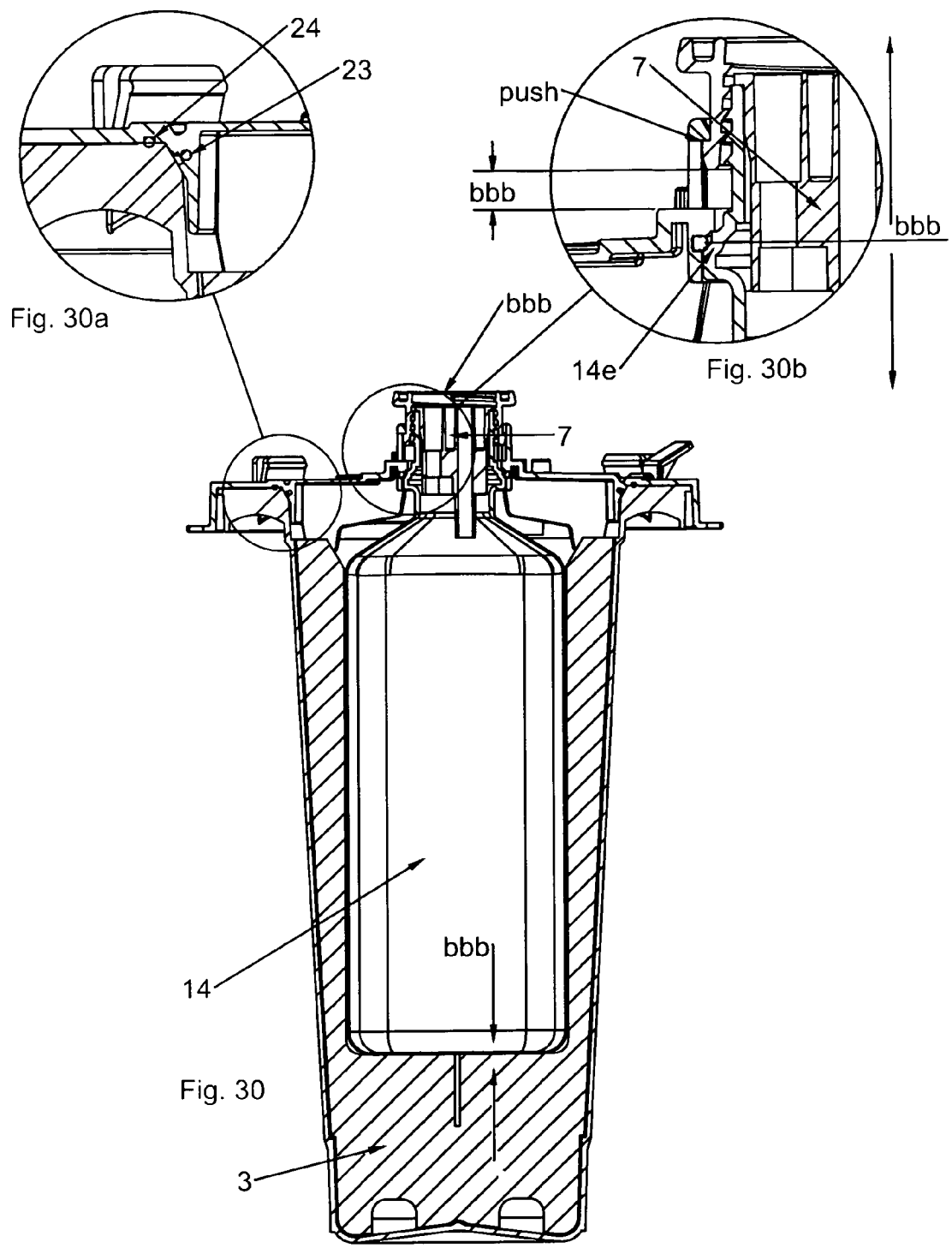
FIG. 30 is a cross sectional view of bottle 14' sitting in stand 3', with thrust handle 6' having bee rotated in the opposite direction.

FIG. 30 shows cross section view of canister system' whereby thrust handle 6' has been counterclockwise rotated bbb' to a point such that further rotation in a counterclockwise direction of thrust handle 6' would enact unsealing thrust forces between pour bottle 14' and measurement stand 3' and pour bottle 14e' and o-ring 22' as well as lifting lid4' up off of canister 2'.

FIG. 30a is a close up of canister 2' and lid 4' showing details of o-ring 24' and o-ring 23' at an intermediate rotation midway in the bbb' counterclockwise rotation whereby separation thrust would be enacted if thrust handle 6' were to be further rotated in the bbb' direction.

FIG. 30b is a close up view of the relationship between thrust handle 6' and lid 4' at push, showing two counter disposed retaining hooks which provide rotational thrust stoppage interference. This figure depicts counterclockwise rotation of thrust handle 6' at bbb' whereby if further rotated the tread engagement of thrust handle 6' and bottle 14' would provide downward thrust to bottle 14' relative to lid 4' causing an unsealing thrust between bottle flange 14e' and o-ring 22' in FIG. 30b. Further counterclockwise rotation bbb' of thrust handle 6' would cause additional push off thrust pressure bbb' as shown in FIG. 30 between bottle 14' and measurement stand 3' in effect enacting thrust forces lifting lid 4' up off of canister 2' separate seal 24' and seal 23' as shown in FIG. 30a.

Figure 31:
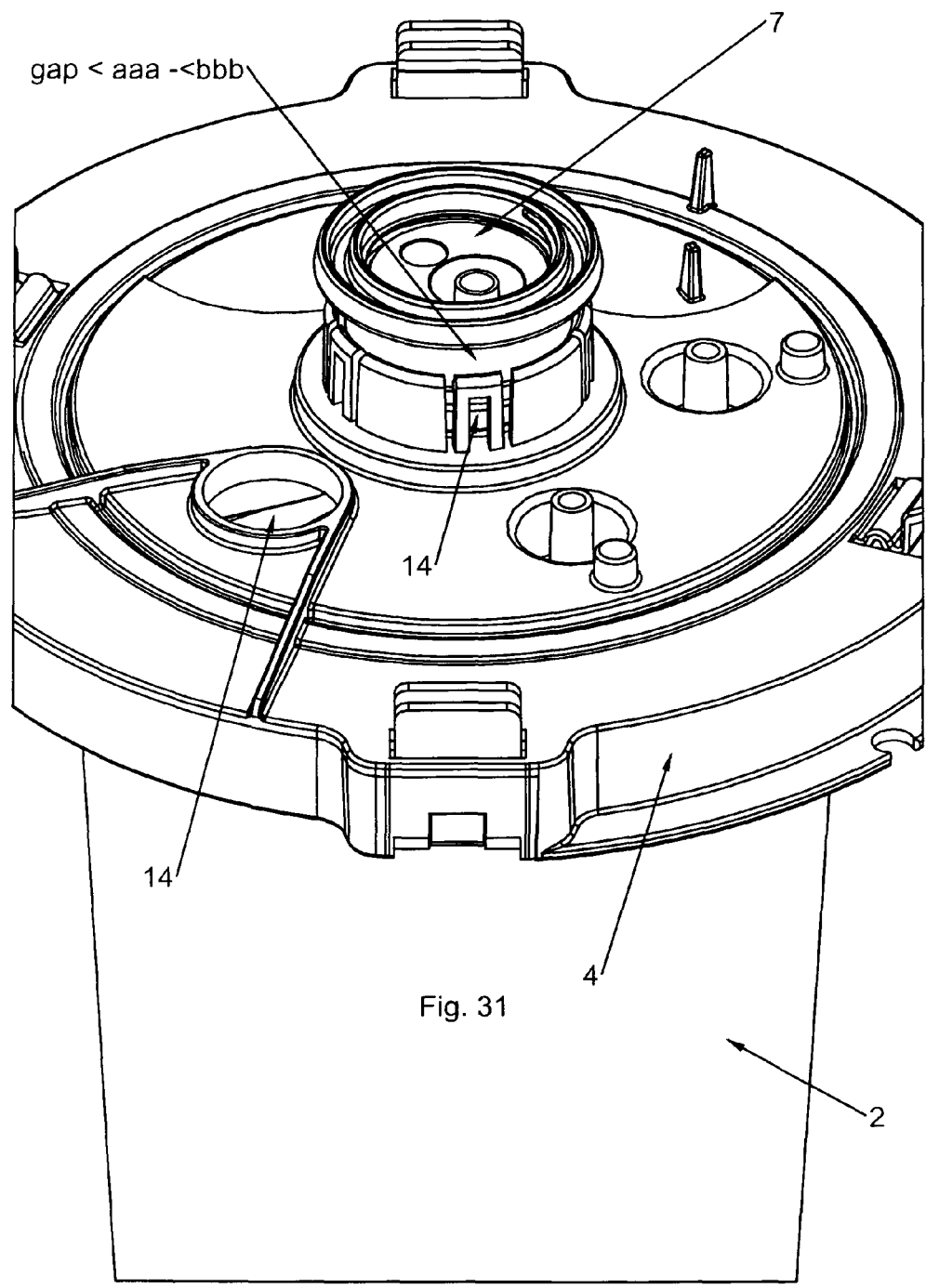
FIG. 31 is an isometric view showing a gap between thrust handle 6' and lid 4' at a point in thrust motion in the thrust handle rotation whereby threads of bottle neck 14' and threads of thrust handle 6' counter engage at a point where causing separation of canister system' seals disengaging.

FIG. 31 is an isometric close up view of canister 2', lid 4', canister 2', bottle 14', showing a gap between lid 4' and thrust handle 6'. This gap represents a thrust gap aaa' which is less the bbb'.

Figure 32:
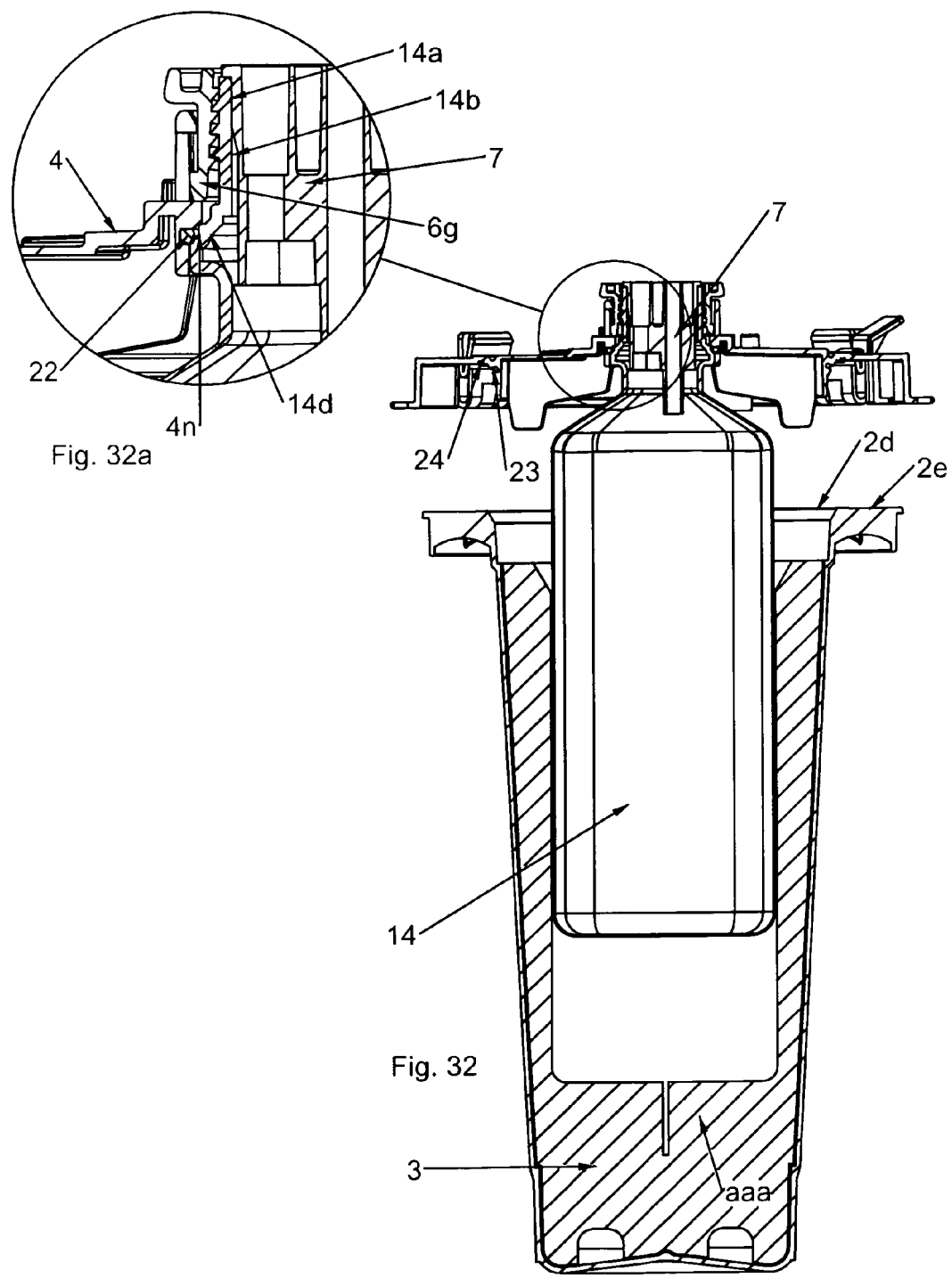
FIG. 32 is a cross sectional view of id 4' and bottle 14' having been pre-assembled and then subsequently placed in measurement stand 3' allowing sealing between canister 2' and lid 4' at seals 23' and 24'.

FIG. 32 is a cross sectional view of lid 4' in relationship to bottle 14' such that thrust handle 6' has been fully rotated in clockwise aaa' direction. This provides for complete seal between bottle 14' at 14e' and o-ring 22' sitting in o-ring groove 4k'. When bottle 14' is pre-assembled to lid 4' by full clockwise rotation aaa' of thrust handle 6' all sealing tolerance between bottle 14 and lid 4' have been made and when bottle 14' and lid 4' have been collectively dropped into measurement stand 3' within canister 2' sealing between canister 2' at sealing surfaces 2d' and 2e' are automatic, and all sealing tolerances have been closed and met for sealing the system', and canister 2' will seal with o-rings 23' and 24'.

FIG. 32a shows a close up of thrust handle 6' in full clockwise aaa' position showing how lid thrust surface 4n' and thrust handle bearing surface 6g' make contact and as thrust handle 6' is continued to be rotated in the clockwise direction the threads of thrust handle 6' engage the threads of bottle 14' enacting thrust causing bottle flange 14e' to press up against o-ring 22' in o-ring groove 4k' forming a seal there between.

Figure 33:
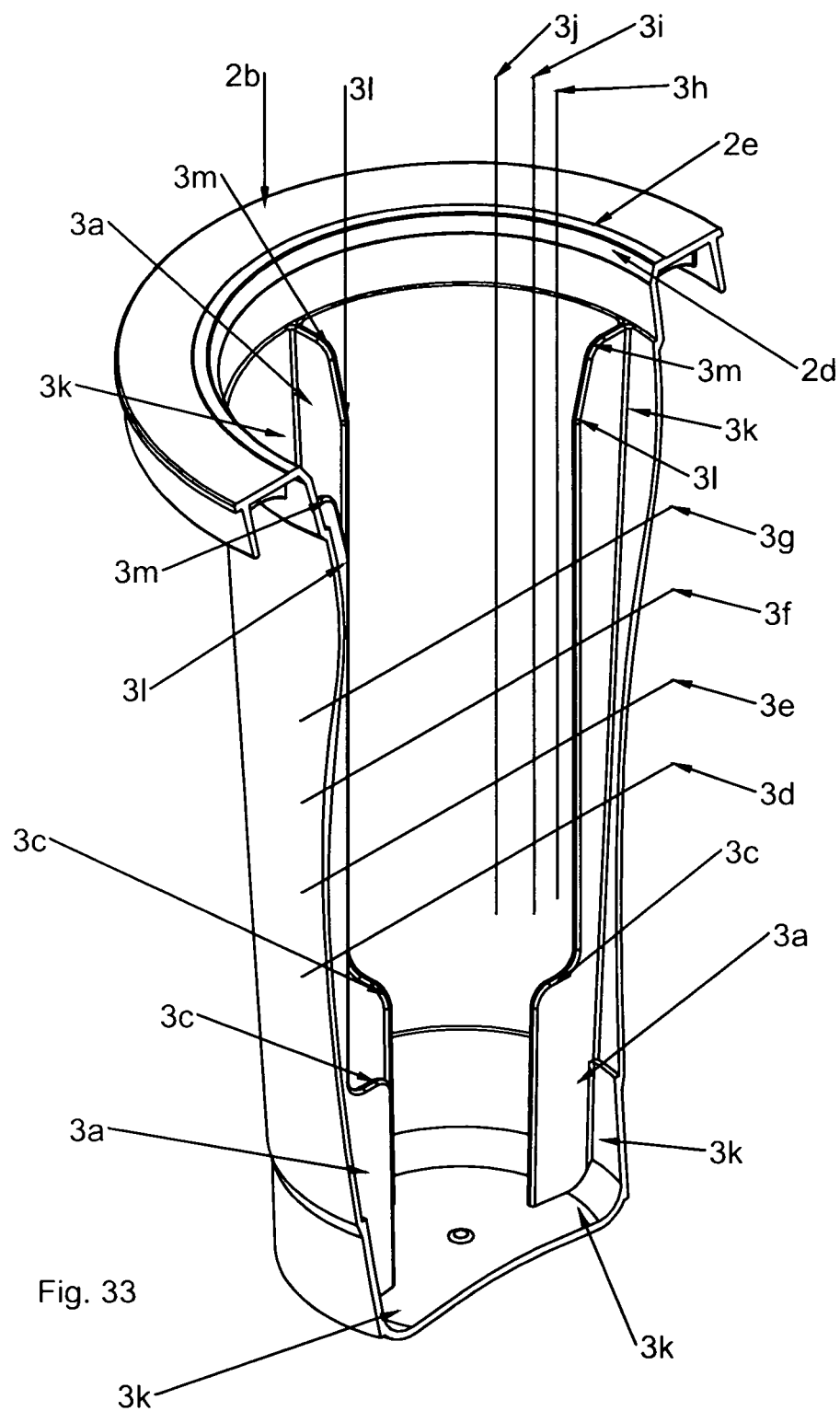
FIG. 33 is an isometric view of canister body 3" showing a first second third and fourth measurement depicted by 3a"(the fourth not shown). In this embodiment the canister may be manufactured with the measurement stands molded unitary with the canister body. These stands may be formed in alternative or composite mold cores having the requisite slotting and such a mold may be made to have separate cores or composite cores such that the canister 3" of different sizes and configuration may be made by altering one half or one side of the mold. Measurement stands project inwardly from the perimeter of the canister wall. 3". So that it orients the pour bottle horizontally and provides a rotational interference fit such that counter rotational forces may counteract rotational forces provided by thrust handle 6'.

FIG. 33 shown an isometric cutaway view of canister 2". Canister 2" embodies unitary measurement stands which have been molded unitarily with the perimeter of the canister 2" outer housing body. This can be shown at 3a", 3a", 3a" and the fourth 3a"(not shown), and at 3k", 3k", 3k". The unitary measurement provide a bottle support 3c", a bottle leads shown at 3l" and 3m". These unitary measurement stands 3a" may be formed in an injection mold or from a composite core of a mold half. It is noted that the core of the mold may be modified to for different measurement stands providing for the support of different bottle sizes an shown by 3d", 3e", 3f', 3g", 3h", 3i" 3j". The other important function of these measurement stands, is not only to provide indica which allows visual observation of the amount of fluent material collected in the bottle 14' and the canister 3', but to provide rotation interference in the event the bottle 14' rotates upon rotation of thrust handle 6'. This way the bottle will not rotate with thrust handle 6' preventing sealing and unsealing thrust forces.

Figure 34:
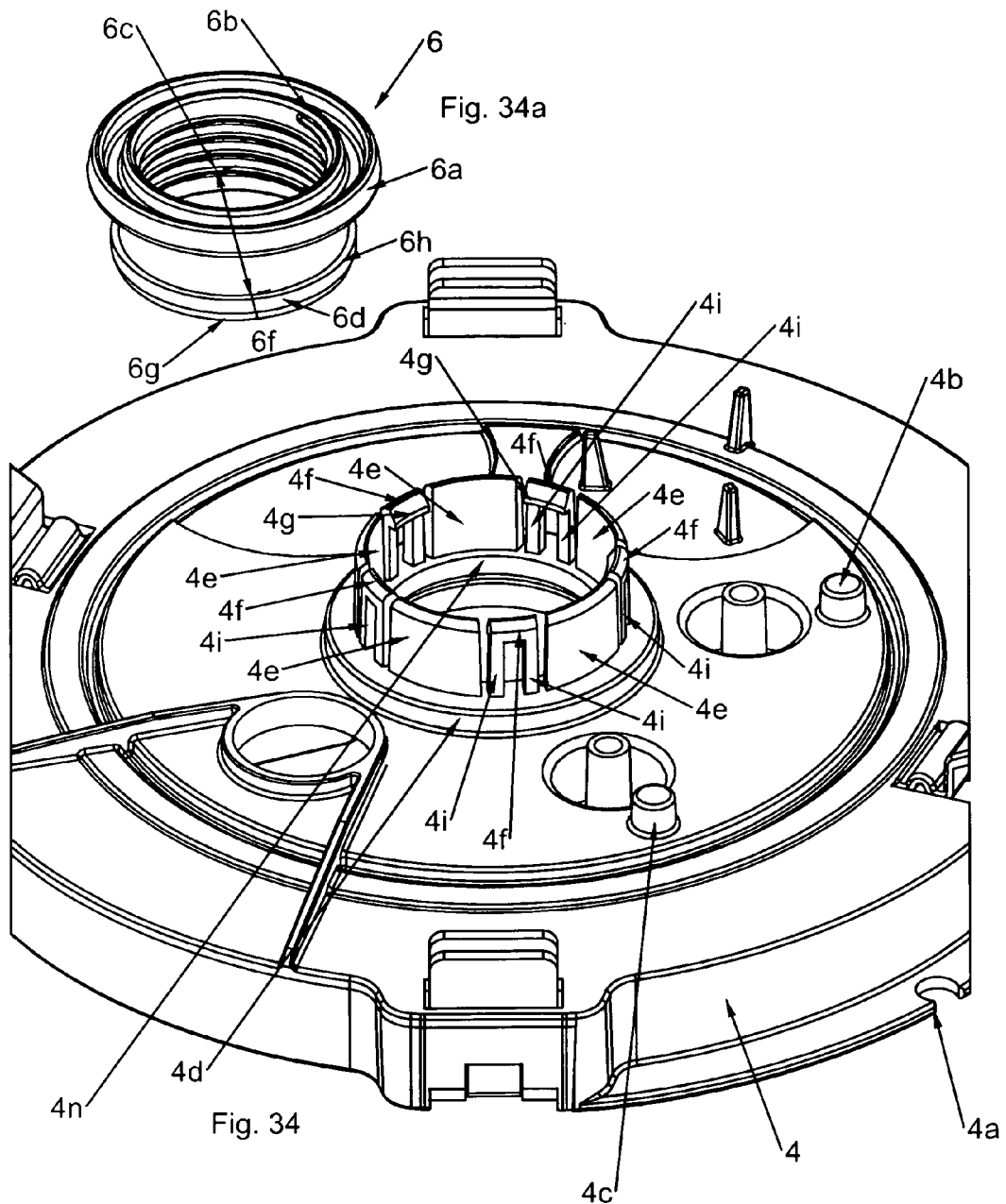
FIG. 34 is an isometric view of lid 4'.

FIG. 34 is a close up isometric view of lid 4' showing at 4a' a cutout hook in the rim of lid 4' for hanging or hooking/docking a suction tubing so that when bottles are switched out of the canister there is a place associated with the lid 4' to hold the tubing. 4c' and 4b' are retaining studs for spider cap covers. 4d' is a sealing surface for spider cap cover. 4n is a thrust bearing surfaced to abut against 6g' of thrust handle 6'. 4f' is shown in five places which comprise flexible retaining hooks to accommodate a snap assembly of thrust handle 6' to lid 4'. 4e' shown in five places show a thrust handle retaining wall to provide support for thrust hook rim 6d' as it slide up an down in reaction the thrust forces during operation. 4g' shown in five places shows snap fit hooks which operate as retaining hooks which interface with 6h' rim hook of thrust handle 6'. 6h' and 4g' function as counter-rotational thrust stop bearings creating interference hook and rim bearings such that as thrust handle 6' is counter rotated in direction bbb' at a certain point during thread thrust engagement between bottle 14' and threads 6b' and 6c' there is a rise stop bearing hook relationship that allows rotation of thrust handle 6' to provide a down thrust force on bottle 14' which effects unsealing between 4' and bottle 14' and lid 4' and canister 2' or canister 3" as shown in FIG. 33 of sheet 33.

Figure 35:
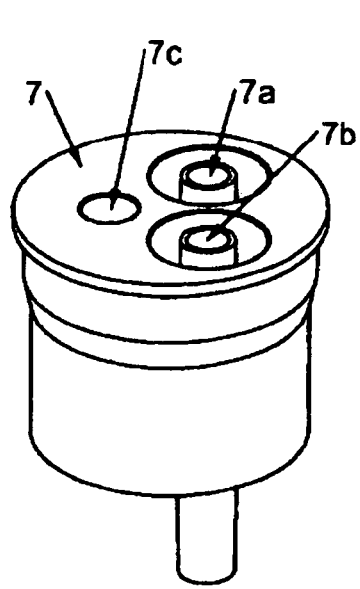
FIG. 35 is an isometric view of flush plug 7". This view shows flush plug 7" as a pressure exchange for a bottle neck wherein this particular provides a first and second in flow to the same pour bottle 14' shown by 7a", 7b" and a single outflow shown by 7c".

FIG. 35 shows an embodiment of flush plug 7' having inflow 7a" and inflow 7b" and outflow 7c". this embodiment of pressure exchange plug may be desirable where it is beneficial to connect more that one inflow tubing to a flush plug disposed in the neck of a pour bottle 14' and only one suction outflow draw path is sufficient leaving a flush plug disposed in the neck of a pour bottle.

Figure 35A:
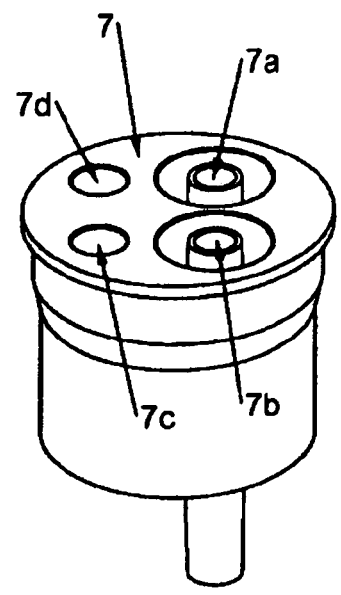
FIG. 35a is an isometric view of flush plug 7'" showing first, second third and fourth vacuum pressure exchange lumens. Two lumens 7a'" and 7b'" are shown for providing inflow to the same pour bottle 14', and two additional lumens 7d'" and 7e'" are shown for providing two outflows from the same pour bottle 14'.

FIG. 35a depicts a flush plug embodiment 7'" showing inflow 7a'", 7b'", outflow 7c'" and outflow 7d'". It is sometimes desirable to have two inflow and two outflow, or any combination of inflows and outflows direction vacuum draw path pressure toward and away from a pour bottle 14' through a flush plug disposed in the neck of a pour bottle derived from a supply chain. It is understood that any number of inflow and outflow connection may be made with pour bottle 14' whereas any number of combinations may fit particular draw path and pressure volume situations, as well as different procedures may require different supply chain solutions to meet a variety of needs.

What is claimed is:

1. A supply chain method comprising,
   a) egressing fluent material from a container,
   b) retaining said container inside a canister, said canister configured with a plurality of unitary formed support members extending inward and upward to orient said container such that a first seal between said container and a lid, and a second seal between said canister and said lid may be established,
   c) drawing vacuum flow along a vacuum draw path away from a space between said container and said canister, away from said container through an atmospheric exchange egress plug port located at the neck of said container, through an atmospheric exchange ingress plug port located at the neck of said container, away from a source of waste toward a vacuum draw source, whereby application of said vacuum flow causes waste material to be transferred toward and/or into said container.

2. A supply chain method of claim wherein said retention is applied to differently configured containers.

3. A supply chain method of claim wherein said retention is applied to containers of different volumes.

4. A supply chain method of claim wherein said retention is applied to containers of different shape.

5. A supply chain method comprising,
   a) egressing material from a container,
   b) retaining said container inside a housing, said container configured to receive different materials from which at least a portion emanates from a health care subject, said orientation to include said container configured to co-act inside a canister to reduce implosion forces at a location along a vacuum draw path, a plug located at said container neck configured to egress and ingress a vacuum flow, a plurality of unitarily formed support members configured to align said container in said canister to establish alignment of at least two seals, said flow configured to be drawn by a vacuum source away from a space between said canister and said container, into and out of the neck of said container and into at least one opening in said draw path whereby application of said vacuum flow causes said different materials to be transferred toward and/or into said container.

6. A supply chain method of claim 5 wherein said retention is applied to differently configured containers.

7. A supply chain method claim 5 wherein said retention is applied to containers of different volume.

8. A supply chain method of claim 5 wherein said retention is applied to containers of different shape.

9. A supply chain method comprising,
   a) egressing material from a container, said container being configured in part to seal a vacuum draw path, said container being configured to egress and ingress vacuum flow through three or more plug ports located at the neck of said container, said vacuum flow configured to be confined by said path,
   b) retaining said container within an enclosure with respect to a source of waste, said retention to include supporting said container with a plurality of unitary support members inside said enclosure, said vacuum flow being configured to be drawn away from a space between said container and said enclosure, and into at least one opening in said vacuum draw path during said confinement whereby application of said vacuum flow causes waste material to be transferred toward and/or into said container.

10. A supply chain method of claim 9 wherein said retention is applied to differently configured containers.

11. A supply chain method of claim 9 wherein said retention is applied to containers of different volumes.

12. A supply chain method of claim 9 wherein said retention is applied to containers of different shape.

13. A supply chain method comprising,
   a) egressing material from a container, said container being configured for said egress of said material toward a non-anatomic location,
   b) retaining said container inside an outer housing at a location along a vacuum draw path, said retention to include egress of said reduced pressure away from a space outside said container and said outer housing toward a source of vacuum and through at least two vacuum flow egress plug ports located at the neck of said container in association with drawing waste away from a health care subject, said housing configured to support said container with a plurality of unitary support members to orient said container within said housing to at least in part contain said reduced pressure within said vacuum draw path to provide at least two vacuum draw path seals whereby application of said reduced pressure causes transfer of waste material toward and/or into said container.

14. A supply chain method of claim 13 wherein said retention is applied to containers of different sizes.

15. A supply chain method of claim 13 wherein said retention is applied to containers of different shapes.

16. A supply chain method of claim 13 wherein said retention is applied to containers of different volumes.

17. A supply chain method comprising,
   a) egressing material from a container.
   b) retaining said container inside a housing, said container located to receive waste with respect to a health care subject, said retention to include a vacuum flow, a vacuum force, a draw path having at least one opening, a vacuum source configured to apply said vacuum flow away from a space between said container and said housing, said vacuum source configured to apply said vacuum flow during ingress of said flow into a draw path opening and through plug ports located at the neck of said container, said path being configured to confine said flow at least in part by a plurality of unitary support members configured to cause alignment of draw path seals whereby application of said vacuum flow causes said waste to be transferred toward and/or into said container.

18. A supply chain method of claim 17 wherein said retention is applied to differently configured containers.

19. A supply chain method of claim 17 wherein said retention is applied to containers having different numbers of ports.

20. A supply chain of claim 17 wherein said retention is applied to containers having previously egressed different materials.

21. A supply chain method comprising,
   a) egressing material from a container with respect to an anatomic location of a health care subject,
   b) retaining said container in waste material ingress orientation inside a housing with respect to separate anatomic locations, a vacuum force configured to draw a vacuum flow into an opening of a draw path, said draw path configured to egress said flow out of a space between said container and said housing, a plug configured to egress and ingress said flow at the neck of said container, at least two vacuum draw path seals established in part by a plurality of unitary support members configured to locate said container in said housing whereby application of said vacuum flow causes said waste to be transferred toward and/or into said container.

22. A supply chain method of claim 21 wherein said retention is applied to containers of various sizes.

23. A supply chain method of claim 21 wherein application of said retention is applied to containers of various shapes.

24. A supply chain method of claim 21 wherein application of said retention is applied to containers of various volumes.

* * * * *

UNITED STATES PATENT AND TRADEMARK OFFICE
CERTIFICATE OF CORRECTION

PATENT NO. : 8,939,950 B2
APPLICATION NO. : 12/927049
DATED : January 27, 2015
INVENTOR(S) : Jack W Romano and Adam L Smith It is certified that error appears in the above-identified patent and that said Letters Patent is hereby corrected as shown below:

In the Specification
-Column 1, line 31: delete the first "canister" and insert --canisters-- to read "as canisters and/or canister"...
-Column 1, line 65: delete "Organization" and insert --Organizations-- to read "Purchasing Organizations, leading"...
-Column 2, line 21: insert --that-- between -durometer- and -should- to read "durometer that should"...
-Column 2, line 34: delete "assemble" and insert --assembly-- to read "easy assembly and"...
-Column 2, line 44: delete "Opening" and insert --Openings-- to read "Openings must be"...
-Column 2, line 47: delete "are" at the end of the line and insert --care-- to read "health care"...
-Column 2, line 50: delete "in" at the end of the line.
-Column 2, line 51: delete "the y" between -systems- and -should- to read "systems should"...
-Column 2, line 59: delete "seal" and insert --seals-- to read "checking seals must"...
-Column 2, line 61: delete "time" and insert --times-- to read "many times the"...
-Column 3, line 17: delete "dimension" and insert --dimensions-- to read "different dimensions from"...
-Column 3, line 32: delete "interior" and insert --interiors-- to read "interiors of preferably"...
-Column 3, line 33: insert --is-- between -and- and -taught- to read "and is taught"...
-Column 3, line 54: delete "difficulty" and insert --difficult-- to read "sometimes difficult ergonomics"...
-Column 3, line 59: delete "ore" and insert --more-- to read "are more difficult"...
-Column 3, line 63: delete "id" and insert --in-- to read "and in combination"...
-Column 3, line 67: delete "purchase" and insert --purchased-- to read "is purchased to replace"...
-Column 4, line 11: delete "This" and insert --The-- to read "canister. The disadvantages"...
-Column 4, line 16: insert --an-- between -is- and -additional- to read "is an additional"...
-Column 4, line 26: delete "id" and insert --is-- to read "The system is"...
-Column 4, line 30: delete "liner" and insert --liners-- to read "lids and liners can"...
-Column 4, line 32: delete "use" and insert --used-- to read "be used with"...
-Column 4, line 39: delete "container" and insert --containers-- to read "collection containers include"...

Signed and Sealed this
Twelfth Day of May, 2015

Michelle K. Lee
*Director of the United States Patent and Trademark Office*

-Column 4, line 51: delete "canister and it s" and insert --canisters and its-- to read "stackable canisters and its associated"...
-Column 4, line 59: delete "dies-assembly" and insert --disassembly-- to read "and disassembly features"...
-Column 4, line 60: delete "May" and insert --Many-- to read "strength. Many of the"...
-Column 4, line 62: delete "Require" and insert --require-- to read "design require more"...
-Column 4, line 64: delete "=are" and insert --are-- to read "that are not"...
-Column 4, line 67: delete "assemble" and insert --assembled-- to read "be assembled with"...
-Column 5, line 15-16: delete "container" and insert --containers-- to read "delivery containers which"...
-Column 5, line 30: insert --of-- between -collection- and -waste- to read "collection of waste"...
-Column 5, line 40: delete "solution" and insert --solutions-- to read "intravenous solutions, parenteral"...
-Column 5, line 41: delete "container" and insert --containers-- to read "containers and the like"...
-Column 5, line 50: delete "the" and insert --then-- to read "and then integrates"...
-Column 5, lines 54-55: delete "fabrication" and insert --fabrications-- to read "container fabrications applicable"...
-Column 5, line 55: delete the second "applicable to the" to read "fabrications applicable to the instant case"...
-Column 5, line 60: delete "knows and" and insert --known as-- to read "commonly known as a"...
-Column 5, line 60: delete "close" and insert --closed-- to read "and a closed top"...
-Column 6, line 4: delete "these" and insert --the-- to read "embodiments of the instant"...
-Column 6, line 20: delete the second "the" to read "(unnecessary) need for"...
-Column 6, line 24-25: delete the second "container" and insert --containers-- to read "disposable containers when a fluid"...
-Column 6, line 36: delete "product" and insert --products-- to read "other products such as"...
-Column 6, line 41: delete "solution" and insert --solutions-- to read "solutions and the like"...
-Column 6, line 57: delete "suitable" and insert --suitably-- to read "be suitably integrated"...
-Column 6, line 59: delete "container" and insert --containers-- to read "Other containers such as"...
-Column 6, line 62: delete "teaching" and insert --teachings-- to read "These teachings are"...
-Column 7, line 9: insert --blow mold-- between -continuous- and the first -containers,- to read "continuous blow mold containers,"...
-Column 7, line 10: delete "const" at the end of the line to read "been effectively"...
-Column 7, line 13: delete "solution. Option" and insert --solutions and options-- to read "various solutions and options solving"...
-Column 7, line 39: delete "distributing" and insert --distribution-- to read "transforming distribution containers"...
-Column 7, line 40: delete "dispose" and insert --disposal-- to read "a disposal and"...
-Column 7, line 41: delete "containers" and insert --containers is-- to read "supply containers is an environmental"...
-Column 7, line 44: delete "to =options" and insert --options-- to read "confers options and advantages"...
-Column 7, line 44: delete the second "and" and insert --as-- to read "advantages as disclosed"...
-Column 7, line 55: delete "this plastic wall" and insert --thin plastic walls-- to read "relatively thin plastic walls sometimes"...

CERTIFICATE OF CORRECTION (continued)
U.S. Pat. No. 8,939,950 B2

-Column 7, line 55: insert --to-- between -down- and -the- to read "down to the"...
-Column 7, line 67: delete "I" and insert --in-- to read "thickness in these"...
-Column 7, line 67: delete "hot" and insert --not-- to read "are not generally"...
-Column 8, line 50-51: delete "configuration" and insert --configurations-- to read "bottle neck configurations which"...
-Column 8, line 54: delete "a" at the end of the line...
-Column 9, line 19: insert --a-- between -pour- and -solution- to read "pour a solution"...
-Column 9, line 22: insert --is to pour a-- between -invention- and -liquid- to read "invention is to pour a liquid"...
-Column 10, line 5: delete "container" and insert --containers-- to read "collection containers within"...
-Column 10, line 20: delete "fro" and insert --for-- to read "sequence for liquid"...
-Column 10, line 26: delete "position" and insert --positioned-- to read "is positioned on the"...
-Column 10, line 62: delete "force" and insert --forces-- to read "draw forces to"...
-Column 11, line 1: insert --a-- between -fabricating- and -liquid- to read "fabricating a liquid"...
-Column 11, line 11: delete "suctioning wand with" to read "wand in waste material"...
-Column 11, line 37: delete "bottle" and insert --bottles-- to read "enclosing bottles fabricated"...
-Column 12, line 3: delete "a salability" and insert --sealability-- to read "causes sealability of a"...
-Column 12, line 32: delete "show" and insert --shown-- to read "embodiment shown in"...
-Column 12, line 55: delete "4 and container 14.".
-Column 12, line 61: delete "process" and insert --processed-- to read "is processed into"...
-Column 12, line 63: delete "19_" and insert --19c-- to read "through 19c of"...
-Column 12, line 66: delete "closing" and insert --closed-- to read "having closed seal"...
-Column 13, line 35: delete "an" and insert --and-- to read "2 and lid 4"...
-Column 13, line 40: delete "Figure" and insert --Figures-- to read "in Figures on"...
-Column 13, line 48: delete "124" and insert --14-- to read "container 14 and"...
-Column 13, line 55: delete "10 b" and insert --10b-- to read "FIG. 10b further"...
-Column 14, line 4: delete "14 a" and insert --14a-- to read "FIG. 14a further"...
-Column 14, line 36: delete "un superimpose" and insert --un-superimpose-- to read "un-superimpose vertically"...
-Column 14, line 40: delete "lack" and insert --lock-- to read "lock 5."...
-Column 14, line 43: delete "if" and insert --of-- to read "4a9 of lid 4"...
-Column 14, line 51: delete "g" to read "depicting its"...
-Column 14, line 52: delete "dimensions" and insert --dimension-- to read "a dimension from its"...
-Column 15, line 3: delete "18 f" and insert --18f-- to read "FIG. 18f is"...
-Column 15, line 3: delete "18 e" and insert --18e-- to read "FIG. 18e but"...
-Column 15, line 24: delete "lavational" and insert --elevational-- to read "side elevational cross"...
-Column 15, line 32: delete "handoff" and insert --hand of-- to read "one hand of an operator"...
-Column 15, line 43: delete "two" and insert --2-- to read "canister 2 in fairly"...
-Column 15, line 45: delete "so" to read "enclosing sterile/other"...
-Column 15, line 46: insert --in-- between -is- and -sequence- to read "is in sequence"...
-Column 15, line 49: add ')' at the end of the line to read "removed.)"...
-Column 15, line 53: delete "s" and insert --of a-- to read "container of a lid 4"...
-Column 15, line 55: delete "component s" and insert --components-- to read "the components contact stack"...
-Column 16, line 14: delete "begins" and insert --beginning-- to read "canister beginning at a"...

CERTIFICATE OF CORRECTION (continued)

-Column 16, line 52: delete "the" and insert --that-- to read "perspective that shows"...
-Column 16, line 59: delete "bee" and insert --been-- to read "having been rotated"...
-Column 16, line 64: delete "an" and insert --a-- to read "defining a push"...
-Column 17, line 6: delete "id" and insert --lid-- to read "view of lid 4'"...
-Column 17, line 11: delete "indirection" and insert --in direction-- to read "rotated in direction aaa'"...
-Column 17, line 24: delete "configuration" and insert --configurations-- to read "configurations may be"...
-Column 17, line 54: delete "two" and insert --2-- to read "Canister body 2 is shown"...
-Column 17, line 55: delete "2I" and insert --2i-- to read "2i, interface"...
-Column 18, line 22: insert --to-- between -engage- and -handle- to read "engaged to handle"...
-Column 18, line 23: delete "if" and insert --in-- to read "6w in a fully"...
-Column 18, line 45: delete "5 a" and insert --5a-- to read "FIG. 5a shows"...
-Column 18, line 47: delete "increasing" and insert --increasingly-- to read "increasingly engages"...
-Column 18, line 49: insert --,-- between -7- and -soft- to read "plug 7, soft"...
-Column 19, line 4: delete "weal" and insert --seal-- to read "bottle/lid seal 4a3"...
-Column 19, line 5: delete "portinsurface" and insert --portion surface-- to read "bearing portion surface 4a9"...
-Column 19, line 14: delete "assemble" and insert --assembly-- to read "bottle assembly bevel"...
-Column 19, line 16: delete "an" and insert --and-- to read "canister 2 and lid 4"...
-Column 19, line 34: delete "of" and insert --to-- to read "19 to 23"...
-Column 19, line 35: delete "Sixteen" and insert --16-- to read "16 depicts"...
-Column 19, line 38: delete "become" and insert --becomes-- to read "which becomes 14"...
-Column 19, line 45: delete "a" and insert --an-- to read "in an unsealing"...
-Column 19, line 52: delete "8 b" and insert --8b-- to read "FIG. 8b is a"...
-Column 19, line 64: delete "show" and insert --shown-- to read "Also shown is"...
-Column 20, line 3: delete "65j" and insert --6j-- to read "force 6j continuing"...
-Column 20, line 19: delete "view" and insert --views-- to read "section views as"...
-Column 20, line 21: delete "and" and insert --in an-- to read "taken in an intermediate"...
-Column 21, line 2: insert --of-- between -2b- and -canister- to read "surface 2b of canister"...
-Column 21, line 4: delete "21b" and insert --12b-- to read "FIG. 12b shows"...
-Column 21, line 13: insert --of-- between -part- and -which- to read "part of which"...
-Column 21, line 22: delete "at effected" and insert --are affected-- to read "leads are affected"...
-Column 21, line 35: delete "ht" and insert --the-- to read "for the purposes"...
-Column 21, line 54: delete "crass" and insert --cross-- to read "is a cross sectional"...
-Column 22, line 43: delete "handle6" and insert --handle 6-- to read "handle 6"...
-Column 22, line 44: delete "defined" and insert --defines-- to read "which defines a"...
-Column 22, line 45: delete "lid4" and insert --lid 4-- to read "the lid 4 and"...
-Column 22, line 56: delete "part" and insert --parts-- to read "the parts are"...
-Column 22, line 62: delete "assistance" and insert --assist-- to read "to assist in the"...
-Column 23, line 5: delete "41d" and insert --14d-- to read "xx-bottle 14d"...
-Column 23, line 35: delete "Show" and insert --Shown-- to read "features. Shown in"...
-Column 23, line 42: delete "hoe" and insert --hose-- to read "patient hose 11"...
-Column 23, line 61: insert --stand-- between -measuring- and -3- to read "measuring stand 3"...
-Column 24, line 17: delete "volume" and insert --volumes-- to read "and volumes, and shapes"...
-Column 24, line 18: delete "possible" and insert --possibly-- to read "and possibly more"...

-Column 24, line 25: delete "if" and insert --in-- to read "depicted in FIGS."...
-Column 24, line 25: delete "18 d" and insert --18d-- to read "FIGS. 18d through"...
-Column 24, line 30: delete "show" and insert --shown-- to read "it is shown how"...
-Column 24, line 31: delete "sized" and insert --sizes-- to read "and sizes may"...
-Column 24, line 35: delete "dimention" and insert --dimensions-- to read "dimensions to allow"...
-Column 24, line 36: delete "sized" and insert --sizes-- to read "and sizes into"...
-Column 24, line 45: delete the second "and" and insert --an-- to read "for an operator"...
-Column 24, line 48: delete "a" and insert --an-- to read "with an empty"...
-Column 24, line 49: delete "places" and insert --placed-- to read "17a placed within"...
-Column 24, line 53: delete "shows" and insert --shown-- to read "is shown as"...
-Column 24, line 65: delete "initiate" and insert --initiated-- to read "forces initiated by the"...
-Column 25, line 9: delete "to" and insert --by-- to read "canister by holding"...
-Column 25, line 11: delete the second "forces" to read "forces emanating from contact"...
-Column 25, line 12: insert --4-- between -lid- and -at- to read "with lid 4 at"...
-Column 25, line 20: delete "the" and insert --to-- to read "reduced to one"...
-Column 25, line 25: insert --a-- between -has- and -slight- to read "has a slight"...
-Column 25, line 41: delete "an did" and insert --and lid-- to read "canister 2 and lid"...
-Column 25, line 48: delete "a" and insert --an-- to read "defining an easy"...
-Column 25, line 55: delete the "d" at the end of the line to read "lid 4 and canister 2"...
-Column 25, line 65: delete the "t" and insert --a-- to read "into a plurality"...
-Column 26, line 34: insert --is-- between -shown- and -canister- to read "shown is canister"...
-Column 26, line 48: delete "being defined as" to read "defined as thrusting"...
-Column 26, line 62: delete "." at the end of the line to read "engage threads 14a' through"...
-Column 27, line 51: delete "the" and insert --than-- to read "less than bbb'"...
-Column 28, line 4: delete "shown" and insert --shows-- to read "FIG. 33 shows an"...
-Column 28, line 10: delete "provide" and insert --stand provides-- to read "measurement stand provides"...
-Column 28, line 14: delete "to" between -modified- and -for- to read "modified for"...
-Column 28, line 33: delete "show" and insert --shows-- to read "places shows a"...
-Column 28, line 34: delete "slide" and insert --slides-- to read "as it slides up an"...
-Column 28, line 63: delete "connection" and insert --connections-- to read "outflow connections may"...

In the Claims
-Column 30, line 54: insert --method-- between -chain- and -of- to read "a supply chain method of claim 17"...